(12) United States Patent
Stieber et al.

(10) Patent No.: US 8,003,657 B2
(45) Date of Patent: Aug. 23, 2011

(54) HETEROCYCLIC SUBSTITUTED BISARYLUREA DERIVATIVES

(75) Inventors: Frank Stieber, Heidelberg (DE); Alfred Jonczyk, Darmstadt (DE); Guenter Hoelzemann, Seeheim-Jugenheim (DE); Hans-Peter Buchstaller, Griesheim (DE); Lars Thore Burgdorf, Frankfurt am Main (DE); Wilfried Rautenberg, Reinheim (DE); Hartmut Greiner, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 1089 days.

(21) Appl. No.: 11/577,270

(22) PCT Filed: Oct. 6, 2005

(86) PCT No.: PCT/EP2005/010744
§ 371 (c)(1),
(2), (4) Date: Apr. 13, 2007

(87) PCT Pub. No.: WO2006/040056
PCT Pub. Date: Apr. 20, 2006

(65) Prior Publication Data
US 2009/0215799 A1    Aug. 27, 2009

(30) Foreign Application Priority Data

Oct. 13, 2004  (EP) .................................... 04024369
Aug. 3, 2005   (EP) .................................... 05016845

(51) Int. Cl.
*A61K 31/44*    (2006.01)
*C07D 401/12*   (2006.01)
(52) U.S. Cl. .............. 514/264.1; 514/340; 514/395; 544/279; 546/272.4; 548/255
(58) Field of Classification Search ............... None
See application file for complete search history.

(56) References Cited

U.S. PATENT DOCUMENTS

| 2003/0027914 A1 | 2/2003 | Suzuki et al. |
| 2003/0144278 A1 | 7/2003 | Riedl et al. |
| 2004/0014756 A1 | 1/2004 | Michaelides et al. |

FOREIGN PATENT DOCUMENTS

| WO | 99/32436 | 7/1999 |
| WO | 01/51456 | 7/2001 |
| WO | 01/57008 | 8/2001 |
| WO | 02/44156 | 6/2002 |
| WO | 02/092576 | 11/2002 |
| WO | 03/068223 | 8/2003 |
| WO | WO 03/099771 | * 12/2003 |
| WO | 2005/075425 | 8/2005 |

OTHER PUBLICATIONS

West, Anthony R., Solid State Chemistry and its Applications, Wiley, New York, 1988, pp. 358 & 365.*
Manley et al., Urea derivatives of STI571 as inhibitors of Bcr-Abl and PDGFR kinases, Bioorganic & Medicinal Chemistry Letters, vol. 14, Issue 23, pp. 5793-5797, (2004).

* cited by examiner

Primary Examiner — Zinna Northington Davis
(74) Attorney, Agent, or Firm — Perkins Coie LLP

(57) ABSTRACT

The present invention relates to heterocyclic substituted bisarylurea derivatives of formula I, the use of the compounds of formula I as inhibitors of one or more kinases, the use of the compounds of formula I for the manufacture of a pharmaceutical composition and a method of treatment, comprising administering said pharmaceutical composition to a patient.

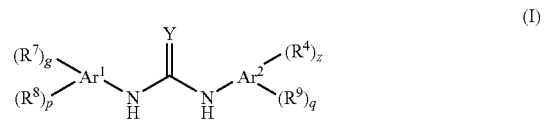

(I)

12 Claims, No Drawings

HETEROCYCLIC SUBSTITUTED BISARYLUREA DERIVATIVES

This application is a 371 of PCT/EP2005/010744 filed Oct. 6, 2005.

The present invention relates to heterocyclic substituted bisarylurea derivatives, said bisarylurea derivatives as medicaments, said bisarylurea derivatives as inhibitors of one or more kinases, the use of bisarylurea derivatives according to the invention for the manufacture of a pharmaceutical, a method for producing a pharmaceutical composition containing said bisarylurea derivatives, the pharmaceutical composition obtainable by said method and a method of treatment, comprising administering said pharmaceutical composition.

The instant invention preferably relates to compounds which are able to interact, inhibit regulate and/or modulate the signal transduction of kinases, especially receptor tyrosine kinases and/or serine/threonine kinases, pharmaceutical preparation which comprises said compounds and the use of said compounds for the treatment of diseases caused, mediated and/or propagated by kinases.

Protein phosphorylation is a fundamental process for the regulation of cellular functions. The coordinated action of both protein kinases and phosphatases controls the levels of phosphorylation and, hence, the activity of specific target proteins. One of the predominant roles of protein phosphorylation is in signal transduction, where extracellular signals are amplified and propagated by a cascade of protein phosphorylation and dephosphorylation events, e.g. in the ras/raf pathway.

Activated Ras is necessary for the activation of the c-raf-1 proto-oncogene, but the biochemical steps through which Ras activates the Raf-1 protein (Ser/Thr) kinase are now well characterized. It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype see: Daum et al. (1994) Trends Biochem. Sci., 19, 474-80; Fridman et al. (1994) J. Biol. Chem., 269, 30105-8. Kolch et al. (1991) Nature, 349, 426-28) and for review Weinstein-Oppenheimer et al. Pharm. & Therap. (2000), 88, 229-279.

Similarly, inhibition of raf kinase (by antisense oligodeoxynucleotides) has been correlated in vitro and in vivo with inhibition of the growth of a variety of human tumor types (Monia et al., Nat. Med. 1996, 2, 668-75; Geiger et al. (1997), Clin. Cancer Res. 3(7): 1179-85; Lau et al. (2002), Antisense Nucl. Acid. Drug Dev. 12(1): 11-20; McPhillips et al. (2001), Br. J. Cancer 85(11): 1753-8).

Raf serine- and threonine-specific protein kinases are cytosolic enzymes that stimulate cell growth in a variety of cell systems (Rapp, U. R., et al. (1988) in The oncogene handbook; T. Curran, E. P. Reddy, and A. Skalka (ed.) Elsevier Science Publishers; The Netherlands, pp. 213-253; Rapp, U. R., et al. (1988) Cold Spring Harbor Sym. Quant. Biol. 53:173-184; Rapp, U. R., et al. (1990) Inv Curr. Top. Microbiol. Amunol. Potter and Melchers (eds), Berlin, Springer-Verlag 166:129-139).

Three isozymes have been characterized:
c-Raf (also named Raf-1, c-raf-1 or c-rafl) (Bonner, T. I., et al. (1986) Nucleic Acids Res. 14:1009-1015). A-Raf (Beck, T. W., et al. (1987) Nucleic Acids Res. 15:595-609), and B-Raf (Qkawa, S., et al. (1998) Mol. Cell. Biol. 8:2651-2654; Sithanandam, G. et al. (1990) Oncogene: 1775). These enzymes differ in their expression in various tissues. Raf-1 is expressed in all organs and in all cell lines that have been examined, and A- and B-Raf are expressed in urogenital and brain tissues, respectively (Storm, S. M. (1990) Oncogene 5:345-351).

Raf genes are proto-oncogenes: they can initiate malignant transformation of cells when expressed in specifically altered forms. Genetic changes that lead to oncogenic activation generate a constitutively active protein kinase by removal or interference with an N-terminal negative regulatory domain of the protein (Heidecker, G., et al. (1990) Mol. Cell. Biol. 10:2503-2512; Rapp, U. R., et al. (1987) in Oncogenes and cancer; S. A. Aaronson, J. Bishop, T. Sugimura, M. Terada, K. Toyoshima, and P. K. Vogt (ed). Japan Scientific Press, Tokyo). Microinjection into NIH 3T3 cells of oncogenically activated but not wild-type versions of the Raf-protein prepared with *Escherichia coli* expression vectors results in morphological transformation and stimulates DNA synthesis (Rapp, U. R., et al. (1987) in Oncogenes and cancer; S. A. Aaronson, J. Bishop, T. Sugimura, M. Terada, K. Toyoshima, and P. K. Vogt (ed.) Japan Scientific Press, Tokyo; Smith, M. R., et al (1990) Mol. Cell. Biol. 10:3828-3833). Activating mutants of B-Raf have been identified in a wide range of human cancers e.g. colon, ovarian, melanomas and sarcomas (Davies, H., et al. (2002), Nature 417 949-945. Published online Jun. 9, 2002, 10.1038/nature00766). The preponderant mutation is a single phosphomimetic substitution in the kinase activation domain (V599E), leading to constitutive kinase activity and transformation of NIH3T3 cells.

Thus, activated Raf-1 is an intracellular activator of cell growth. Raf-1 protein serine kinase in a candidate downstream effector of mitogen signal transduction, since Raf oncogenes overcome growth arrest resulting from a block of cellular ras activity due either to a cellular mutation (ras revertant cells) or microinjection of anti-ras antibodies (Rapp, U. R., et al. (1988) in The Oncogene Handbook, T. Curran, E. P. Reddy, and A. Skalka (ed.), Elsevier Science Publishers; The Netherlands, pp. 213-253; Smith, M. R., et al. (1986) Nature (London) 320:540-543).

c-Raf function is required for transformation by a variety of membrane-bound oncogenes and for growth stimulation by mitogens contained in serums (Smith, M. R., et al. (1986) Nature (London) 320:540-543). Raf-1 protein serine kinase activity is regulated by mitogens via phosphorylation (Morrison, D. K., et al. (1989) Cell 58:648-657), which also effects sub cellular distribution (Olah, Z., et al. (1991) Exp. Brain Res. 84:403; Rapp, U. R., et al. (1988) Cold Spring Harbor Sym. Quant. Biol. 53:173-184. Raf-1 activating growth factors include platelet-derived growth factor (PDGF) (Morrison, D. K., et al. (1988) Proc. Natl. Acad. Sci. USA 85:8855-8859), colony-stimulating factor (Baccarini, M., et al. (1990) EMBO J. 9:3649-3657), insulin (Blackshear, P. J., et al. (1990) J. Biol. Chem. 265:12115-12118), epidermal growth factor (EGF) (Morrison, R. K., et al. (1988) Proc. Natl. Acad. Sci. USA 85:8855-8859), interleukin 2 (Turner, B. C., et al (1991) Proc. Natl. Acad. Sci. USA 88:1227), and interleukin 3 and granulocytemacrophage colony-stimulating factor (Carroll, M. P., et al (1990) J. Biol. Chem. 265:19812-19817).

There are at least two independent pathways for Raf-1 activation by extracellular mitogens: one involving protein kinase C (PKC) and a second initiated by protein tyrosine kinases (Blackshear, P. J., et al. (1990) J. Biol. Chem. 265: 12131-12134; Kovacina, K. S., et al (1990) J. Biol. Chem. 265:12115-12118; Morrison, D. K., et al. (1988) Proc. Natl. Acad. Sci. USA 85:8855-8859; Siegel, J. N., et al (1990) J. Biol. Chem. 265:18472-18480; Turner, B. C., et al (1991) Proc. Natl. Acad. Sci. USA 88:1227). In either case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305-312).

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravasation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and/or (vii) deposition of basement membrane and recruitment of perivascular cells to newly formed vessels.

Normal angiogenesis is activated during tissue growth, from embryonic development through maturity, and then enters a period of relative quiescence during adulthood.

Normal angiogenesis is also activated during wound healing, and at certain stages of the female reproductive cycle. Inappropriate or pathological angiogenesis has been associated with several disease states including various retinopathies; ischemic disease; atherosclerosis; chronic inflammatory disorders; rheumatoid arthritis, and cancer. The role of angiogenesis in disease states is discussed, for instance, in Fan et al, Trends in Pharmacol Sci. 16:54 66; Shawver et al, DOT Vol. 2, No. 2 Feb. 1997; Folkman, 1995, Nature Medicine 1:27-31.

It has been proposed that various receptor-type tyrosine kinases, and the growth factors binding to them, play a role in angiogenesis, although some may promote angiogenesis indirectly (Mustonen and Alitalo, *J. Cell Biol.* 129:895-898, 1995). One of these receptor-type tyrosine kinases is foetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11-15, 1993). VEGF and KDR are a ligand-receptor pair which plays a vital role in the proliferation of vascular endothelial cells and the formation and sprouting of blood vessels, referred to as vasculogenesis and angiogenesis respectively. Angiogenesis is characterised by excessive activity of vascular endothelial growth factor (VEGF). VEGF actually consists of a family of ligands (Klagsburn and D'Amore, *Cytokine & Growth Factor Reviews* 7:259-270, 1996). VEGF binds the high affinity membrane-spanning tyrosine kinase receptor KDR and the related fms tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumour growth has been shown to be susceptible to the antiangiogenic effects of VEGF receptor antagonists (Kim et al., Nature 362, pp. 841-844, 1993).

Solid tumours can therefore be treated with tyrosine inhibitors since these tumours depend on angiogenesis for the formation of the blood vessels that are necessary to support their growth. These solid tumours include monocytic leukaemia, carcinomas of the brain, urogenital tract, lymphatic system, stomach, larynx and lung, including lung adenocarcinoma and small cell lung carcinoma. Further examples include carcinomas in which overexpression or activation of Raf-activating oncogenes (for example, K-ras, erb-B) is observed. Such carcinomas include pancreatic and breast carcinoma. Inhibitors of these tyrosine kinases are therefore suitable for the prevention and treatment of proliferative diseases caused by these enzymes. The angiogenic activity of VEGF is not limited to tumours. VEGF accounts for the angiogenic activity produced in or near the retina in diabetic retinopathy. This vascular growth in the retina leads to visual degeneration culminating in blindness. Ocular VEGF mRNA and protein levels are elevated by conditions such as retinal vein occlusion in primates and decreased $pO_2$ levels in mice that lead to neovascularisation. Intraocular injections of anti-VEGF monoclonal antibodies or VEGF receptor immunofusions inhibit ocular neovascularisation in both primate and rodent models. Irrespective of the cause of induction of VEGF in human diabetic retinopathy, inhibition of ocular VEGF is suitable for treating this disease.

Expression of VEGF is also significantly increased in hypoxic regions of animal and human tumours adjacent to areas of necrosis. In addition, VEGF is upregulated by the expression of the oncogenes Ras, Raf, Src and mutant p53 (all of which are relevant in combating cancer). Anti-VEGF monoclonal antibodies inhibit the growth of human tumours in nude mice. Although the same tumour cells continue to express VEGF in culture, the antibodies do not diminish their mitotic rate. Thus, tumour-derived VEGF does not function as an autocrine mitogenic factor. VEGF therefore contributes to tumour growth in vivo by promoting angiogenesis through its paracrine vascular endothelial cell chemotactic and mitogenic activities. These monoclonal antibodies also inhibit the growth of typically less well vascularised human colon carcinomas in athymic mice and decrease the number of tumours arising from inoculated cells.

The expression of a VEGF-binding construct of Flk-1, Flt-1, the mouse KDR receptor homologue truncated to eliminate the cytoplasmic tyrosine kinase domains but retaining a membrane anchor, in viruses virtually stops the growth of a transplantable glioblastoma in mice, presumably by the dominant negative mechanism of heterodimer formation with membrane-spanning endothelial cell VEGF receptors.

Embryonic stem cells, which normally grow as solid tumours in nude mice, do not produce detectable tumours if both VEGF alleles are knocked out. Taken together, these data indicate the role of VEGF in the growth of solid tumours. Inhibition of KDR or Flt-1 is involved in pathological angiogenesis, and these receptors are suitable for the treatment of diseases in which angiogenesis is part of the overall pathology, for example inflammation, diabetic retinal vascularisation, as well as various forms of cancer, since tumour growth is known to be dependent on angiogenesis (Weidner et al., N. Engl. J. Med., 324, pp. 1-8, 1991).

In cancer the growth of solid tumors has been shown to be angiogenesis dependent. (See Folkman, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Raf is involved in angiogenic processes. Endothelial growth factors (e.g. vascular endothelial growth factor VEGF or basic fibroblast growth factor bFGF) activates receptor tyrosine kinases (e.g. VEGFR-2) and signal through the Ras/Raf/Mek/Erk kinase cascade and protects endothelial cells from apoptosis (Alavi et al. (2003), Science 301, 94-96; Hood, J. D. et al. (2002), Science 296, 2404; Mikula, M. et al. (2001), EMBO J. 20, 1952; Hauser, M. et al. (2001), EMBO J. 20, 1940; Wojnowski et al. (1997), Nature Genet. 16, 293). Activation of VEGFR-2 by VEGF is a critical step in the signal transduction pathway that initiates tumor angiogenesis. VEGF expression may be constitutive to tumor cells and can also be upregulated in response to certain stimuli. One such stimulus is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, April 2000).

In cancer the growth of solid tumors has been shown to be angiogenesis dependent. (See Folkman, J., J. Nat'l. Cancer Inst., 1990, 82, 4-6.) Consequently, the targeting of pro-angiogenic pathways is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate or pathological angiogenesis (Pinedo, H. M. et al The Oncologist, Vol. 5, No. 90001, 1-2, April 2000). VEGFR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97-111; S. A. Courtneidge, Dev. Suppl., 1993, 57-64; J. A. Cooper, Semin. Cell Biol., 1994, 5(6)'377-387; R. F. Paulson, Semin. Immunol., 1995, 7(4), 267-277; A. C. Chan, Curr. Opin. Immunol., 1996, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al J. Cell Biol. 1995:129:895-898).

Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimulus is hypoxia, where VEGF expression is upregulated in both tumor and associated host tissues. The VEGF ligand activates VEGFR-2 by binding to its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, April 2000).

Angiopoietin 1 (Ang1), a ligand for the endothelium-specific receptor tyrosine kinase Tie-2 (or TIE-2) is a novel angiogenic factor (Davis et al, Cell, 1996, 87:1161-1169; Partanen et al, Mol. Cell. Biol, 12:1698-1707 (1992); U.S. Pat. Nos. 5,521,073; 5,879,672; 5,877,020; and 6,030,831). The acronym Tie (or TIE) represents "tyrosine kinase containing Ig and EGF homology domains". Tie is used to identify a class of receptor tyrosine kinases, which are exclusively expressed in vascular endothelial cells and early hemopoietic cells. Typically, Tie receptor kinases are characterized by the presence of an EGF-like domain and an immunoglobulin (IG) like domain, which consists of extracellular folding units, stabilized by intra-chain disulfide bonds (Partanen et al; Curr. Topics Microbiol. Immunol., 1999, 237:159-172). Unlike VEGF, which functions during the early stages of vascular development, Ang1 and its receptor Tie-2 function in the later stages of vascular development, i.e., during vascular remodeling (remodeling refers to regression of established vasculature and formation of new blood vessels) and maturation (Yancopoulos et al, Cell, 1998, 93:661-664; Peters, K. G., Circ. Res., 1998, 83(3):342-3; Suri et al, Cell 87, 1171-1180 (1996)).

Endothelial cells (EC) and pericytes (PCs) interact with and are responsible for the maturation, sprouting, bridging, and growth from existing vessels (Jain, Nat. Med. 2003 June; 9(6):685-93).

Ang1 is an agonist of Tie-2 and thus stabilizes or promotes endothelial cells and their formation, whereas Ang2 is an antagonist of Tie-2 and thus destabilizes endothelial cells and their formation. Tie-2 antagonizes VEGF driven EC proliferation. Otherwise ECs that interact with pericytes are stabilized and do not respond anymore to VEGF.

Tie-2 inhibitors will lead to vessel regression if VEGF level is low (not sufficient for stimulation) and VEGFR-2 is not activated.

Consequently, inhibition of Tie-2 would be expected to serve to disrupt interaction with pericytes and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Therefore, inhibition of Tie-2 and/or VEGFR-2 should prevent tumor angiogenesis and serve to retard or eradicate tumor growth. The receptor tyrosine kinases comprise a plurality of transmembrane receptors with varying biological activity. More than 20 different subfamilies of receptor tyrosine kinases have been identified. A tyrosine kinase-subfamily, named HER subfamily, consists of EGFR, HER2, HER3 and HER4. To the ligands of this receptor-subfamily belong the epithelial growth factor, TGF-α, Amphiregulin, HB-EGF, Betacellulin and Heregulin. The insulin-subfamily, to which INS-R, IGF-IR and IR-R are counted, is a further subfamily of the receptor tyrosine kinases. The PDGF subfamily comprises the PDGF-α- and -β-receptor, CSFIR, c-kit and FLK-II. Moreover, there is the FLK-family, which consists of the kinaseinsertdomaine receptor (KDR), the fetal liver kinase-1 (FLK-1), the fetal liver kinase-4 (FLK-4) and the fms-tyrosine kinase-1 (flt-1). Because of the similarities between the PDGF- and FLK-families, both groups are usually discussed commonly. For a more detailed dispassion of the receptor tyrosine kinases see the publication of Plowman et al., DN & P 7(6):334-339, 1994, the disclosure of which is incorporated herein by reference.

The cytosolic tyrosine kinases also consist of a plurality of subfamilies, such as Src, Frk, Btk, Csk, Abl, Zap70, Fes/Fps, Fak, Jak, Ack, and LIMK. Every of the subfamilies is a further divided into different receptors. For example, the Src subfamily is one of the biggest families. It contains Src, Yes, Fyn, Lyn, Lck, Blk, Hck, Fgr und Yrk. The Src enzyme subfamily is discussed in connection with oncogenesis. For a more detailed discussion of the cytosolic tyrosine kinases, see the publication of Bolen *Oncogene,* 8:2025-2031 (1993), the disclosure of which is incorporated herein by reference.

The receptor tyrosine kinases as well as the cytosolic tyrosine kinases are involved in the signal transduction pathways is of the cell, which are relevant for various diseases, such as cancer, psoriasis, hyper immuno reactions and auto immune diseases.

Of the three PTK (protein tyrosine kinases) receptors for VEGFR identified VEGFR-1 (Flt-1); VEGRF-2 (Flk-1 or KDR) and VEGFR-3 (Flt-4), VEGFR-2 is of peculiar interest.

A preferred aspect of the invention therefor relates to methods for the regulation, modulation and/or or inhibition of VEGFR-2, for the prevention and/or treatment of diseases in connection with unregulated or disturbed VEGFR-2-activity.

Also of great interest is the stress activated protein kinase (SAPK) pathway. The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. As disclosed herein, agents that inhibit SAPK activity in a cell prevent DNA repair and sensitize the cell to those cancer therapeutic modalities that act by inducing DNA damage, such as ionizing radiation; chemical agents that crosslink or otherwise directly damage DNA including cis-platinum and alkylating agents such as N-methyl-N'-nitro-N-nitroso-guanidine (MNNG) and methylmethanesulphonate (MMS); and agents that interfere with DNA synthesis including DNA chain terminating agents such as 1-β-arabinofuranosylcytosine (AraC), topoisomerase inhibitors such as camptothecin, and nucleoside analogs or precursors of such analogs such as methotrexate (MTX) and 5-fluorouracil (5-FU).

Preferably, the SAPK pathway is also involved in the mitogenic response of certain cells, including cancer cells. For example, human A549 tumor cells, which express an EGF receptor on their cell surface, respond mitogenically to EGF. However, the mitogenic response, but not basal growth, is inhibited when the SAPK pathway is inhibited by expressing a dominant negative c-jun mutant in the cells. Thus, in addition to sensitizing tumor cells to a cancer therapeutic modality, inhibition of the SAPK pathway also can block mitogenesis of tumor cells, for example, in response to an autocrine growth factor, thereby providing a therapeutic advantage to an individual treated with a cancer therapeutic modality. In addition, the SAPK pathway can lead to activation of various transcription factors, some of which are involved in cell growth and proliferation.

The SAPK pathway is activated in response to genotoxic agents such as ultraviolet radiation and various cancer therapeutic modalities (see, for example, Derijard et al., *Cell* 76:1025-1037 (1994); Adler et al., *J. Biol. Chem.* 270:26071-26077 (1995); van Dam et al, *EMBO J.* 14:1798-1811 (1995); Kharabanda et al., *Proc. Natl. Acad. Sci., USA* 93:6898-6901 (1996)). SAPK (JNK) phosphorylates c-jun at serine residues 63 and 73 (Smeal et al., *Nature* 354:494-496 (1991)). In turn, working backwards from c-jun activation in the SAPK pathway, SAPK is activated by phosphorylation of a SAPK kinase (SAPKK; JNKK), which, itself, is activated by phosphorylation of a SAPKK kinase (SAPKKK; JNKKK; also called MEKK1 and referred to herein as "MEKK1;" GenBank Accession No. U29671, which is incorporated herein by reference; see, also, U.S. Pat. No. 5,405,941, which is incorporated herein by reference). Additional steps of the pathway precede the activation of MEKK1 (Liu et al., *Cell* 87:565-576 (1996)) and, as discussed below, MEKK1 also acts as a branch point for a second pathway.

Various SAPK's, including SAPK1 (JNK; SAPK1α1; GenBank Accession No. 226318; see, also, U.S. Pat. No. 5,534,426, which is incorporated herein by reference), SAPK2 (SAPK2α1; U34821) and SAPK3 (SAPK3α1; U34820), and related isozymes, SAPK1α2 (U34822), SAPK1β1 (U35004), SAPK1β2 (U35005), SAPK2β1 (U35002), SAPK2β2 (U35003) and SAPK3α2 (U34819), each of which is incorporated herein by reference, have been described (see Gupta et al., *EMBO J.* 15:2760-2770 (1996); see, also, Cuenda et al., *EMBO J.* 16:295-305 (1997)). Activation of one or more SAPK's in a cell is associated with the induction of expression of various genes involved in DNA repair and cell survival following a stress, including the genes encoding c-jun (Chu et al., *Mol. Endocrinol.* 8:59 (1994)), p21 (Waf1/Cip1) (El-Deiry et al., *Cancer Res.* 55:2910 (1995)), ATF2, ATF3 (Gately et al., *Brit. J. Cancer* 70:1102 (1994)), PCNA (Huang et al., *Mol. Cell. Biol.* 14:4233 (1994)), cyclin-A, cyclin-D1 (Herbert et al., *Oncogene* 9:1295 (1994)), cyclin-G and GADD153 (Luethy and Holbrook, *Cancer Res.* 54:1902S (1994); Gately et al., supra, 1994).

Accordingly, a composition that inhibits a SAPK pathway as disclosed herein can be useful to inhibit proliferation, growth or DNA repair in cancer cells, thereby increasing the likelihood that cancer cells containing such damage will die.

p38 (or P38) (also CSBP or RK) is a serine/threonine mitogen-activated protein kinase (MAPK) that has been shown to regulate pro-inflammatory cytokines. p38 was first identified as a kinase which became tyrosine phosphorylated in mouse monocytes following treatment with lipopolysaccharide (LPS). A link between p38 and the response of cells to cytokines was first established by Saklatvala J., et al., *Cell,* 78: 1039-1049 (1994), who showed that IL-1 activates a protein kinase cascade that results in the phosphorylation of the small heat shock protein, Hsp27, probably by mitogen-activated protein activated protein kinase 2 (MAPKAP kinase-2). Analysis of peptide sequences derived from the purified kinase indicated that it was related to the p38 MAPK activated by LPS in mouse monocytes, Han, J., et al., *Science,* 265: 808-811 (1994). At the same time it was shown that p38 MAPK was itself activated by an upstream kinase in response to a variety of cellular stresses, including exposure to UV radiation and osmotic shock, and the identity of the kinase that directly phosphorylates Hsp27 was confirmed as MAP-KAP kinase-2, Rouse, J., et al., *Cell,* 78: 1027-1037 (1994). Subsequently, workers at SmithKline Beecham showed that p38 MAPK was the molecular target of a series of pyridinylimidazole compounds that inhibited the production of TNF from LPS-challenged human monocytes, Lee, J., et al., *Nature,* 372: 739-746. This was a key discovery and has led to the development of a number of selective inhibitors of p38 MAPK and the elucidation of its role in cytokine signaling.

It is now known that multiple forms of p38 MAPK ((α, β, γ, δ), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNF-α p38 functions by phosphorylating downstream substrates that include other kinases and transcription factors. Agents that inhibit p38 kinase have been shown to block the production of cytokines including but not limited to TNF-α, IL-6, IL-8 and IL-1β in vitro and in vivo models Adams, J. L., et al., *Progress in Medicinal Chemistry*, 38: 1-60 (2001).

Peripheral blood monocytes (PBMCs) have been shown to express and secrete pro-inflammatory cytokines when stimulated with lipopolysaccharide (LPS) in vitro. p38 inhibitors efficiently block this effect when PBMCs are pretreated with such compounds prior to stimulation with LPS. Lee, J. C., et al., Int. *J. Immunopharmacol.*, 10: 835-843 (1988). The efficacy of p38 inhibitors in animal models of inflammatory disease has prompted an investigation of the underlying mechanism(s) which could account for the effect of these inhibitors. The role of p38 in the response of cells to IL-1 and TNF has been investigated in a number of cells systems relevant to the inflammatory response using a pyridinyl imidazole inhibitor: endothelial cells and IL-8, Hashimoto, S., et al., *J. Pharmacol. Exp. Ther.*, 293: 370-375 (2001), fibroblasts and IL-6/GM-CSF/PGE2 Beyaert, R., et al., *EMBO J.*, 15: 1914-1923 (1996), neutrophils and IL-8 Albanyan, E. A., et al., *Infect Immun.*, 68: 2053-2060 (2000) macrophages and IL-1 Caivano, M. and Cohen, P., *J. Immunol.*, 164: 3018-3025 (2000), and smooth muscle cells and RANTES Maruoka, S., et al., *Am. J. Respir. Crit. Care Med.*, 161: 659-668 (1999). The destructive effects of many disease states are caused by the over production of pro-inflammatory cytokines. The ability of p38 inhibitors to regulate this overproduction makes them excellent candidates for disease modifying agents. Accordingly, p38 inhibitors preferably are useful for the treatment of inflammation, osteoarthritis, rheumatoid arthritis, cancer, autoimmune diseases, and for the treatment of other cytokine mediated diseases.

Mice with a targeted disruption in the Braf gene die of vascular defects during development (Wojnowski, L. et al. 1997, Nature genetics 16, page 293-296). These mice show defects in the formation of the vascular system and in angiogenesis e.g. enlarged blood vessels and increased apoptotic death of differentiated endothelial cells.

For the identification of a signal transduction pathway and the detection of cross talks with other signaling pathways suitable models or model systems have been generated by various scientists, for example cell culture models (e.g. Khwaja et al., EMBO, 1997, 16, 2783-93) and transgenic animal models (e.g. White et al., Oncogene, 2001, 20, 7064-7072). For the examination of particular steps in the signal transduction cascade, interfering compounds can be used for signal modulation (e.g. Stephens et al., Biochemical J., 2000, 351, 95-105). The compounds according to the invention may also be useful as reagents for the examination of kinase dependent signal transduction pathways in animal and/or cell culture models or any of the clinical disorders listed throughout this application.

The measurement of kinase activity is a well known technique feasible for each person skilled in the art. Generic test systems for kinase activity detection with substrates, for example histone (e.g. Alessi et al., FEBS Lett. 1996, 399, 3, page 333-8) or myelin basic protein are well described in the literature (e.g. Campos-González, R. and Glenney, Jr., J. R. 1992 J. Biol. Chem. 267, Page 14535).

For the identification of kinase inhibitors various assay systems are available (see for example Walters et al., Nature Drug Discovery 2003, 2; page 259-266). For example, in scintillation proximity assays (e.g. Sorg et al., J. of. Biomolecular Screening, 2002, 7, 11-19) or flashplate assays the radioactive phosphorylation of a protein or peptide as substrate with γATP can be measured. In the presence of an inhibitory compound no signal or a decreased radioactive signal is detectable. Furthermore homogeneous time-resolved fluorescence resonance energy transfer (HTR-FRET), and fluorescence polarization (FP) technologies are useful for assay methods (for example Sills et al., J. of Biomolecular Screening, 2002, 191-214). Other non-radioactive ELISA based assay methods use specific phospho-antibodies (AB). The phospho-AB binds only the phosphorylated substrate. This binding is detectable with a secondary peroxidase conjugated antibody, measured for example by chemiluminescence (for example Ross et al., Biochem. J., 2002, 366, 977-981).

WO 02/44156 describes benzimidazole derivatives as Tie-2 and/or VEGFR2 inhibitors. WO 99/32436 describes substituted phenyl urea derivatives as Raf-kinase inhibitors. WO 02/062763 and WO 02/085857 describe quinoline-, isoquinoline- und pyridyl or phenyl urea derivatives as raf kinase inhibitors. Hetero aryl ureas are described in WO 02/85859 as p38 kinase inhibitors. WO 00/42012 and WO 00/41698 describe ω-carboxyaryl-diphenyl-ureas as raf kinase inhibitors and p38 kinase inhibitors, respectively. Furthermore aryl and heteroaryl substituted ureas are described in WO 99/32455 as raf kinase inhibitors and in WO 99/32110 as p38 kinase inhibitors, respectively. Further diphenyl urea derivatives are known from WO 99/32463 and WO 99/32111.

The present invention provides compounds generally described as bisarylurea derivatives, including both aryl and/or heteroaryl derivatives which are preferably kinase inhibitors and more preferably inhibitors of one or more kinases as defined herein. The inhibitors preferably are useful in pharmaceutical compositions for human or veterinary use where inhibition of of one or more kinase pathway is indicated, e.g., in the treatment of tumors and/or cancerous cell growth mediated by one or more kinases. In particular, the compounds preferably are useful in the treatment of human or animal solid cancers, e.g. murine cancer, since the progression of these cancers is dependent upon the respective signal transduction cascades and therefore susceptible to treatment by interruption of one or more of said cascades, i.e., by inhibiting one or more of said kinases. Accordingly, the compound of formula I or a pharmaceutically acceptable salt thereof can be administered for the treatment of diseases mediated by one or more kinase pathways, especially cancers, preferably solid cancers, such as, for example, carcinomas (e.g., of the lungs, pancreas, thyroid, bladder or colon), myeloid disorders (e.g., myeloid leukemia) or adenomas (e.g., villous colon adenoma), pathological angiogenesis and metastatic cell migration. Furthermore the compounds preferably are useful in the treatment of, inter alia, complement activation dependent chronic inflammation (Niculescu et al. (2002) Immunol. Res., 24:191-199) and HIV-1 (human immunodeficiency virus type1) induced immunodeficiency (Popik et al. (1998) J Virol, 72: 6406-6413) and infection disease, Influenza A virus (Pleschka, S. et al. (2001), Nat. Cell. Biol, 3(3):301-5) and *Helicobacter pylori* infection (Wessler, S. et al. (2002), FASEB J., 16(3): 417-9).

Therefore, subject of the present invention are bisarylurea derivatives of formula I $$(R^7)_g \underset{(R^8)_p}{\diagdown} Ar^1 \underset{H}{\diagdown} \overset{Y}{\underset{\|}{C}} \underset{H}{\diagdown} Ar^2 \underset{(R^9)_q}{\diagup} (R^4)_z \qquad I$$

wherein
$Ar^1$, $Ar^2$ are selected independently from one another from unsaturated or aromatic cyclic hydrocarbons containing 5 to 14 carbon atoms and unsaturated or aromatic heterocyclic residues containing 2 to 10 carbon atoms and one or more heteroatoms, preferably 1 to 5 heteroatoms, independently selected from N, O and S, $R^4$ is independently selected from residues of the formula $(X—Ar^3)_\alpha—(R^{10})_r$, wherein $Ar^3$ is independently selected from the meanings given for $Ar^1$ and/or $Ar^2$, $\alpha$ is 0, 1 or 2, $R^{10}$ is independently selected from the meanings given for $R^8$ and $R^9$, and r is 0, 1, 2, 3, 4 or 5;

z is 0, 1, 2, 3, 4 or 5, $R^7$ is a nitrogen containing heterocylic moiety, directly bound to $Ar^1$ via a nitrogen atom, said nitrogen containing heterocylic moiety being independently selected from $Het^1$, $Het^2$ and $Het^3$, wherein $Het^1$ is an unsaturated or aromatic heterocyclic residue comprising 5, 6 or 7 ring atoms which contains 1 to 4 nitrogen atoms and optionally 1 or 2 additional heteroatoms selected from O and S, whereby said unsaturated or aromatic heterocyclic residue is unsubstituted or substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $Het^2$ is a saturated, unsaturated or aromatic bicyclic residue comprising 3 to 10 carbon atoms, 1 to 4 nitrogen atoms and optionally 1 or 2 additional heteroatoms selected from O and S, whereby said bicyclic residue is unsubstituted or substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $Het^3$ is a saturated monocyclic residue comprising 2 to 6 carbon atoms, 1 to 4 nitrogen atoms and optionally 1 or 2 additional heteroatoms selected from O and S, whereby said monocyclic residue is substituted by one or more substituents, selected from a group consisting of =O, =S, =N—$R^{14}$, and optionally substituted by one or more substituents, selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $R^3$ and $R^9$ are independently selected from a group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_n NR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_k OR^{12}$, $(CH_2)_nCOOR^{13}$, $(CH_2)_nCOR^{13}$, $(CH_2)_n CONR^{11}R^{12}$, $(CH_2)_nNR^{11}COR^{13}$, $(CH_2)_n NR^{11}CONR^{11}R^{12}$, $(CH_2)_nNR^{11}SO_2A$, $(CH_2)_n SO_2NR^{11}R^{12}$, $(CH_2)_nS(O)_uNR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, CH=N— OA, $CH_2CH=N$—OA, $(CH_2)_nNHOA$, $(CH_2)_nCH=N—R^{11}$, $(CH_2)_nOC(O)NR^{11}R^{12}$, $(CH_2)_nNR^{11}COOR^{13}$, $(CH_2)_n$ $N(R^{11})CH_2CH_2OR^{13}$, $(CH_2)_nN(R^{11}) CH_2CH_2OCF_3$, $(CH_2)_nN(R^{11})C(R^{13})HCOOR^{12}$, $(CH_2)_nN(R^{11})C(R^{13})HCOR^{11}$, $(CH_2)_nN(R^{11})CH_2CH_2N(R^{12}) CH_2COOR^{11}$, $(CH_2)_nN(R^{11})CH_2CH_2NR^{11}R^{12}$, CH=CHCOOR$^{13}$, CH=CHCH$_2$NR$^{11}$R$^{12}$, CH=CHCH$_2$OR$^{13}$, $(CH_2)_nN(COOR^{13})COOR^{14}$, $(CH_2)_nN(CONH_2)COOR^{13}$, $(CH_2)_n N(CONH_2)CONH_2$, $(CH_2)_nN(CH_2COOR^{13})COOR^{14}$, $(CH_2)_nN(CH_2CONH_2)COOR^{13}$ $(CH_2)_nN(CH_2CONH_2) CONH_2$, $(CH_2)_nCHR^{13}COR^{14}$, $(CH_2)_nCHR^{13}COOR^{14}$, $(CH_2)_nCHR^{13}CH_2OR^{14}$, $(CH_2)_nOCN$ $(CH_2)_nNCO$, $Het^9$, $OHet^9$, $N(R^{11})Het^9$, $(CR^5R^6)_kHet^9$, $O(CR^5R^6)_kHet^9$, $N(R^{11})(CR^5R^6)_kHet^9$, $(CR^5R^6)_kNR^{11}R^{12}$, $(CR^5R^6)_kOR^{13}$, $O(CR^5R^6)_kNR^{11}R^{12}$, $NR^{11}(CR^5R^6)_kNR^{11}R^{12}$, $O(CR^5R^6)_k$ $R^{13}$, $NR^{11}(CR^5R^6)_kR^{13}$, $O(CR^5R^6)_kOR^{13}$, $NR^{11}(CR^5R^6)_kOR^{13}$, wherein $R^5$, $R^6$ are in each case independently from one another selected from H and A, $R^{11}$, $R^{12}$ are independently selected from a group consisting of H, A, $(CH_2)_mAr^7$ and $(CH_2)_mHet^9$, or in $NR^{11}R^{12}$, $R^{11}$ and $R^{12}$ form, together with the N-atom they are bound to, a 5-, 6- or 7-membered heterocyclus which optionally contains 1 or 2 additional hetero atoms, selected from N, O and S; whereby said heterocyclic residue optionally is substituted by one or more substituent, selected from A, $R^{13}$, =O, =S and =N—$R^{14}$, $R^{13}R^{14}$ are independently selected from a group consisting of H, Hal, A, $(CH_2)_mAr^8$ and $(CH_2)_mHet^9$, A is selected from the group consisting of alkyl, alkenyl, cycloalkyl, alkylenecycloalkyl, alkoxy, alkoxyalkyl and saturated heterocyclyl, preferably from the group consisting of alkyl, alkenyl, cycloalkyl, alkylenecycloalkyl, alkoxy and alkoxyalkyl, $Ar^7$, $Ar^8$ are independently from one another aromatic hydrocarbon residues comprising 5 to 12 and preferably 5 to 10 carbon atoms which are optionally substituted by one or more substituents, selected from a group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $Het^9$ is a saturated, unsaturated or aromatic heterocyclic residue which preferably contains 1 to 3 heteroatoms, more preferably 1 or 2 heteroatoms, the heteroatoms being preferably selected from N, O and S, more preferably from N and O; whereby said heterocyclic residue is optionally substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $R^{15}$, $R^{16}$ are independently selected from a group consisting of H, A, and $(CH_2)_mAr^6$, wherein $Ar^6$ is a 5- or 6-membered aromatic hydrocarbon which is optionally substituted by one or more substituents selected from a group consisting of methyl, ethyl, propyl, 2-propyl, tert.-butyl, Hal, CN, OH, $NH_2$ and $CF_3$, k, n and m are independently of one another 0, 1, 2, 3, 4, or 5, X represents a bond or is $(CR^{11}R^{12})_h$, or $(CHR^{11})_h$-Q'— $(CHR^{12})_i$, wherein Q' is selected from a group consisting of O, S, N—$R^{15}$, $(CHal_2)_j$, (O—$CHR^{18})_j$, $(CHR^{18}—O)_j$, $CR^{18}$=$CR^{19}$, (O—$CHR^{18}CHR^{19})_j$, $(CHR^{18}CHR^{19}—O)_j$, C=O, C=S, C=$NR^{15}$CH(OR$^{15}$), $C(OR^{15})(OR^{20})$, C(=O)O, OC(=O), OC(=O)O, C(=O)N(R$^{15}$), N(R$^{15}$)C(=O), OC(=O)N(R$^{15}$), N(R$^{15}$)C(=O)O, CH=N—O, CH=N—NR$^{15}$, OC(O)NR$^{15}$, NR$^{15}$C(O)O, S=O, $SO_2$, $SO_2NR^{15}$ and $NR^{15}SO_2$, wherein h, i are independently from each other 0, 1, 2, 3, 4, 5, or 6, and j is 1, 2, 3, 4, 5, or 6, Y is selected from O, S, $NR^{21}$, $C(R^{22})$—$NO_2$, $C(R^{22})$—CN and $C(CN)_2$, wherein $R^{21}$ is independently selected from the meanings given for $R^{13}$, $R^{14}$ and $R^{22}$ is independently selected from the meanings given for $R^{11}$, $R^{12}$, g is 1, 2 or 3, preferably 1 or 2, p is 0, 1, 2, 3, 4 or 5, q is 0, 1, 2, 3 or 4, preferably 0, 1 or 2,
u is 0, 1, 2 or 3, preferably 0, 1 or 2,
and
Hal is independently selected from a group consisting of F, Cl, Br and I;
and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Preferably, the compound according to the invention is other than 4-(4-{3-[4-(2,5-Dioxo-pyrrolidin-1-yl)-3-trifluoromethyl-phenyl]-ureido}-phenoxy)-pyridine-2-carboxylic acid methylamide, and preferably other than the pharmaceutically acceptable derivatives, solvates, salts and stereoisomers thereof.

In compounds according to the invention, $Het^3$ is preferably other than unsubstituted and/or substituted succinimidyl.

In compounds according to the invention, $Het^3$ is more preferably other than unsubstituted succinimidyl.

In compounds according to the invention, $R^7$, $R^8$ and/or $R^9$ are preferably other than unsubstituted and/or substituted succinimidyl.

In compounds according to the invention, $R^7$, $R^8$ and/or $R^9$ are preferably other than unsubstituted succinimidyl.

In compounds according to the invention, $R^7$, $R^8$, $R^9$ and/or $Het^9$ are more preferably other than unsubstituted and/or substituted succinimidyl.

In compounds according to the invention, $R^7$, $R^8$, $R^9$ and/or $Het^9$ are more preferably other than unsubstituted succinimidyl.

In this respect, the term succinimidyl preferably refers to succinimidoyl, 2,5-Dioxo-pyrrolidinyl and/or 2,5-Pyrrolidindionyl, and more preferably to succinimidoyl, succinimid-1-yl, 2,5-Dioxo-pyrrolidin-1-yl and/or 2,5-Pyrrolidindion-1-yl. In this respect, the terms succinimid-1-yl, 2,5-Dioxo-pyrrolidin-1-yl and/or 2,5-Pyrrolidindion-1-yl preferably are to be regarded as equivalent to the terms succinimide-1-yl, 2,5-Dioxo-pyrrolidine-1-yl and/or 2,5-Pyrrolidindione-1-yl, respectively. Also in this respect, the terms succinimidoyl and succinimido-1-yl preferably are to be regarded as equivalent to the terms succinimidyl and succinimid-1-yl, respectively.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" preferably refers to a straight or branched chain hydrocarbon having from one to twelve carbon atoms, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$-$C_6$ alkyl" preferably refers to an alkyl group as defined above containing at least 1, and at most 6, carbon atoms. Examples of branched or straight chained "$C_1$-$C_6$ alkyl" groups useful in the present invention include, but are not limited to, methyl, ethyl, n-propyl, isopropyl, isobutyl, n-butyl, t-butyl, n-pentyl and isopentyl.

As used herein, the term "alkylene" preferably refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl, optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene and the like.

As used herein, the term "$C_1$-$C_6$ alkylene" preferably refers to an alkylene group, as defined above, which contains at least 1, and at most 6, carbon atoms respectively. Examples of "$C_1$-$C_6$ alkylene" groups useful in the present invention include, but are not limited to, methylene, ethylene and n-Propylene.

As used herein, the term "halogen" or "hal" preferably refers to fluorine (F), chlorine (Cl), bromine (Br) or iodine (I).

As used herein, the term "$C_1$-$C_6$ haloalkyl" preferably refers to an alkyl group as defined above containing at least 1, and at most 6, carbon atoms substituted with at least one halogen, halogen being as defined herein. Examples of branched or straight chained "$C_1$-$C_6$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "cycloalkyl" or "$C_3$-$C_7$ cycloalkyl" preferably refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups include, but are not limited to, cyclopropyl, cyclobutyl, cyclopentyl, cyclohexyl and cycloheptyl. The term "cycloalkyl", as used herein preferably also includes saturated heterocyclic groups, which are preferably selected from the cycloalkyl-groups as defined above, wherein one or two carbon atoms are replaced by hetero atoms, selected from the group consisting of O, N and S, which optionally is substituted by one or more substituents, preferably selected from alkyl, =O, =S and substituted or unsubstituted imino groups.

As used herein, the term "$C_3$-$C_7$ cycloalkylene" preferably refers to a non-aromatic alicyclic divalent hydrocarbon radical having from three to seven carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" preferably refers to a three to twelve-membered heterocyclic ring, optionally having one or more degrees of unsaturation and optionally containing one or more heteroatomic substitutions selected from S, SO, SO$_2$, O or N, optionally substituted with substituents selected from the group consisting of $C_1$-$C_6$ alkyl, $C_1$-$C_6$ haloalkyl, $C_1$-$C_6$ alkoxy, $C_1$-$C_6$ alkylsulfanyl, $C_1$-$C_6$ haloalkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, and the like.

As used herein, the term "heterocyclylene" preferably refers to a three to twelve-membered heterocyclic ring diradical optionally having one or more degrees of unsaturation and optionally containing one or more heteroatoms selected from S, SO, SO$_2$, O or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" preferably refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "aryl" groups include, but are not limited to Phenyl, 2-naphthyl, 1-naphthyl, biphenyl, as well as substituted derivatives thereof. As used herein, the term "arylene" preferably refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of "arylene" include, but are not limited to benzene-1,4-diyl, naphthalene-1,8-diyl, anthracene-1,4-diyl, and the like.

As used herein, the term "aralkyl" preferably refers to an aryl or heteroaryl group, as defined herein, attached through a $C_1$-$C_6$ alkyl linker, wherein $C_1$-$C_6$ alkyl is as defined herein. Examples of "aralkyl" include, but are not limited to, benzyl, phenylpropyl, 2-pyridylmethyl, 3-isoxazolylmethyl, 5-methyl-3-isoxazolylmethyl and 2-imidazolylethyl.

As used herein, the term "heteroaryl" preferably refers to a monocyclic five to seven-membered aromatic ring, or to a fused bicyclic aromatic ring system comprising two of such monocyclic five to seven-membered aromatic rings. These hetroaryl rings contain one or more nitrogen, sulfur and/or oxygen heteroatoms, where N-Oxides and sulfur Oxides and dioxides are permissible heteroatom substitutions and may be optionally substituted with up to three members selected from a group consisting of $C_1$-$C_6$ alkyl, $C_1$-$C_6$ haloalkyl, $C_1$-$C_6$ alkoxy, $C_1$-$C_6$ alkylsulfanyl, $C_1$-$C_6$ haloalkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" preferably refers to a five- to seven-membered aromatic ring diradical, or to a polycyclic heterocyclic aromatic ring diradical, containing one or more nitrogen, oxygen, or sulfur heteroatoms, where N-Oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" preferably refers to the group $R_aO$—, where $R_a$ is alkyl as defined above and the term "$C_1$-$C_6$ alkoxy" preferably refers to an alkoxy group as defined herein wherein the alkyl moiety contains at least 1 and at most 6 carbon atoms. Exemplary $C_1$-$C_6$ alkoxy groups useful in the present invention include, but are not limited to methoxy, ethoxy, n-propoxy, isopropoxy, n-butoxy and t-butoxy.

As used herein, the term "haloalkoxy" preferably refers to the group $R_aO$—, where $R_a$ is haloalkyl as defined above and the term "$C_1$-$C_6$ haloalkoxy" preferably refers to an haloalkoxy group as defined herein wherein the haloalkyl moiety contains at least 1 and at most 6 carbon atoms. Exemplary $C_1$-$C_6$ haloalkoxy groups useful in the present invention include, but are not limited to, methoxy, ethoxy, n-propoxy, isopropoxy, n-butoxy and t-butoxy substituted with one or more halo groups, for instance trifluoromethoxy.

As used herein the term "aralkoxy" preferably refers to the group $R_C R_B O$—, where $R_B$ is alkyl and $R_C$ is aryl as defined above.

As used herein the term "aryloxy" preferably refers to the group $R_C O$—, where $R_C$ is aryl as defined above.

As used herein, the term "alkylsulfanyl" preferably refers to the group $R_A S$—, where $R_A$ is alkyl as defined above and the term "$C_1$-$C_6$ alkylsulfanyl" preferably refers to an alkylsulfanyl group as defined herein wherein the alkyl moiety contains at least 1 and at most 6 carbon atoms.

As used herein, the term "haloalkylsulfanyl" preferably refers to the group $R_D S$—, where $R_D$ is haloalkyl as defined above and the term "$C_1$-$C_6$ haloalkylsulfanyl" preferably refers to a haloalkylsulfanyl group as defined herein wherein the alkyl moiety contains at least 1 and at most 6 carbon atoms.

As used herein, the term "alkylsulfenyl" preferably refers to the group $R_A S(O)$—, where $R_A$ is alkyl as defined above and the term "$C_1$-$C_6$ alkylsulfenyl" preferably refers to an alkylsulfenyl group as defined herein wherein the alkyl moiety contains at least 1 and at most 6 carbon atoms.

As used herein, the term "alkylsulfonyl" preferably refers to the group $R_A SO_2$—, where $R_A$ is alkyl as defined above and the term "$C_1$-$C_6$ alkylsulfonyl" preferably refers to an alkylsulfonyl group as defined herein wherein the alkyl moiety contains at least 1 and at most 6 carbon atoms.

As used herein, the term "oxo" preferably refers to the group =O.

As used herein, the term "mercapto" preferably refers to the group —SH.

s used herein, the term "carboxy" preferably refers to the group —COOH.

As used herein, the term "cyano" preferably refers to the group —CN.

As used herein, the term "cyanoalkyl" preferably refers to the group —$R_B$CN, wherein $R_B$ is alkylen as defined above. Exemplary "cyanoalkyl" groups useful in the present invention include, but are not limited to, cyanomethyl, cyanoethyl and cyanoisopropyl.

As used herein, the term "aminosulfonyl" preferably refers to the group —$SO_2NH_2$.

As used herein, the term "carbamoyl" preferably refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$—.

As used herein, the term "acyl" preferably refers to the group $R_F C(O)$—, where $R_F$ is alkyl, cycloalkyl or heterocyclyl as defined herein.

As used herein, the term "aroyl" preferably refers to the group $R_C C(O)$—, where $R_C$ is aryl as defined herein.

As used herein, the term "heteroaroyl" preferably refers to the group $R_E C(O)$—where $R_E$ is heteroaryl as defined herein.

As used herein, the term "alkoxycarbonyl" preferably refers to the group $R_A OC(O)$—, where $R_A$ is alkyl as defined herein.

As used herein, the term "acyloxy" preferably refers to the group $R_F C(O)O$—, where $R_F$ is alkyl, cycloalkyl, or heterocyclyl as defined herein.

As used herein, the term "aroyloxy" preferably refers to the group $R_C C(O)O$—, where $R_C$ is aryl as defined herein.

As used herein, the term "heteroaroyloxy" preferably refers to the group $R_E C(O)O$—, where $R_E$ is heteroaryl as defined herein.

As used herein, the term "carbonyl" or "carbonyl moiety" preferably refers to the group C=O.

As used herein, the term "thiocarbonyl" or "thiocarbonyl moiety" preferably refers to the group C=S.

As used herein, the term "amino", "amino group" or "amino moiety" preferably refers to the group $NR_G R_{G'}$, wherein $R_G$ and $R_{G'}$ are preferably selected, independently from one another, from the group consisting of hydrogen, halogen, alkyl, haloalkyl, alkenyl, cycloalkyl, alkylenecycloalkyl, cyanoalkyl, aryl, aralkyl, heteroaryl, acyl and aroyl. If both $R_G$ and $R_{G'}$ are hydrogen, $NR_G R_{G'}$ is also referred to as "unsubstituted amino moiety" or "unsubstituted amino group". If $R_G$ and/or $R_{G'}$ are other than hydrogen, $NR_G R_{G'}$ is also referred to as "substituted amino moiety" or "substituted amino group".

As used herein, the term "imino" or "imino moiety" preferably refers to the group C=$NR_G$, wherein $R_G$ is preferably selected from the group consisting of hydrogen, halogen, alkyl, haloalkyl, alkenyl, cycloalkyl, alkylenecycloalkyl, cyanoalkyl, aryl, aralkyl, heteroaryl, acyl and aroyl. If $R_G$ is hydrogen, C=$NR_G$ is also referred to as "unsubstituted imino moiety". If $R_G$ is a residue other than hydrogen, C=$NR_G$ is also referred to as "substituted imino moiety".

As used herein, the term "unsaturated" preferably means ethylenically unsaturated.

As used herein, the terms "group", "residue" and "radical" or "groups", "residues" and "radicals" are usually used as synonyms, respectively, as it is common practice in the art.

As used herein, the term "optionally" means that the subsequently described event(s) may or may not occur, and includes both event(s), which occur, and events that do not occur.

As used herein, the term "physiologically functional derivative" preferably refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives. Further preferred examples of physiologically functional derivatives or pharmaceutically acceptable derivatives in this respect are prodrugs and/or labelled derivatives of compounds according to the invention. Suitable prodrugs and labelled derivatives of compounds according to the invention can be obtained according to methods known in the art.

As used herein, the term "solvate" preferably refers to a complex of variable stoichiometry formed by a solute (in this invention, a compound of formula I or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" preferably refers to substitution with the named substituent or substituents, multiple degrees of substitution being allowed unless otherwise stated.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, especially mixtures of enantiomers, as well as purified stereoisomers, especially purified enantiomers, or stereoisomerically enriched mixtures, especially enantiomerically enriched mixtures. Also included within the scope of the invention are the individual isomers of the compounds represented by formulae I above as well as any wholly or partially equilibrated mixtures thereof. The present invention also covers the individual isomers of the compounds represented by the formulas above as mixtures with isomers thereof in which one or more chiral Centers are inverted. Also, it is understood that all tautomers and mixtures of tautomers of the compounds of formulae I are included within the scope of the compounds of formulae I and preferably the formulae and subformulae corresponding thereto.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture.

The diastereomer resolution can also be carried out by standard purification processes, such as, for example, chromatography or fractional crystallization.

It is of course also possible to obtain optically active compounds of the formula I by the methods described above by using starting materials which are already optically active.

Unless indicated otherwise, it is to be understood that reference to compounds of formula I preferably includes the reference to the compounds of formula I', I", I'" and/or I"". Unless indicated otherwise, it is to be understood that reference to the compounds of formula I, I', I", I'" and I"" preferably includes the reference to the sub formulae corresponding thereto, for example the sub formulae I.1 to I.20 and preferably formulae Ia to Iz. It is also understood that the following embodiments, including uses and compositions, although recited with respect to formula I are preferably also applicable to formulae I', I", I'" and/or I"" and/or sub formulae I.1 to I.20 and preferably also to formulae Ia to Iz.

Unless indicated otherwise, it is to be understood that reference to compounds of formula I preferably also includes the reference to the compounds of formula I""". Unless indicated otherwise, it is to be understood that reference to the compounds of formula I, I', I", I'", I"" and/or I""" preferably includes the reference to the sub formulae corresponding thereto, for example the sub formulae I.1 to I.20 and preferably to one or more of formulae Ia to Iz, Iaa to Iss and/or Itt to Iww. It is also understood that the following embodiments, including uses and compositions, although recited with respect to formula I are preferably also applicable to formulae I', I", I'", I"" and/or I""'; preferably also applicable to sub formulae I.1 to I.20; and preferably also applicable to sub formulae Ia to Iz, Iaa to Iss and/or Itt to Iww.

Even more preferred are compounds of formula I wherein
$Ar^1$ is selected independently from aromatic hydrocarbons containing 5 to 12, preferably 6 to 10 and especially 6 carbon atoms and unsaturated or aromatic heterocyclic residues containing 3 to 8 and especially 4 to 6 carbon atoms and one, two or three heteroatoms, preferably one or two heteroatoms, independently selected from N, O and S and especially selected from N and O,
$Ar^2$ is selected independently from aromatic hydrocarbons containing 5 to 12, preferably 6 to 10 and especially 6 carbon atoms and unsaturated or aromatic heterocyclic residues containing 2 to 8, especially 3 to 6 and especially 4 or 5 carbon atoms and 1, 2 or 3 heteroatoms, preferably 1 or 2 heteroatoms, independently selected from N, O and S and especially selected from N and O,
$R^4$ is independently selected from residues of the formula $(Ar^3)_\alpha$—$(R^{10})_r$, wherein
$Ar^3$ is independently selected from the meanings given for $Ar^1$ and/or $Ar^2$, and more preferably is selected independently from unsubstituted or substituted, preferably substituted unsaturated or aromatic cyclic hydrocarbons containing 5 to 14 carbon atoms, preferably 6 to 10 carbon atoms; and unsubstituted or substituted, preferably substituted unsaturated or aromatic heterocyclic residues containing 2 to 10 carbon atoms and one or more heteroatoms, preferably 1 to 4 heteroatoms, more preferably 1, 2 or 3 heteroatoms, independently selected from N, O and S and more preferably from N and O,
α is 0, 1 or 2, preferably 0 or 1, and especially 1,
$R^{10}$ is independently selected from the meanings given for $R^8$ and $R^9$, and more preferably selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n$—O—$(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, preferably alkyl comprising 1 to 4 carbon atoms, $(CH_2)_n NR^{11}R^{12}$, $(CH_2)_n O (CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$ and/or selected from the group consisting $Het^9$, $OHet^9$, $N(R^{11})Het^9$, $(CR^5R^6)_k Het^9$, $O(CR^5R^6)_k Het^9$, $N(R^{11})(CR^5R^6)_k Het^9$, $(CR^5R^6)_k NR^{11}R^{12}$, $(CR^5R^6)_k OR^{13}$, $O(CR^5R^6)_k NR^{11}R^{12}$, $NR^{11}(CR^5R^6)_k NR^{11}R^{12}$, $O(CR^5R^6)_k R^{13}$, $NR^{11}(CR^5R^6)_k R^{13}$, $O(CR^5R^6)_k OR^{13}$, $NR^{11}(CR^5R^6)_k OR^{13}$, wherein
$R^5$, $R^6$ are in each case independently from one another selected from H and A;
r is 0, 1, 2, 3, 4 or 5, more preferably 0, 1, 2 or 3, and especially 1, 2 or 3,
z is 0, 1, 2, 3, 4 or 5, preferably 0, 1, 2, 3, 4 or 5, more preferably 0, 1, 2 or 3, even more preferably 1, 2 or 3, and especially 1,
$R^7$ is a nitrogen containing heterocyclic moiety, directly bound to $Ar^1$ via a nitrogen atom, said nitrogen containing heterocylic moiety being independently selected from $Het^1$, $Het^2$ and $Het^3$, wherein
$Het^1$ is an unsaturated or aromatic heterocyclic residue comprising 5 or 6 ring atoms which contains 1 to 4 nitrogen atoms and optionally 1 or 2 additional heteroatoms selected from O and S, preferably no additional heteroatoms, whereby said unsaturated or aromatic heterocyclic residue is unsubstituted or substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$ $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, more preferably selected from =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$;

$Het^2$ is a saturated, unsaturated or aromatic bicyclic residue comprising 4 to 9 carbon atoms, more preferably 5 to 8 carbon atoms, 1 to 4 nitrogen atoms and optionally 1 or 2 additional heteroatoms selected from O and S, whereby said bicyclic residue is unsubstituted or substituted by one or more substituents, preferably substituted by 1 to 6 substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $Het^3$ is a saturated monocyclic residue comprising 2 to 6 carbon atoms, preferably 3 to 5 carbon atoms, 1 to 4 nitrogen atoms and optionally 1 or 2 additional heteroatoms selected from O and S, whereby said monocyclic residue is substituted by one or more substituents, preferably 1 or 2 substituents selected from a group consisting of =O, =S and =N—$R^{14}$, and optionally substituted by one or more substituents, selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$, $R^8$ and $R^9$ are independently selected from a group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_n NR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_k OR^{12}$, $(CH_2)_nCOR^{13}$, $(CH_2)_nCOOR^{13}$, $(CH_2)_n CONR^{11}R^{12}$, $(CH_2)_nNR^{11}COR^{13}$, $(CH_2)_n NR^{11}CONR^{11}R^{12}$, $(CH_2)_nNR^{11}SO_2A$, $(CH_2)_n SO_2NR^{11}R^{12}$, $(CH_2)_nS(O)_uNR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, $(CH_2)_n NHOA$, $(CH_2)_nNR^{11}COOR^{13}$, $(CH_2)_nN(R^{11}) CH_2CH_2OR^{13}$, $(CH_2)_nN(R^{11})CH_2CH_2OCF_3$, $(CH_2)_n N(R^{11})C(R^{13})HCOOR^{12}$, $(CH_2)_nN(R^{11})C(R^{13})HCOR^{11}$, $(CH_2)_nN(COOR^{13})COOR^{14}$, $(CH_2)_nN(CONH_2)COOR^{13}$, $(CH_2)_nN(CONH_2)CONH_2$, $(CH_2)_nN(CH_2COOR^{13}) COOR^{14}$, $(CH_2)_nN(CH_2CONH_2)COOR^{13}$, $(CH_2)_n N(CH_2CONH_2)CONH_2$, $(CH_2)_nCHR^{13}COR^{14}$, $(CH_2)_n CHR^{13}COOR^{14}$ and $(CH_2)_nCHR^{13}CH_2OR^{14}$, and/or selected from the group consisting $Het^9$, $OHet^9$, $N(R^{11}) Het^9$, $(CR^5R^6)_kHet^9$, $O(CR^5R^6)_kHet^9$, $N(R^{11})(CR^5R^6)_k Het^9$, $(CR^5R^6)_kNR^{11}R^{12}$, $(CR^5R^6)_kOR^{13}$, $O(CR^5R^6)_k NR^{11}R^{12}$, $NR^{11}(CR^5R^6)_kNR^{11}R^{12}$, $O(CR^5R^6)_kR^{13}$, $NR^{11}(CR^5R^6)_kR^{13}$, $O(CR^5R^6)_kOR^{13}$, $NR^{11}(CR^5R^6)_kOR^{13}$, wherein $R^5$ and $R^6$ are as defined above/below, and wherein n and/or k independently are 0, 1, 2, 3 or 4, preferably 0, 1, 2 or 3, and even more preferred are 0 or 2;

X represents a bond or is $(CR^{11}R^{12})_h$, or $(CHR^{11})_h$-Q'—$(CHR^{12})_i$, wherein Q' is selected from a group consisting of O, S, N—$R^{15}$, $(CHal_2)_j$, $(O—CHR^{18})_j$, $(CHR^{18}—O)_j$, $CR^{18}$=$CR^{19}$, $(O—CHR^{18}CHR^{19})_j$, $(CHR^{18}CHR^{19}—O)_j$, C=O, C=$NR^{15}$, $CH(OR^{15})$, $C(OR^{15})(OR^{20})$, C(=O)N($R^{15}$), $N(R^{15})C$(=O), CH=N—$NR^{15}$, S=O, $SO_2$, $SO_2NR^{15}$ and $NR^{15}SO_2$, wherein h, i are independently from each other 0, 1, 2, 3, 4, 5 or 6, preferably 0, 1, 2 or 3 and j is 1, 2, 3, 4, 5 or 6, preferably 1, 2, 3 or 4, q is 0, 1 or 2, preferably 0 or 1, g is 1 or 2, preferably 1, and p is 1, 2 or 3, preferably 1 or 2;

and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

More preferred as compounds of formula I are compounds of formula I',

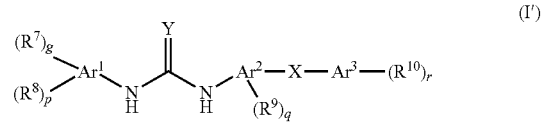

wherein $Ar^1$, $R^7$, g, $R^8$, p, Y, $R^9$, q, $Ar^3$, X, $R^{10}$ and r are as defined above/below, and preferably wherein X is a bond or is selected from $CR^{11}R^{12}$, $(CR^{11}R^{12})_j$, O, S, N—$R^{15}$, $(CHHal)_j$, $(CHal_2)_j$, $(O—CHR^{18})_j$, $(CHR^{18}—O)_j$, $CR^{18}$=$CR^{19}$, $(O—CHR^{18}CHR^{19})_j$, $(CHR^{18}CHR^{19}—O)_j$, C=O, C=$NR^{15}$, $CH(OR^{15})$, and especially wherein X is a bond or is selected from $CR^{11}R^{12}$, O, S, N—$R^{15}$, $(CHHal)_j$, $(CHal_2)_j$, $(O—CHR^{18})_j$, $(CHR^{18}—O)_j$, C=O, C=$NR^{15}$, $CH(OR^{15})$ and j is preferably 1 or 2.

More preferred as compounds of formula I are compounds of formula I",

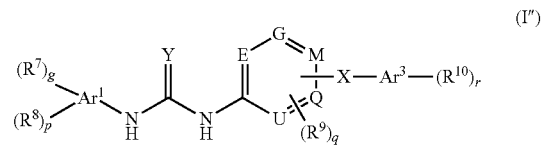

and especially compounds of formula I''',

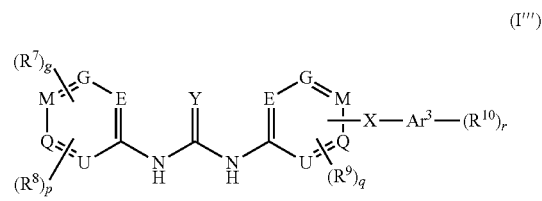

wherein $Ar^1$, $R^7$, g, $R^8$, p, Y, $R^9$, q, $Ar^3$, X, $R^{10}$ and r are as defined above/below, and wherein each of E, G, M, Q and U is independently from one another selected from carbon atoms and nitrogen atoms, with the proviso that in each of the E, G, M, Q and U containing 6-membered rings, one or more of E, G, M, Q and U are carbon atoms, and the further proviso that X and preferably substituents $(R^7)_g$ and $(R^8)_p$ are bonded to a carbon atom, respectively. More preferably, in the E, G, M, Q and U containing 6-membered ring one or more times substituted by $R^7$, U is $CR^7$, where $R^7$ is as defined above/below.

Accordingly, especially preferred as compounds of formula I are compounds of formula I'''',

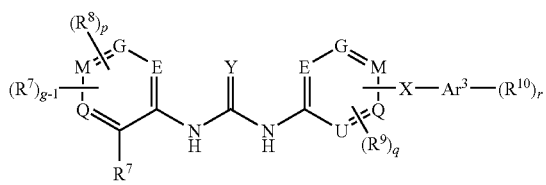

(I'''')

wherein each residue $R^7$ is independently selected from the meanings given above/below. In this formula, g is preferably 1 or 2 and especially is 1.

Accordingly, further especially preferred as compounds of formula I are compounds of formula I''''',

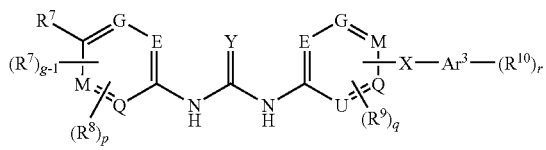

(I''''')

wherein each residue $R^7$ is independently selected from the meanings given above/below. In this formula, g is preferably 1 or 2 and especially is 1.

Preferably, E, G, M, Q and U constitute, together with the carbon atom that E and U are bound to, a bivalent 6-membered aromatic or nitrogen containing heteroaromatic ring. Preferably, one or more of E, G, M, Q and U, more preferably two or more of E, G, M, Q and U and especially three or more of E, G, M, Q and U are carbon atoms. Especially preferred, none or one of E, G, M, Q and U is a nitrogen atom. Especially preferred, E, G, M, Q and U constitute, together with the carbon atom that E and U are bound to, a 6-membered aromatic or nitrogen containing heteroaromatic ring, selected from the group consisting of phenylen, pyridinylen and pyrimydylen, wherein X is preferably bonded to a carbon atom. The substituents $R^9$ are preferably bound to a carbon atom.

In compounds of formula I, the term alkyl preferably refers to an unbranched or branched alkyl residue, preferably an unbranched alkyl residue comprising 1, 2, 3, 4, 5, 6, 7, 8, 9 or 10, preferably 1, 2, 3, 4, 5 or 6, more preferred 1, 2, 3 or 4 and especially 1 or 2 carbon atoms, or a branched alkyl residue comprising 3, 4, 5, 6, 7, 8, 9 or 10, preferably 3, 4, 5 or 6 more preferred 3 or 4 carbon atoms. The alkyl residues can be optionally substituted, especially by one or more halogen atoms, for example up to perhaloalkyl, by one or more hydroxy groups or by one or more amino groups, all of which can optionally be substituted by alkyl. If an alkyl residue is substituted by halogen, it usually comprises 1, 2, 3, 4 or 5 halogen atoms, depending on the number of carbon atoms of the alkyl residue. For example, a methyl group can comprise, 1, 2 or 3 halogen atoms, an ethyl group (an alkyl residue comprising 2 carbon atoms) can comprise 1, 2, 3, 4 or 5 halogen atoms. If an alkyl residue is substituted by hydroxy groups, it usually comprises one or two, preferably one hydroxy groups. If the hydroxy group is substituted by alkyl, the alkyl substituent comprises preferably 1 to 4 carbon atoms and is preferably unsubstituted or substituted by halogen and more preferred unsubstituted. If an alkyl residue is substituted by amino groups, it usually comprises one or two, preferably one amino groups. If the amino group is substituted by alkyl, the alkyl substituent comprises preferably 1 to 4 carbon atoms and is preferably unsubstituted or substituted by halogen and more preferred unsubstituted. According to compounds of formula I, alkyl is preferably selected from the group consisting of methyl, ethyl, trifluoro methyl, pentafluoro ethyl, isopropyl, tert.-butyl, 2-amino ethyl, N-methyl-2-amino ethyl, N,N-dimethyl-2-amino ethyl, N-ethyl-2-amino ethyl, N,N-diethyl-2-amino ethyl, 2-hydroxy ethyl, 2-methoxy ethyl and 2-ethoxy ethyl, further preferred of the group consisting of 2-butyl, n-pentyl, neo-nentyl, isopentyl, hexyl and n-decyl, more preferred of methyl, ethyl, trifluoro methyl, isopropyl and tert.-butyl.

In compounds of formula I, alkenyl is preferably selected from the group consisting of allyl, 2- or 3-butenyl, isobutenyl, sec-butenyl, furthermore preferably 4-pentenyl, isopentenyl and 5-hexenyl.

In compounds of formula I, alkylene is preferably unbranched and is more preferably methylene or ethylene, furthermore preferably propylene or butylene.

In compounds of formula I, alkylenecycloalkyl preferably has 5 to 10 carbon atoms and is preferably methylenecyclopropyl, methylenencyclobutyl, furthermore preferably methylenecyclopentyl, methylenecyclohexyl or methylenecycloheptyl, furthermore alternatively ethylenecyclopropyl, ethylenecyclobutyl, ethylenecyclopentyl, ethylenecyclohexyl or ethylenencycloheptyl, propylenecyclopentyl, propylenecyclohexyl, butylenecyclopentyl or butylenecyclohexyl.

In compounds of formula I, the term "alkoxy" preferably comprises groups of formula O-alkyl, where alkyl is an alkyl group as defined above. More preferred, alkoxy is selected from group consisting of methoxy, ethoxy, n-propoxy, isopropoxy, 2-butoxy, tert.-butoxy and halogenated, especially perhalogenated, derivatives thereof. Preferred perhalogenated derivatives are selected from the group consisting of O—$CCl_3$, O—$CF_3$, O—$C_2Cl_5$, O—$C_2F_5$, O—$C(CCl_3)_3$ and O—$C(CF_3)_3$.

In compounds of formula I, the term "alkoxyalkyl" preferably comprises branched and unbranched residues, more preferred unbranched residues, of formula $C_uH_{2u+1}$—O—$(CH_2)_v$, wherein u and v are independently from each other 1 to 6. Especially preferred is u=1 and v 1 to 4.

In compounds of formula I the term "alkoxyalkyl" includes alkoxyalkyl groups as defined above, wherein one or more of the hydrogen atoms are substituted by halogen, for example up to perhalo alkoxyalkyl.

In compounds of formula I, cycloalkyl preferably has 3-7 carbon atoms and is preferably cyclopropyl or cyclobutyl, furthermore preferably cyclopentyl or cyclohexyl, furthermore also cycloheptyl, particularly preferably cyclopentyl. The term "cycloalkyl", as used herein preferably also includes saturated heterocyclic groups, wherein one or two carbon atoms are substituted by hetero atoms, selected from the group consisting of O, NH, NA and S, wherein A is as defined as above/below. Cycloalkyl residues as defined herein can optionally be substituted, the substituents preferably selected from A, $R^{13}$, =O, =S, =N—$R^{14}$, CN and hal.

In compounds of formula I, $Ar^6$ to $Ar^8$ are preferably selected independently from one another from phenyl, naphthyl and biphenyl which is optionally substituted by one or more substituents, selected from the group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$.

In compounds of formula I, $Het^9$ is preferably an optionally substituted aromatic heterocyclic residue and even more preferred and optionally substituted saturated heterocyclic residue. In substituted saturated heterocyclic residues, the substituents are preferably selected from A, $R^{13}$, =O, =S, =N—$R^{14}$, CN and hal. Even more preferred, $Het^9$ is selected from the group consisting of 1-piperidyl, 4-piperidyl, 1-methyl-piperidin-4-yl, 1-piperazyl, 1-(4-methyl)-piperazyl, 4-methylpiperazin-1-yl amine, 1-(4-(2-hydroxyethy))-piperazyl, 4-morpholinyl, 1-pyrrolidinyl, 2-pyrrolidinyl, 3-pyrrolidinyl, 1-pyrazolidinyl 1-(2-methyl)-pyrazolidinyl, 1-imidazolidinyl or 1-(3-methyl)-imidazolidinyl, thiophen-2-yl, thiophen-3-yl, 2-pyridyl, 3-pyridyl, 4-pyridyl, 2-oxazolyl, 4-oxazolyl, 5-oxazolyl, 2-thiazolyl, 4-thiazolyl, 5-thiazolyl, chinolinyl, isochinolinyl, 2-pyridazyl, 4-pyridazyl, 2-pyrimidyl, 4-pyrimidyl, 5-pyrimidyl, 2-pyrazinyl and 3-pyrazinyl. Further preferred, $Het^9$ as defined above is optionally substituted by one or more substituents preferably selected from A, $R^{13}$, =O, =S, =N—$R^{14}$, CN and hal. More preferred, $Het^9$ is either unsubstituted or substituted once or twice by =O.

In compounds of formula I, saturated heterocyclyl is preferably a substituted or unsubstituted saturated heterocyclic residue, more preferred an unsubstituted saturated heterocyclic residue, preferably selected from the saturated groups given above in the definition of $Het^9$. Further preferred, saturated heterocyclyl as defined above is optionally substituted by one or more substituents preferably selected from A, $R^{13}$, =O, =S, =N—$R^{14}$, CN and hal. More preferred, saturated heterocyclyl is either unsubstituted or substituted once or twice by =O.

In compounds of formula I, aromatic hydrocarbons containing 6 to 14 carbon atoms and unsaturated or aromatic heterocyclic residues containing 3 to 10 carbon atoms and one or two heteroatoms, independently selected from N, O and S, are preferably selected from the definitions given herein for aryl, heteroaryl and/or $Het^9$. Heteroaryl is more preferably furanyl, thiophenyl, pyrrolyl, imidazolyl, pyrazolyl, triazolyl, tetrazolyl, thiazolyl, oxazolyl, isoxazolyl, oxadiazolyl, oxopyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl and even more preferably pyridinyl, pyrimidyl, chinolinyl, isochinolinyl, thiophenyl, thiadiazolyl, benzothiadiazolyl, oxazolyl, isoxazolyl, pyrazolyl and/or imidazolyl. Aryl more preferably refers to an optionally substituted benzene ring or to an optionally substituted benzene ring system fused to one or more optionally substituted benzene rings to form, for example, anthracene, phenanthrene, or napthalene ring systems. Even more preferably, aryl is selected from the group consisting of phenyl, 2-naphthyl, 1-naphthyl, biphenyl.

In compounds of formula I, $Ar^1$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, and especially from phenyl, pyridinyl, chinolinyl, isochinolinyl, thiophenyl, benzothiadiazolyl, oxazolyl, isoxazolyl and oxazolyl. Especially preferred, $Ar^1$ is phenyl or pyridinyl. In compounds of formula I, $Ar^1$ is also preferably selected from the =O, =S, and/or =N—$R^{14}$ substituted derivatives thereof.

In compounds of formula I, $Ar^2$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, even more preferably from phenyl, pyridinyl and pyrimidyl and especially preferred from phenyl and pyridinyl. In compounds of formula I, $Ar^2$ is preferably also selected from the =O, =S, and/or =N—$R^{14}$ substituted derivatives thereof.

In compounds of formula I, $Ar^3$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, and carbon anelated and hetero anelated derivatives thereof, even more preferably from phenyl, pyridinyl and pyrimidyl, and carbon anelated and hetero anelated derivatives thereof, and especially preferred from phenyl and pyridinyl, and carbon anelated and hetero anelated derivatives thereof. In this respect, carbon anelated derivatives thereof refer to anelated or fused ring systems, wherein the unsaturated or aromatic carbocyclic or heterocyclic moiety as given above is fused with an unsaturated or aromatic carbocyclic ring, preferably a 5- or 6-membered unsaturated or aromatic carbocyclic ring, for example cyclopentadienyl-fused derivatives and benzofused derivatives, and the dihydro- and tetrahydro-derivatives of said cyclopentadienyl-fused derivatives and benzo-fused derivatives. In compounds of formula I, $Ar^3$ is preferably also selected from the =O, =S, and/or =N—$R^{14}$ substituted derivatives thereof.

In compounds of formula I, $Ar^3$ is more preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, even more preferably from phenyl, pyridinyl and pyrimidyl and especially preferred from phenyl and pyridinyl. In compounds of formula I, $Ar^3$ is preferably also selected from the =O, =S, and/or =N—$R^{14}$ substituted derivatives thereof.

In compounds of formula I, $Ar^7$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, even more preferably from phenyl, pyridinyl and pyrimidyl and especially preferred from phenyl and pyridinyl. In compounds of formula I, $Ar^7$ is preferably also selected from the =O, =S, and/or =N—$R^{14}$ substituted derivatives thereof.

In compounds of formula I, $Ar^8$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, even more preferably from phenyl, pyridinyl and pyrimidyl and especially preferred from phenyl and pyridinyl. In compounds of formula I, $Ar^8$ is preferably also selected from the =O, =S, and/or =N—$R^{14}$ substituted derivatives thereof.

If $R^5$ and/or $R^6$ is A, then A is preferably selected, independently from one another in each case, from the group consisting of alkyl, cycloalkyl, alkoxy, alkoxyalkyl and saturated heterocyclyl, more preferably from the group consisting of alkyl, cycloalkyl, alkoxy and alkoxyalkyl, and especially is alkyl.

Preferably, the sum of h and i in one residue exceeds 0.
Preferably, the sum of n and k in one residue exceeds 0.
In $R^7$, $Het^1$ is preferably an unsaturated or aromatic heterocyclic residue comprising 5 or 6 ring atoms which contains 1 to 4 nitrogen atoms and optionally 1 or 2 additional heteroatoms selected from O and S, preferably no additional heteroatoms.

If $Het^1$ is an unsubstituted unsaturated or aromatic heterocyclic residue, it is preferably selected from 5-membered unsaturated or aromatic heterocyclic residues comprising 1 to 4 nitrogen atoms and preferably no other hetero atoms, and more preferably is selected from pyrrolyl, imidazolyl, pyrazolyl, triazolyl and tetrazolyl, and even more preferably is selected from imidazolyl, pyrazolyl, triazolyl and tetrazolyl, and especially is selected from imidazolyl, pyrazolyl and triazolyl. If $Het^1$ is an unsubstituted unsaturated or aromatic heterocyclic residue, it is even more preferably selected from

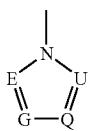

wherein E, G, Q and U are selected independently from one another from nitrogen atoms and carbon atoms and especially from N and CH, with the proviso, that one or more of E, G, Q and U are other than nitrogen atoms and especially other than N.

If Het$^1$ is an unsubstituted unsaturated or aromatic heterocyclic residue, it is even more preferably selected from

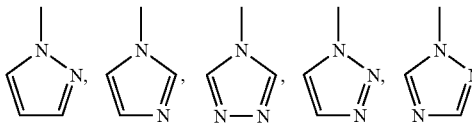 and

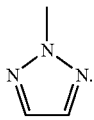

If Het$^1$ is a substituted unsaturated or aromatic heterocyclic residue, it is preferably selected from 5- or 6-membered unsaturated or aromatic heterocyclic residues comprising 1 to 4 nitrogen atoms and preferably no other hetero atoms, comprising one or more, preferably 1 to 4 substituents selected from the group =O, =S, and =N—R$^{14}$, and/or selected from the group A, R$^{13}$, Hal, NO$_2$, CN, OR$^{15}$, NR$^{15}$R$^{16}$, COOR$^{15}$, CONR$^{15}$R$^{16}$, NR$^{15}$COR$^{16}$, NR$^{15}$CONR$^{15}$R$^{16}$, NR$^{16}$SO$_2$A, COR$^{15}$, SO$_2$NR$^{15}$R$^{16}$ and S(O)$_u$A.

If Het$^1$ is a substituted unsaturated or aromatic heterocyclic residue, it is even more preferably selected from a), a1), b), b1), b2), b3), c), c1) and d) as given below:

a)

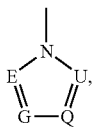

wherein E, G, Q and U are selected independently from one another from nitrogen atoms and carbon atoms and especially from N and CR$^{30}$, wherein R$^{30}$ is independently selected from A, R$^{13}$, Hal, NO$_2$, CN, OR$^{15}$, NR$^{15}$R$^{16}$, COOR$^{15}$, CONR$^{15}$R$^{16}$, NR$^{15}$COR$^{16}$, NR$^{15}$CONR$^{15}$R$^{16}$, NR$^{16}$SO$_2$A, COR$^{15}$, SO$_2$NR$^{15}$R$^{16}$ and S(O)$_u$A and especially from A, H, Hal, NO$_2$, CN, OR$^{15}$, NR$^{15}$R$^{16}$, COOR$^{15}$ and CONR$^{15}$R$^{16}$, with the proviso, that one or more of E, G, Q and U are other than nitrogen atoms and especially other than N, and with the further proviso that one or more of the residues R$^{30}$ and/or R$^{31}$ is other than H, a1)

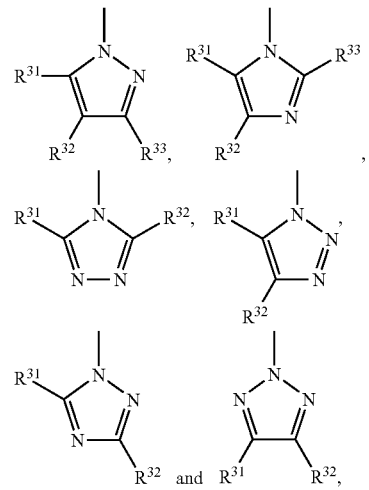

wherein R$^{31}$, R$^{32}$ and R$^{33}$ are independently selected from A, R$^{13}$, Hal, NO$_2$, CN, OR$^{15}$, NR$^{15}$R$^{16}$, COOR$^{15}$, CONR$^{15}$R$^{16}$, NR$^{15}$COR$^{16}$, NR$^{15}$CONR$^{15}$R$^{16}$, NR$^{16}$SO$_2$A, COR$^{15}$, SO$_2$NR$^{15}$R$^{16}$ and S(O)$_u$A and especially from A, H, Hal, NO$_2$, CN, OR$^{15}$, NR$^{15}$R$^{16}$, COOR$^{15}$ and CONR$^{15}$R$^{16}$, with the proviso that one or more of the residues R$^{31}$, R$^{32}$ and R$^{33}$ is other than H;

b)

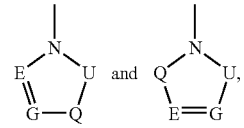

wherein E and G are selected independently from one another from N and CR$^{30}$, wherein R$^{30}$ is independently selected from A, R$^{13}$, Hal, NO$_2$, CN, OR$^{15}$, NR$^{15}$R$^{16}$COOR$^{15}$, CONR$^{15}$R$^{16}$, NR$^{15}$COR$^{16}$, NR$^{15}$CONR$^{15}$R$^{16}$, NR$^{16}$SO$_2$A, COR$^{15}$, SO$_2$NR$^{15}$R$^{16}$ and S(O)$_u$A and especially from A, H, Hal, NO$_2$, CN, OR$^{15}$, NR$^{15}$R$^{16}$, COOR$^{15}$ and CONR$^{15}$R$^{16}$, and wherein Q and U are selected independently from one another from NR$^{30}$, CR$^{31}$R$^{32}$, C=O, C=S and C=N—R$^{14}$, wherein R$^{14}$ is as defined above/below and R$^{30}$, R$^{31}$ and R$^{32}$ are independently selected from A, R$^{13}$, Hal, NO$_2$, CN, OR$^{15}$, NR$^{15}$R$^{16}$, COOR$^{15}$, CONR$^{15}$R$^{16}$, NR$^{15}$COR$^{16}$, NR$^{15}$CONR$^{15}$R$^{16}$, NR$^{16}$SO$_2$A, COR$^{15}$, SO$_2$NR$^{15}$R$^{16}$ and S(O)$_u$A and especially from A, H, Hal, NO$_2$, CN, OR$^{15}$, NR$^{15}$R$^{16}$, COOR$^{15}$ and CONR$^{15}$R$^{16}$, with the proviso, that one or more of E, G, Q and U are other than nitrogen atoms, and with the further proviso that one or more of the residues R$^{30}$, R$^{31}$ and R$^{32}$ is other than H, b1)

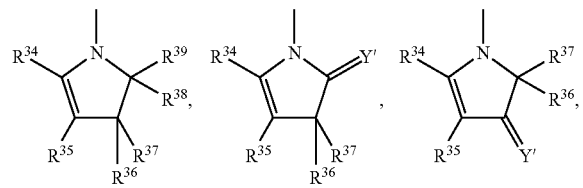

-continued

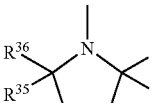

b2)

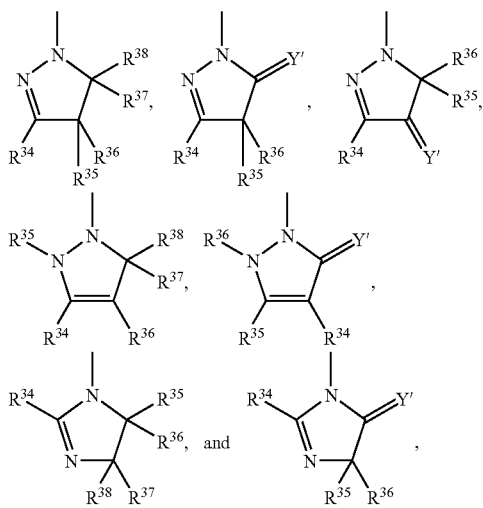

b3)

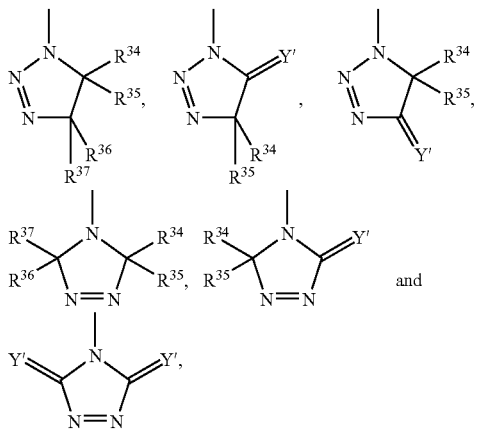

wherein in b1), b2) and b3), the substituents $R^{34}$, $R^{35}$, $R^{36}$, $R^{37}$, $R^{38}$ and $R^{39}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso that one or more of the residues $R^{34}$, $R^{35}$, $R^{36}$, $R^{37}$, $R^{38}$ and $R^{39}$ is other than H, and Y' is independently selected from =O, =S and =N—$R^{14}$, wherein $R^{14}$ is as defined above/below;

c)

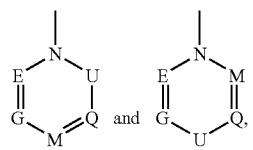

wherein E, G, M and Q are selected independently from one another from N and $CR^{30}$, wherein $R^{30}$ is independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, and U is selected from $NR^{30}$, $CR^{31}R^{32}$, C=O, C=S and C=N—$R^{14}$, wherein $R^{14}$ is as defined above/below and $R^{30}$, $R^{31}$ and $R^{32}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso, that one or more of E, G, M, Q and U and preferably two or more of E, G, M, Q and U are other than nitrogen atoms, and with the further proviso that one or more of the residues $R^{30}$, $R^{31}$ and $R^{32}$ is other than H, c1)

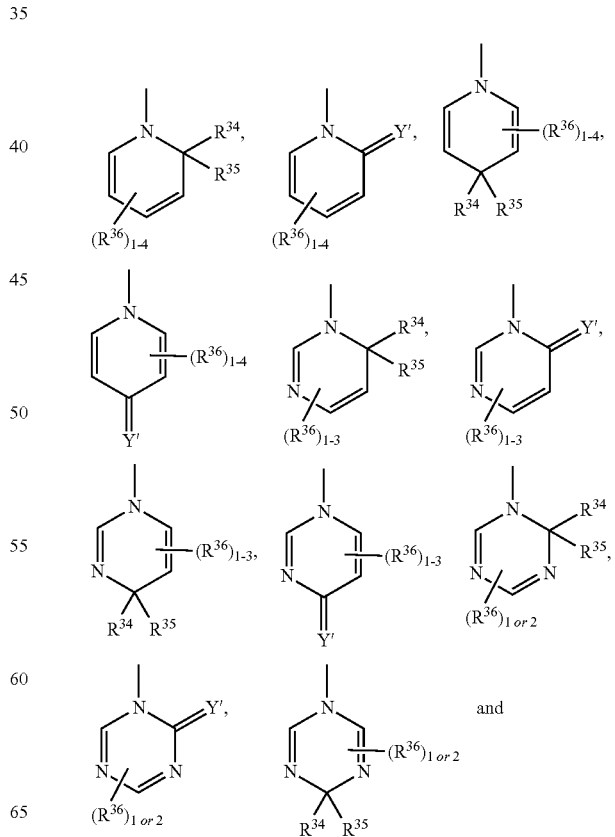

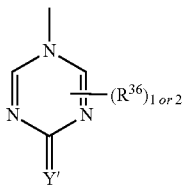

wherein in c1), the substituents $R^{34}$, $R^{35}$ and $R^{36}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso that one or more of the residues $R^{34}$, $R^{35}$ and $R^{36}$ is other than H, and Y' is independently selected from =O, =S and =N—$R^{14}$, wherein $R^{14}$ is as defined above/below;

d)

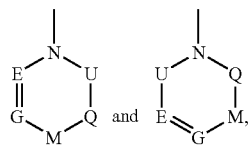

wherein E and G are selected independently from one another from N and $CR^{30}$, wherein $R^{30}$ is independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}COR^{15}$ and $CONR^{15}R^{16}$, and M, Q and U are selected independently from one another from $NR^{30}$, $CR^{31}R^{32}$, C=O, C=S and C=N—$R^{14}$, wherein $R^{14}$ is as defined above/below and $R^{30}$, $R^{31}$ and $R^{32}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso, that one or more of E, G, M, Q and U and preferably two or more of E, G, M, Q and U are other than nitrogen atoms, and with the further proviso that one or more of the residues $R^{30}$, $R^{31}$ and $R^{32}$ is other than H.

In $R^7$, $Het^2$ is preferably a saturated, unsaturated or aromatic bicyclic residue comprising 4 to 10 and preferably 5 to 9 carbon atoms, 1 to 4 and preferably 1 to 3 nitrogen atoms and preferably no other hetero atoms, which comprises one or more, preferably 1 to 4 substituents selected independently from one another from the group =O, =S, and =N—$R^{14}$, and/or selected from the group A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$. Saturated bicyclic residues are preferably selected from unsubstituted and substituted monoaza-, diaza-, triaza- and tetraaza-derivatives of bicyclo[3.1.0]hexanes, bicyclo[3.2.0]heptanes, bicyclo[4.1.0]heptanes, bicyclo[3.3.0]octanes, bicyclo[4.3.0]nonanes and bicyclo[4.4.0]decanes.

Unsaturated or aromatic bicyclic residues are preferably selected from unsubstituted and substituted monoaza-, diaza-, triaza- and tetraaza-derivatives of bicyclo[3.1.0]hexenes, bicyclo[3.2.0]heptenes, bicyclo[4.1.0]heptenes, bicyclo[3.3.0]octenes, bicyclo[4.3.0]nonenes and bicyclo[4.4.0]decenes, bicyclo[3.2.0]heptadienes, bicyclo[4.1.0]heptadienes, bicyclo[3.3.0]octadienes, bicyclo[4.3.0]nonadienes and bicyclo[4.4.0]decadienes, bicyclo[4.3.0]nonatrienes and bicyclo[4.4.0]decatrienes and bicyclo[4.4.0]decatetraenes. Unsaturated or aromatic bicyclic residues are more preferably selected from unsubstituted and substituted quinolinyl, isoquinolinyl, cinnolinyl, quinoxalinyl, quinazolinyl, phthalazinyl, and the dihydro-, tetrahydro-, hexahydro- and octahydro-derivatives thereof; indolyl, isoindolyl, benzimidazolyl, indazolyl, and the dihydro-, tetrahydro- and hexahydro-derivatives thereof; and the oxo- and dioxo-derivatives thereof. A preferred example for dioxo-derivative of an aza bicyclo[4.3.0]nonatriene or a dioxo-derivative of a dihydro-isoindole is the phthalimidoyl residue.

If $Het^2$ is a saturated or unsaturated bicyclic residue, it is preferably also selected from unsubstituted and substituted monoaza-, diaza- and triaza-derivatives of bicyclo[2.2.2]octanes, bicyclo[2.2.2]octenes and bicyclo[2.2.2]octadienes, which comprise one or more, preferably 1 to 4 substituents selected independently from one another from the group =O, =S, and =N—$R^{14}$, and/or selected from the group A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$. A preferred example of an unsubstituted derivative of a bicyclo[2.2.2]octane as described above is the 3-Oxo-2-aza-bicyclo[2.2.2]oct-2-yl residue.

$Het^2$ is more preferably selected from e)

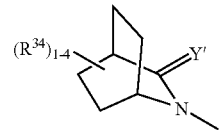

f)

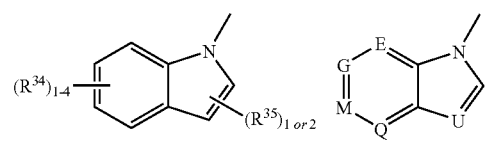

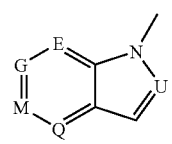

g)

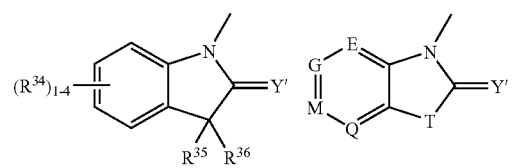

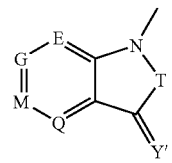

h)

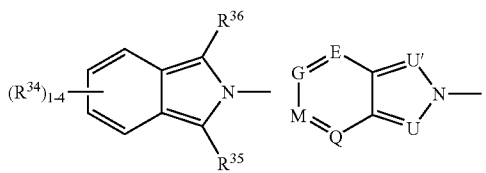

i)

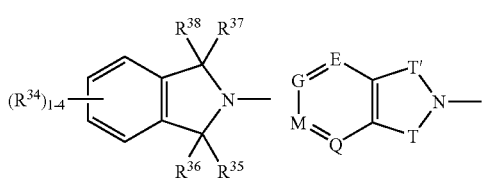

j)

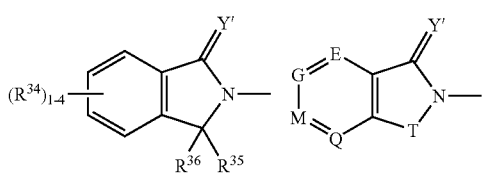

and k)

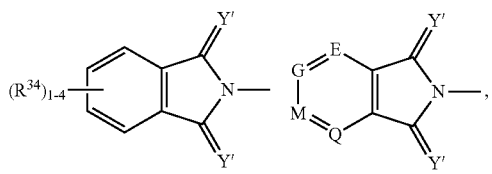

wherein E, G, M, Q, U and U' are selected independently from one another from N and $CR^{30}$, wherein $R^{30}$ is independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, and T and T' are selected from $NR^{30}$, $CR^{31}R^{32}$, Y' is selected independently from one another from =O, =S and =N—$R^{14}$, wherein $R^{14}$ is as defined above/below and $R^{30}$, $R^{31}$ and $R^{32}$ and/or $R^{34}$, $R^{35}$, $R^{36}$, $R^{37}$ and $R^{38}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso, that one or more, two or more and especially 3 or more of E, G, M, Q, U, U', T and T' are other than nitrogen atoms, and with the further proviso that the residues $Het^2$ do not contain more than 4 and preferably not more than three nitrogen atoms. Even more preferably, $Het^2$ contains 1, 2 of 3 and especially 1 or 2 nitrogen atoms in total.

$Het^2$ is more preferably selected from f)

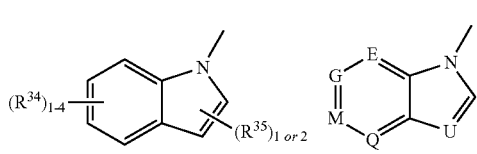

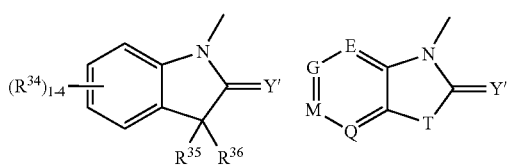

g)

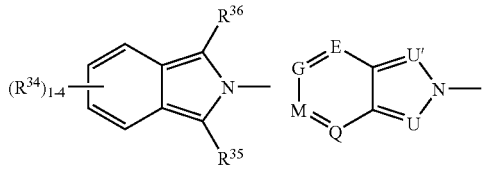

h)

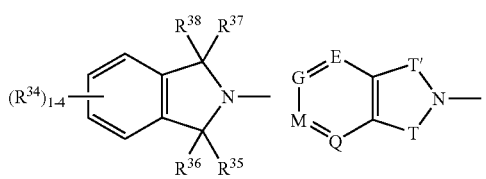

i)

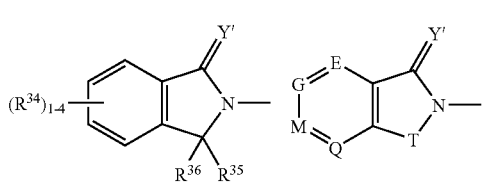

j)

and k)

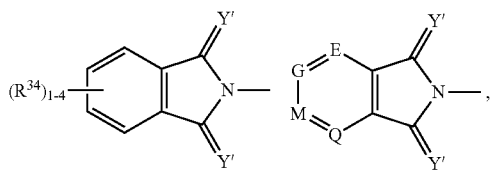

wherein E, G, M, Q, U and U' are selected independently from one another from N and $CR^{30}$, wherein $R^{30}$ is independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, and T and T' are selected from $NR^{30}$, $CR^{31}R^{32}$, Y' is selected independently from one another from =O, =S and =N—$R^{14}$, wherein $R^{14}$ is as defined above/below and $R^{30}$, $R^{31}$ and $R^{32}$ and/or $R^{34}$, $R^{35}$, $R^{36}$ and $R^{37}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso, that one or more, two or more and especially 3 or more of E, G, M, Q, U, U', T and T' are other than nitrogen atoms, and with the further proviso that the residues $Het^2$ do not contain more than 4 and preferably not more than three nitrogen atoms. Even more preferably, $Het^2$ contains 1, 2 of 3 and especially 1 or 2 nitrogen atoms in total.

In $R^7$, $Het^3$ is preferably a saturated 5-, 6- or seven-membered monocyclic residue, comprising 1 to 3 and preferably 1 or 2 nitrogen atoms and optionally 1 or 2 additional hetero atoms selected from O and S, which is substituted by one or two, preferably two substituents selected from the group consisting of =O, =S and =N—$R^{14}$. $Het^3$ optionally comprises 1 to 6, preferably 1 to 4 additional substituents, selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A and Hal.

More preferably, $Het^3$ is selected from
e)

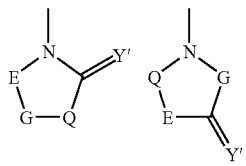

e1)

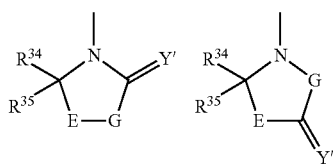

and
e2)

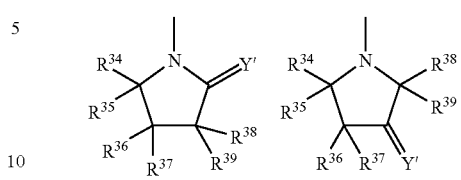

wherein E, G and Q are selected independently from one another from $NR^{30}$ and $CR^{31}R^{32}$ wherein $R^{30}$, $R^{31}$ and $R^{32}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, Y' is selected independently from one another from =O, =S and =N—$R^{14}$, wherein $R^{14}$ is as defined above/below, and $R^{34}$, $R^{35}$, $R^{36}$, $R^{37}$, $R^{38}$ and $R^{39}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso that one or more, preferably two or more of E, G and Q are other than nitrogen atoms, and with the further proviso that the residues $Het^3$ according to e), e1) and e2) do not contain more than 4 and preferably not more than three nitrogen atoms. Even more preferably, $Het^3$ according to e), e1) and e2) contains 1, 2 of 3 and especially 1 or 2 nitrogen atoms in total.

Even more preferably, $Het^3$ is selected from
f)

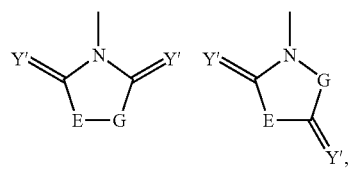

especially

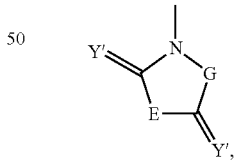

f1)

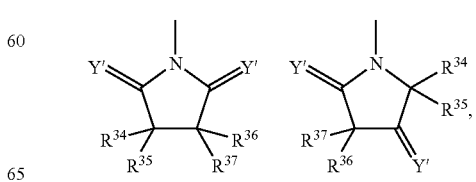

especially

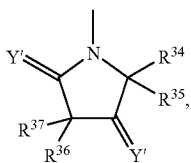

and
f2)

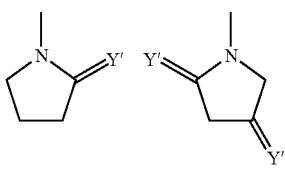

wherein E and G are selected independently from one another from $NR^{30}$ and $CR^{31}R^{32}$ wherein $R^{30}$, $R^{31}$ and $R^{32}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, Y' is selected independently from one another from =O, =S and =N—$R^{14}$, wherein $R^{14}$ is as defined above/below, and $R^{34}$, $R^{35}$, $R^{36}$ and $R^{37}$ are independently selected from A, $R^{13}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$ and $S(O)_uA$ and especially from A, H, Hal, $NO_2$, CN, $OR^{15}$, $NR^{15}R^{16}$, $COOR^{15}$ and $CONR^{15}R^{16}$, with the proviso that one or more of E and G are other than nitrogen atoms; and with the further proviso that the residues $Het^3$ according to f, f1) and f2) do not contain more than 4 and preferably not more than three nitrogen atoms. Even more preferably, $Het^3$ according to e), e1) and e2) contains 1, 2 of 3 and especially 1 or 2 nitrogen atoms in total.

Preferably, the residues $Het^3$ according to e), e1) and e2) do not contain more than 4 and preferably not more than three nitrogen atoms. Even more preferably, $Het^3$ according to e), e1) and e2) contains 1, 2 or 3 and especially 1 or 2 nitrogen atoms in total.

Preferably, the residues $Het^3$ according to f, f1) and f2) do not contain more than 3 and preferably not more than two nitrogen atoms. Even more preferably, $Het^3$ according to f), f1) and f2) contains 1 or 2 and especially 1 nitrogen atom in total.

Especially preferably, $Het^1$ is selected from

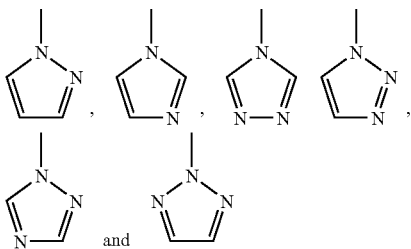

and/or

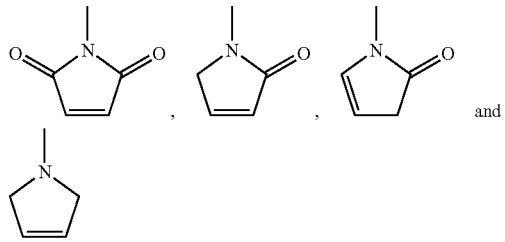

and/or

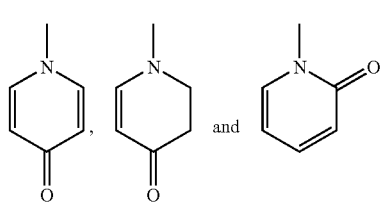

and/or derivatives thereof that comprise 1 to 4, preferably 1 to 3 and especially 1 or 2 substituents, selected from A, $R^{13}$, Hal, $NO_2$, CN, $OR^{15}$, $NR^{15}R^{16}$, $COOR^{15}$, $CONR^{15}R^{16}$, $NR^{15}CONR^{15}R^{16}$, $NR^{16}SO_2A$, $SO_2NR^{15}R^{16}$ and $S(O)_uA$ and especially from A, Hal, $NO_2$, CN, $OR^{15}$, $NR^{15}R^{16}$, $COOR^{15}$ and $CONR^{15}R^{16}$.

Especially preferably, $Het^2$ is selected from

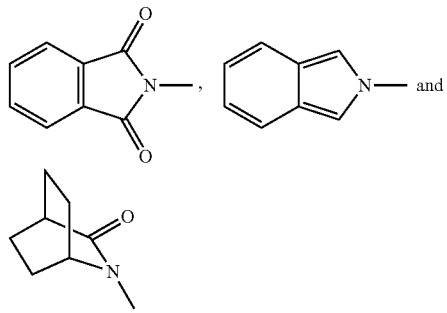

and/or derivatives thereof that comprise 1 to 4, preferably 1 to 3 and especially 1 or 2 substituents, selected from A, $R^{13}$, Hal, $NO_2$, CN, $OR^{15}$, $NR^{15}R^{16}$, $COOR^{15}$, $CONR^{15}R^{16}$, $NR^{15}CONR^{15}R^{16}$, $NR^{16}SO_2A$, $SO_2NR^{15}R^{16}$ and $S(O)_uA$ and especially from A, Hal, $NO_2$, CN, $OR^{15}$, $NR^{15}R^{16}$, $COOR^{15}$ and $CONR^{15}R^{16}$.

Even more preferably, $Het^2$ is selected from

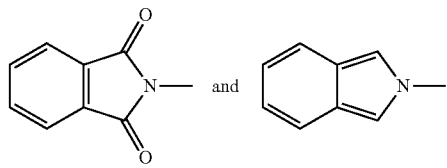

and/or derivatives thereof that comprise 1 to 4, preferably 1 to 3 and especially 1 or 2 substituents, selected from A, $R^{13}$, Hal, $NO_2$, CN, $OR^{15}$, $NR^{15}R^{16}$, $COOR^{15}$, $CONR^{15}R^{16}$, $NR^{15}CONR^{15}R^{16}NR^{16}SO_2A$, $SO_2NR^{15}R^{16}$ and $S(O)_uA$ and especially from A, Hal, $NO_2$, CN, $OR^{15}$, $NR^{15}R^{16}$, $COOR^{15}$ and $CONR^{15}R^{16}$.

Especially preferably, Het³ is selected from

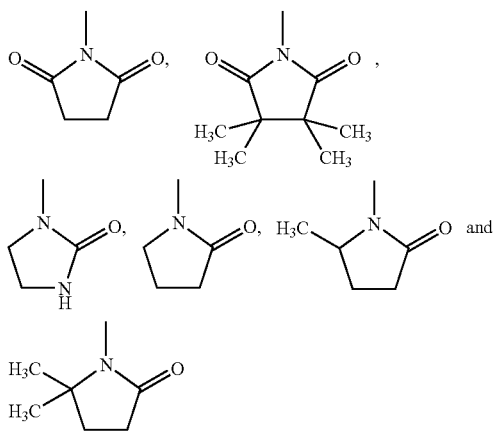

and/or derivatives thereof that comprise 1 to 4, preferably 1 to 3 and especially 1 or 2 substituents, selected from A, $R^{13}$, Hal, $NO_2$, CN, $OR^{15}$, $NR^{15}R^{16}$, $COOR^{15}$, $CONR^{15}R^{16}$, $NR^{15}CONR^{15}R^{16}$, $NR^{16}SO_2A$, $SO_2NR^{15}R^{16}$ and $S(O)_uA$ and especially from A, Hal, $NO_2$, CN, $OR^{15}$, $NR^{15}R^{16}$, $COOR^{15}$ and $CONR^{15}R^{16}$.

Especially preferably, Het³ is selected from

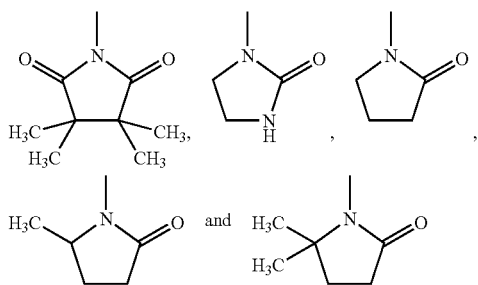

and/or derivatives thereof that comprise 1 to 4, preferably 1 to 3 and especially 1 or 2 substituents, selected from A, $R^{13}$, Hal, $NO_2$, CN, $OR^{15}$, $NR^{15}R^{16}$, $COOR^{15}$, $CONR^{15}R^{16}$, $NR^{15}CONR^{15}R^{16}$, $NR^{16}SO_2A$, $SO_2NR^{15}R^{16}$ and $S(O)_uA$ and especially from A, Hal, $NO_2$, CN, $OR^{15}$, $NR^{15}R^{16}$, $COOR^{15}$ and $CONR^{15}R^{16}$.

According to the invention, X—Ar³ is preferably selected from the group consisting of

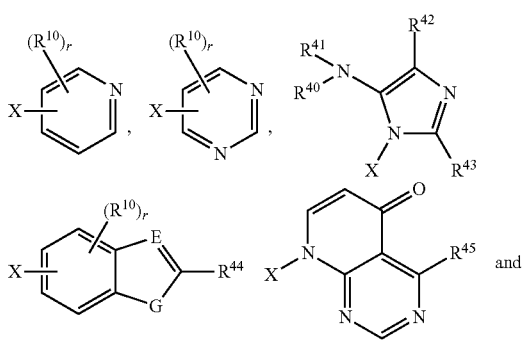

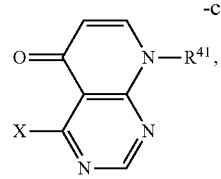

and more preferably of

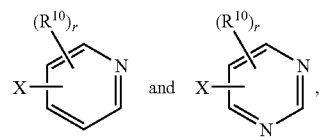

wherein X, $R^{10}$ and r are as defined above/below; E is selected from N and $CR^{30}$, wherein $R^{30}$ is as defined above/below and especially is H or A; G is selected from $NR^{30}$ and $CR^{31}R^{32}$, wherein $R^{30}$, $R^{31}$ and $R^{32}$ are as defined above/below; and $R^{40}$, $R^{41}$, $R^{42}$, $R^{43}$, $R^{44}$ and $R^{45}$ are selected independently from one another from the meanings given for $R^8$, $R^9$ and $R^{10}$. More preferably, X is a bond or O; $R^{10}$ is H or preferably selected from A, Hal, $(CH_2)_nCONR^{11}R^{12}$ and especially from $CONR^{11}R^{12}$; r is 0, 1 or 2, and especially 1 or 2; $R^{40}$, $R^{41}$ and $R^{43}$ are selected independently from one another from H, A and $R^{13}$; $R^{10}$ and $R^{42}$ are selected independently from one another from H, $R^{13}$, A, Hal and $(CH_2)_nCONR^{11}R^{12}$ and especially from H, A, $CONR^{11}R^{12}$, CONHA and CONHMe; $R^{44}$ is preferably selected from $(CH_2)_nNR^{11}R^{12}$, $NR^{11}R^{12}$, $(CH_2)_nNR^{11}COR^{13}$, $(CH_2)_nNR^{11}CONR^{11}R^{12}$ and $(CH_2)_nNR^{11}COOR^{13}$ and especially from $NR^{11}R^{12}$, $NR^{11}CONR^{11}R^{12}$, $NR^{11}COOR^{13}$ and $NR^{11}COOA$; $R^{45}$ is preferably selected from A, Hal, $(CH_2)_nNR^{11}R^{12}$, $(CH_2)_nNR^{11}COR^{13}$, $(CH_2)_nNR^{11}CONR^{11}R^{12}$, $(CH_2)_nNR^{11}COOR^{13}$ and $NR^{11}R^{12}$ and especially from $NR^{11}R^{12}$, NHA and $NH_2$.

According to the invention, X—Ar³ is preferably selected from the group consisting of

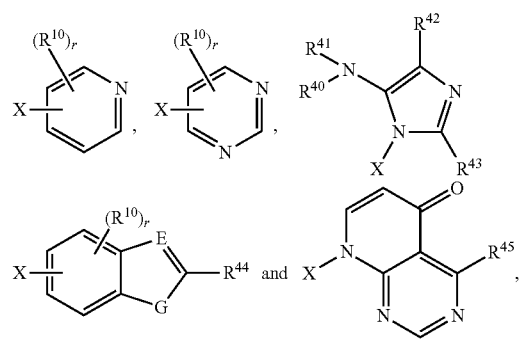

and more preferably of

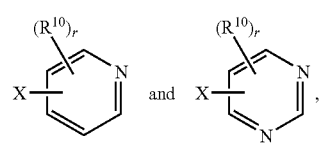

wherein X, $R^{10}$ and r are as defined above/below; E is selected from N and $CR^{30}$, wherein $R^{30}$ is as defined above/below and especially is H or A; G is selected from $NR^{30}$ and $CR^{31}R^{32}$ wherein $R^{30}$, $R^{31}$ and $R^{32}$ are as defined above/below; and $R^{40}$, $R^{41}$, $R^{42}$, $R^{43}R^{44}$ and $R^{45}$ are selected independently from one another from the meanings given for $R^8$, $R^9$ and $R^{10}$. More preferably, X is a bond or O; $R^{10}$ is H or preferably selected from A, Hal, $(CH_2)_nCONR^{11}R^{12}$ and especially from $CONR^{11}R^{12}$; r is 0, 1 or 2, and especially 1 or 2; $R^{40}$, $R^{41}$ and $R^{43}$ are selected independently from one another from H, A and $R^{13}$; $R^{10}$ and $R^{42}$ are selected independently from one another from H, $R^{13}$, A, Hal and $(CH_2)_nCONR^{11}R^{12}$ and especially from H, A, $CONR^{11}R^{12}$, CONHA and CONHMe; $R^{44}$ is preferably selected from $(CH_2)_nNR^{11}R^{12}$, $NR^{11}R^{12}$, $(CH_2)_nNR^{11}COR^{13}$, $(CH_2)_nNR^{11}CONR^{11}R^{12}$ and $(CH_2)_nNR^{11}COOR^{13}$ and especially from $NR^{11}R^{12}$, $NR^{11}CONR^{11}R^{12}$, $NR^{11}COOR^{13}$ and $NR^{11}COOA$; $R^{45}$ is preferably selected from A, Hal, $(CH_2)_nNR^{11}R^{12}$, $(CH_2)_nNR^{11}COR^{13}$, $(CH_2)_nNR^{11}CONR^{11}R^{12}$, $(CH_2)_nNR^{11}COOR^{13}$ and $NR^{11}R^{12}$ and especially from $NR^{11}R^{12}$, $NHA$ and $NH_2$.

Preferably, $(CR^5R^6)$ and/or $(CR^5R^6)_k$ is linear or branched alkylen, preferably linear or branched $C_1$-$C_4$ alkylen, which is optionally substituted as described above/below and preferably is unsubstituted.

Another preferred aspect of the instant invention relates to compounds of formula I, wherein n is 0 in the residues $R^8$, $R^9$ and/or $R^{10}$ and especially in $R^{10}$.

Another preferred aspect of the instant invention relates to compounds of formula I, wherein in the residues $R^8$, n is 1, 2 or 3 and especially is 2.

Another preferred aspect of the instant invention relates to compounds of formula I that comprise one or two, preferably one residue $R^7$ which is preferably bonded to $Ar^1$ in the ortho, meta or para position relative to the urea moeity $Ar^1$ is bonded to. More preferably, the residue $R^7$ is bonded to $Ar^1$ in the ortho or para position, and especially in the ortho position, relative to the urea moiety that $Ar^1$ is bonded to.

Another preferred aspect of the instant invention relates to compounds of formula I that comprise one residue $R^7$ that is bonded to $Ar^1$ in the para position Another preferred aspect of the instant invention relates to compounds of formula I, wherein X represents a bridging group, selected from $(CR^{11}R^{12})_n$ or $(CHR^{11})_n$-Q'-$(CHR^{12})_t$.

The invention relates in particular to compounds of the formula I in which at least one of said radicals has one of the preferred meanings given above.

Some more preferred groups of compounds may be expressed by the following sub-formulae I.1) to I.20), which correspond to the formula I and in which radicals not denoted in greater detail are as defined in the formula I, but in which I.1) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl;

I.2) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl, and
p is 1, 2 or 3;

I.3) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl,
p is 1, 2 or 3, and
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$;

I.4) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl,
p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$;

I.5) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl,
p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein
n is 0 or 1;

I.6) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl,
p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein
n is 0 or 1, and
u is 0;

I.7) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S;

I.8) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl;

I.9) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_k NR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n NR^{11}R^{12}$, $(CH_2)_nO(CH_2)_kNR^{11}R^{12}$, $(CH_2)_n NR^{11}(CH_2)_kNR^{11}R^{12}$, $(CH_2)_nO(CH_2)_kOR^{11}$, $(CH_2)_n NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n SO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_n O(CH_2)_kNR^{11}R^{12}$, $(CH_2)_nCOR^{13}$, $(CH_2)_n COOR^{13}$, $(CH_2)_nCONR^{11}R^{12}$ and especially $(CH_2)_n CONR^{11}R^{12}$;

I.10) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n NR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nS(O)_u NR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n NR^{11}R^{12}$, $(CH_2)_nO(CH_2)_kNR^{11}R^{12}$, $(CH_2)_n NR^{11}(CH_2)_kNR^{11}R^{12}$, $(CH_2)_nO(CH_2)_kOR^{11}$, $(CH_2)_n NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n SO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_n O(CH_2)_kNR^{11}R^{12}$, $(CH_2)_nCOR^{13}$, $(CH_2)_n COOR^{13}$, $(CH_2)_nCONR^{11}R^{12}$ and especially $(CH_2)_n CONR^{11}R^{12}$, wherein n is 0, 1 or 2, preferably 0 or 1;

I.11) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, even more preferably phenyl or pyridinyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n$ $SO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n$ $SO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_n$ $O(CH_2)_kNR^{11}R^{12}$, $(CH_2)_nCOR^{13}$, $(CH_2)_n$ $COOR^{13}$, $(CH_2)_nCONR^{11}R^{12}$ and especially $(CH_2)_n$ $CONR^{11}R^{12}$, wherein n is 0, 1 or 2, preferably 0 or 1 and r is 0, 1 or 2, preferably 0 or 1;

I.12) p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_n$ $COR^{13}$, $(CH_2)_nCOOR^{13}$, $(CH_2)_nCONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n$ $SO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_n$ $O(CH_2)_kNR^{11}R^{12}$, $(CH_2)_nCOR^{13}$, $(CH_2)_n$ $COOR^{13}$, $(CH_2)_nCONR^{11}R^{12}$ and especially $(CH_2)_n$ $CONR^{11}R^{12}$, wherein n is 0, 1 or 2, preferably 0 or 1 and r is 0, 1 or 2, preferably 0 or 1;

I.13) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}(CH_2)_k$ $NR^{11}R^{12}$, $(CH_2)_nO(CH_2)_kOR^{11}$, $(CH_2)_nNR^{11}(CH_2)_k$ $OR^{12}$, $(CH_2)_nCOR^{13}$, $(CH_2)_nCOOR^{13}$, $(CH_2)_n$ $CONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n$ $SO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_n$ $O(CH_2)_kNR^{11}R^{12}$, $(CH_2)_nCOR^{13}$, $(CH_2)_n$ $COOR^{13}$, $(CH_2)_nCONR^{11}R^{12}$ and especially $(CH_2)_n$ $CONR^{11}R^{12}$, wherein n is 0, 1 or 2, preferably 0 or 1 and r is 0, 1 or 2, preferably 0 or 1;

I.14) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}(CH_2)_k$ $NR^{11}R^{12}$, $(CH_2)_nO(CH_2)_kOR^{11}$, $(CH_2)_nNR^{11}(CH_2)_k$ $OR^{12}$, $(CH_2)_nCOR^{13}$, $(CH_2)_nCOOR^{13}$, $(CH_2)_n$ $CONR^{11}R^{12}$, $(CH_2)_nS(O)_uNR^{11}R^{12}$, $(CH_2)_nSO_2NR^{11}R^{12}$ and $(CH_2)_nS(O)_uR^{13}$, wherein u is 0, and q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nS(O)_uNR^{11}R^{12}$, $(CH_2)_n$ $SO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_n$ $O(CH_2)_kNR^{11}R^{12}$, $(CH_2)_nCOR^{13}$, $(CH_2)_n$ $COOR^{13}$, $(CH_2)_nCONR^{11}R^{12}$ and especially $(CH_2)_n$ $CONR^{11}R^{12}$, wherein n is 0, 1 or 2, preferably 0 or 1 and r is 0, 1 or 2, preferably 0 or 1;

I.15) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}$ $(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, wherein q is 0 or 1, and X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, preferably alkyl comprising 1 to 4 carbon atoms, $(CH_2)_n NR^{11}R^{12}$, $(CH_2)_n O(CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$, wherein n is 0, 1 or 2, preferably 0 or 1 and r is 0, 1 or 2, preferably 0 or 1;

I.16) q is 0 or 1, and

X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, preferably alkyl comprising 1 to 4 carbon atoms, $(CH_2)_n NR^{11}R^{12}$, $(CH_2)_n O(CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$, wherein n is 0, 1 or 2, preferably 0 or 1 and r is 0, 1 or 2, preferably 0 or 1;

I.17) X is a bond or is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, preferably alkyl comprising 1 to 4 carbon atoms, $(CH_2)_n NR^{11}R^{12}$, $(CH_2)_n O(CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$, wherein n is 0, 1 or 2, preferably 0 or 1 and r is 0, 1 or 2, preferably 0 or 1;

I.18) $Ar^2$ is phenyl, pyridinyl or pyrimidyl, and especially is phenyl or pyridinyl; and $R^{10}$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$ preferably alkyl comprising 1 to 4 carbon atoms, $(CH_2)_n NR^{11}R^{12}$, $(CH_2)_n O(CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$, n is 0, 1 or 2, preferably 0 or 1 and r is 0, 1 or 2, preferably 0 or 1;

I.19) $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, preferably alkyl comprising 1 to 4 carbon atoms, $(CH_2)_n NR^{11}R^{12}$, $(CH_2)_n O(CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$, n is 0, 1 or 2, preferably 0 or 1 and r is 0, 1 or 2, preferably 0 or 1;

I.20) $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_n CN$, $(CH_2)_n NR^{11}R^{12}$, $(CH_2)_n O(CH_2)_k NR^{11}R^{12}$, $(CH_2)_n NR^{11}(CH_2)_k NR^{11}R^{12}$, $(CH_2)_n O(CH_2)_k OR^{11}$, $(CH_2)_n NR^{11}(CH_2)_k OR^{12}$, $(CH_2)_n COR^{13}$, $(CH_2)_n COOR^{13}$, $(CH_2)_n CONR^{11}R^{12}$, $(CH_2)_n S(O)_u NR^{11}R^{12}$, $(CH_2)_n SO_2 NR^{11}R^{12}$ and $(CH_2)_n S(O)_u R^{13}$, preferably alkyl comprising 1 to 4 carbon atoms, $(CH_2)_n NR^{11}R^{12}$, $(CH_2)_n O(CH_2)_k NR^{11}R^{12}$, $(CH_2)_n COR^{13}$, $(CH_2)_n COOR^{13}$, $(CH_2)_n CONR^{11}R^{12}$ and especially $(CH_2)_n CONR^{11}R^{12}$, and r is 0, 1 or 2, preferably 0 or 1.

One preferred embodiment of the instant invention relates to compounds of formula I and preferably one or more of sub formulae I.1) to I.20), wherein p is 1, 2 or 3 and $R^8$ is independently selected from the group consisting of methyl, ethyl, isopropyl, tert.-butyl, F, Cl, Br, $CF_3$, $C(CF_3)_3$, $SO_2CF_3$, methoxy, ethoxy, tert.-butoxy, perfluoro tert.-butoxy ($OC(CF_3)_3$), methyl sulfanyl ($SCH_3$), ethyl sulfanyl ($SCH_2CH_3$), acetyl ($COCH_3$), propionyl ($COCH_2CH_3$), butyryl ($COCH_2CH_2CH_3$). If p is 2 or 3, all substituents can be the same or different.

Another preferred embodiment of the instant invention relates to compounds of formula I and preferably one or more of sub formulae I.1) to I.20), wherein X is selected from the group consisting of S, N—$R^{21}$, $CH_2$, $CH_2CH_2$, $OCH_2$ and $CH_2O$.

Another preferred embodiment of the instant invention relates to compounds of formula I and preferably one or more of sub formulae I.1) to I.20), wherein X is a bond, i.e. $Ar^3$ is directly bonded to $Ar^2$.

Another preferred embodiment of the instant invention relates to compounds of formula I and preferably one or more of sub formulae I.1) to I.20), wherein X is selected from the group consisting of S, CH$_2$.

Another even more preferred embodiment of the instant invention relates to compounds of formula I and preferably one or more of sub formulae I.1) to I.20), wherein X is O.

Another preferred embodiment of the instant invention relates to compounds of formula I and preferably one or more of sub formulae I.1) to I.20), wherein Y is selected from the group consisting of C(R$^{22}$)—NO$_2$, C(R$^{22}$)—CN and C(CN)$_2$.

Another more preferred embodiment of the instant invention relates to compounds of formula I and preferably one or more of sub formulae I.1) to I.20), wherein Y is selected from the group consisting of O, S and NR$^{21}$.

Another even more preferred embodiment of the instant invention relates to compounds of formula I and preferably one or more of sub formulae I.1) to I.20), wherein Y is selected from the group consisting of O and S.

Another even more preferred embodiment of the instant invention relates to compounds of formula I and preferably one or more of sub formulae I.1) to I.20), wherein Y is O.

Another preferred embodiment of the instant invention relates to compounds of formula I and preferably one or more of sub formulae I.1) to I.20), wherein Ar$^3$ is pyridinyl.

Another preferred embodiment of the instant invention relates to compounds of formula I and preferably one or more of sub formulae I.1) to I.20), wherein r is either 0 or 1. If r is 1, R$^{10}$ is preferably (CH$_2$)$_n$CONR$^{11}$R$^{12}$ and especially (CH$_2$)$_n$CONR$^{11}$R$^{12}$, wherein n in 0. In this embodiment, R$^{11}$ is preferably selected from the group consisting of H and A and more preferred from H and alkyl, and R$^{12}$ is preferably selected from the group consisting of H and A and more preferred from H and alkyl. Especially preferred as residue R$^{10}$ are carbamoyl, more preferred alkyl carbamoyl or dialkyl carbamoyl, even more preferred methyl carbamoyl or dimethyl carbamoyl, ethyl carbamoyl or diethyl carbamoyl and especially preferred methyl carbamoyl (—CONHCH$_3$). This embodiment is especially preferred when Ar$^2$ is pyridinyl. When Ar$^2$ is pyridinyl, R$^{10}$ is preferably bonded in a vicinal position to the nitrogen atom of the pyridinyl residue, i.e. in 2- and/or 6-position of the pyridinyl residue.

Another preferred embodiment of the instant invention relates to compounds of formula I and preferably one or more of sub formulae I.1) to I.20), wherein Ar$^1$ is phenyl.

Another preferred embodiment of the instant invention relates to compounds of formula I and preferably one or more of sub formulae I.1) to I.20), wherein Ar$^1$ is a 6-membered aryl or heteroaryl moiety which is substituted by one or more, preferably one residue CF$_3$, preferably in the 3- and/or 5-position relative to the urea moiety Ar$^1$ is bonded to.

Another preferred embodiment of the instant invention relates to compounds of formula I and preferably one or more of sub formulae I.1) to I.20), wherein Ar$^2$ is phenyl.

Another preferred embodiment of the instant invention relates to compounds of formula I and preferably one or more of sub formulae I.1) to I.20), wherein q is 0, i.e. Ar$^2$ or the 6-membered aromatic, E, G, M, Q and U containing group bound to the urea moiety is unsubstituted.

Another preferred embodiment of the instant invention relates to compounds of formula I and preferably one or more of sub formulae I.1) to I.20), wherein the definition of residues R$^8$, R$^9$ and/or R$^{10}$ does not comprise H. This embodiment preferably is not applicable to sub formulae Ia to Iz and especially not applicable to the definition of R$^{10}$ in sub formulae Ia to Iz, since the definition in said sub formulae explicitly incorporates H. The same preferably also applies to sub formulae Iaa to Iss and/or Itt to Iww.

Another preferred embodiment of the instant invention relates to compounds of formula I and preferably one or more of sub formulae I.1) to I.20), wherein q is 1, i.e. Ar$^2$ or the 6-membered aromatic, E, G, M, Q and U containing group bound to the urea moiety is substituted by one substituent, preferably a substituent as defined above and more preferably a substituent selected from alkyl and hal, and especially selected from CH$_3$, CH$_2$CH$_3$ and hal.

Another preferred embodiment of the instant invention relates to compounds of formula I and preferably one or more of formulae I.1) to I.20), wherein (R$^8$)$_p$—Ar$^1$ is selected from the group consisting of 5-trifluoromethyl-phenyl-, 3-trifluoromethyl-phenyl, 4-methyl-5-chloro-phenyl, 4-chloro-5-methyl-phenyl, 4-chloro-5-methyl-phenyl, 4-chloro-5-trifluoro methyl-phenyl, 3-acetyl-phenyl, 4-acetyl-phenyl, 2-bromo-phenyl, 3-bromo-phenyl, 4-bromo-phenyl, 4-bromo-2-chloro-phenyl, 4-bromo-3-methyl-phenyl, 4-bromo-3-trifluoromethyl-phenyl, 2-chloro-phenyl, 2-chloro-4-trifluoromethyl-phenyl, 2-chloro-5-trifluoromethyl-phenyl, 3-chloro-phenyl, 3-chloro-4-methyl-phenyl, 3-chloro-4-methoxy-phenyl, 3-chloro-4-methoxy-phenyl, 4-chloro-phenyl, 4-chloro-2-trifluoromethyl-phenyl, 4-chloro-3-trifluoromethyl-phenyl, 4-chloro-2-methyl-phenyl, 5-chloro-2-methyl-phenyl, 5-chloro-2-methoxy-phenyl, 2,3-dichloro-phenyl, 2,4-dichloro-phenyl, 2,5-dichloro-phenyl, 3,4-dichloro-phenyl, 3,5-dichloro-phenyl, 2,4,5-trichloro-phenyl, 4-fluoro-phenyl, 4-fluoro-3-trifluoromethyl-phenyl, 4-ethoxy-phenyl, 2-methoxy-phenyl, 2-methoxy-5-trifluoromethyl-phenyl, 4-methoxy-phenyl, 2,5-dimethoxy-phenyl, 2-trifluoromethyl-phenyl, 3-trifluoromethyl-phenyl, 3-trifluoromethoxy-phenyl, 4-trifluoromethyl-phenyl, 4-trifluoromethoxy-phenyl, 3,5-bis-trifluoromethyl-phenyl, 3-methoxy-phenyl, 3-methylsulfanyl-phenyl, 4-methylsulfanyl-phenyl, o-tolyl (2-methyl-phenyl), m-tolyl (3-methyl-phenyl), p-tolyl (4-methyl-phenyl), 2,3-dimethyl-phenyl, 2,3-dimethyl-phenyl, 2,5-dimethyl-phenyl, 3,4-dimethyl-phenyl, 3,5-dimethyl-phenyl, 2-ethyl-phenyl, 3-ethyl-phenyl, 4-ethyl-phenyl, 4-isopropyl-phenyl, 4-tert-butyl-phenyl and 5-tert-butyl-isoxazol-3-yl. Additionally preferred are compounds of formula I and preferably one or more of formulae I.1) to I.20), wherein (R$^8$)$_p$—Ar$^1$ is selected from the residues given above and comprises one or two, preferably one substituent R$^7$ and especially one or two, preferably one substituent R$^7$ indicated herein as preferred, more preferred or especially preferred.

Another more preferred embodiment of the instant invention relates to compounds of formula I and preferably one or more of formulae I.1) to I.20), wherein (R$^8$)$_p$—Ar$^1$ is selected from the group consisting of 5-trifluoromethyl-phenyl, 3-trifluoromethyl-phenyl, 4-methyl-5-chloro-phenyl, 4-chloro-5-methyl-phenyl, 4-chloro-5-methyl-phenyl, and 4-chloro-5-trifluoro methyl-phenyl. Additionally more preferred are compounds of formula I and preferably one or more of formulae I.1) to I.20), wherein (R$^8$)$_p$—Ar$^1$ is selected from the residues given above and comprises one or two, preferably one substituent R$^7$ and especially one or two, preferably one substituent R$^7$ indicated herein as preferred, more preferred or especially preferred.

Another especially preferred embodiment of the instant invention relates to compounds of formula I and preferably one or more of formulae I.1) to I.20), wherein (R$^8$)$_p$—Ar$^1$ is selected from the group consisting of 5-trifluoromethyl-phenyl and 3-trifluoromethyl-pheny. Additionally especially preferred are compounds of formula I and preferably one or more of formulae I.1) to I.20), wherein (R$^8$)$_p$—Ar$^1$ is selected from the residues given above and comprises one or two, preferably one substituent $R^7$ and especially one or two, preferably one substituent $R^7$ indicated herein as preferred, more preferred or especially preferred.

Another preferred embodiment of the instant invention relates to compounds of formula I and preferably one or more of sub formulae I.1) to I.20), wherein $(R^8)_p$—$Ar^1$ is as defined above, but comprises one or more additional residues, preferably one additional residue. The additional residues are preferably selected from the meanings given for $R^7$ and more preferably from

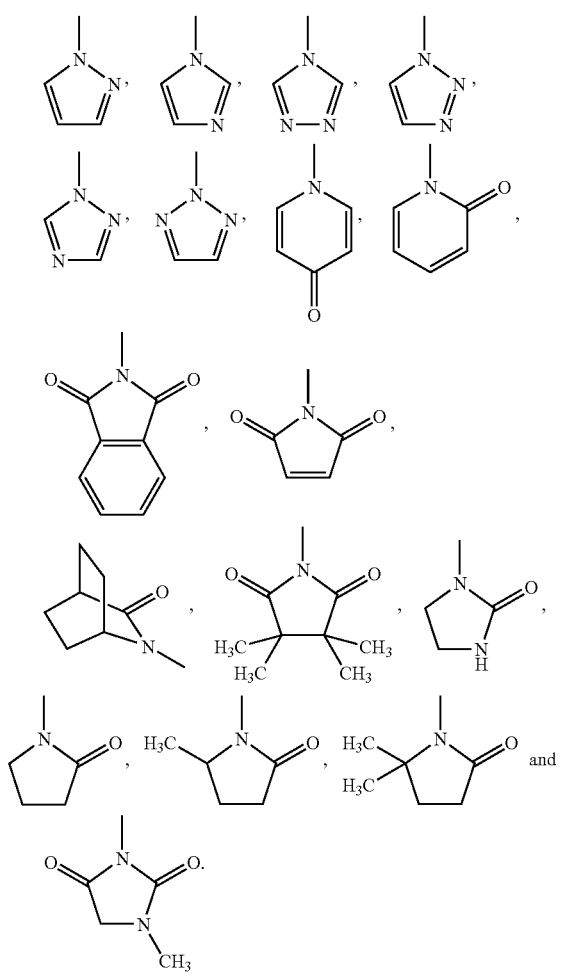

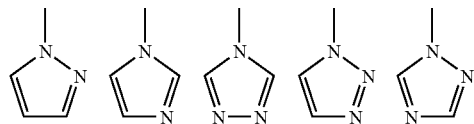

Another preferred embodiment of the instant invention relates to compounds of formula I and preferably one or more of sub formulae I.1) to I.20), wherein $(R^8)_p$—$Ar^1$ is as defined above, but comprises one or more additional residues, preferably one additional residue. The additional residues are preferably selected from the meanings given for $R^7$ and more preferably from

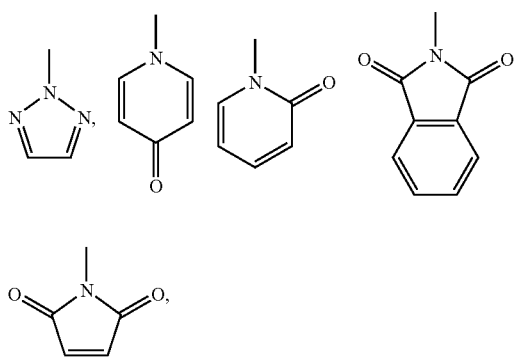

and/or

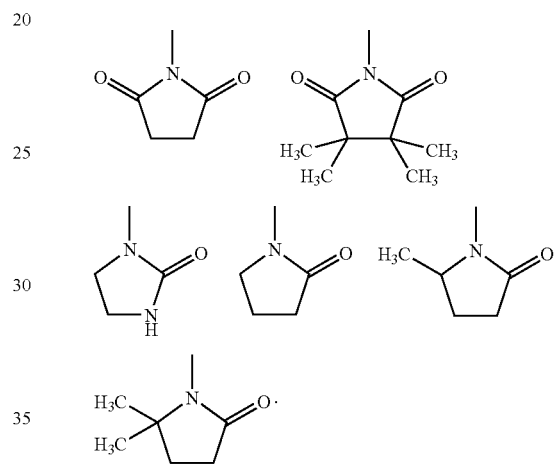

Another preferred embodiment of the instant invention relates to compounds of formula I and preferably one or more of sub formulae I.1) to I.20), wherein $(R^8)_p$—$Ar^1$ is as defined above, but comprises one or more additional residues, preferably one additional residue. The additional residues are preferably selected from the meanings given for $R^7$ and more preferably from

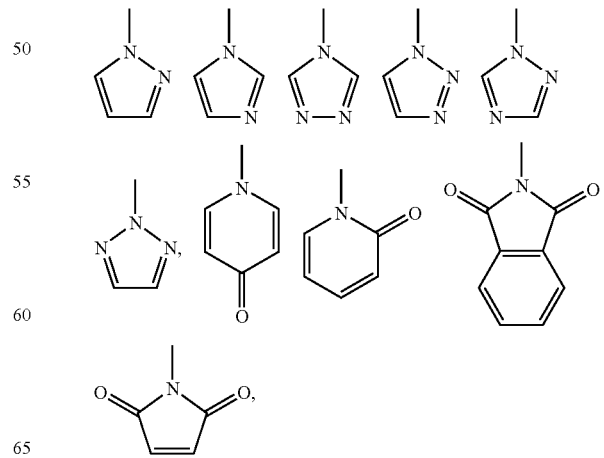

and/or

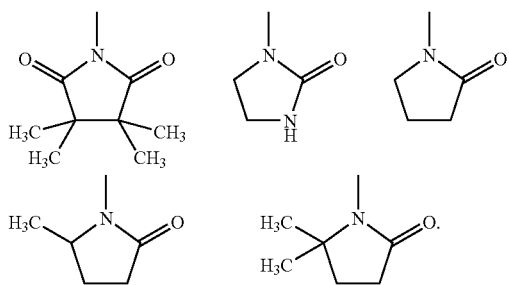

Another preferred embodiment of the instant invention relates to compounds of formula I and the subformulae related thereto and preferably one or more of formulae I.1) to I.20), wherein the residues $Ar^3$—$(R^{10})_r$ are selected from the group consisting of the following formulae:

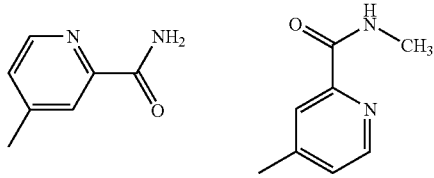

and/or residues of the structures given above that comprise one or two, preferably one additional substituent, independently selected from the meanings given for $R^{10}$.

Another preferred embodiment of the instant invention relates to compounds of formula I and the subformulae related thereto and preferably one or more of formulae I.1) to I.20), wherein the residues $(R^8)_p$—$Ar^1$—$(R^{17})_g$ are selected from the following formulae:

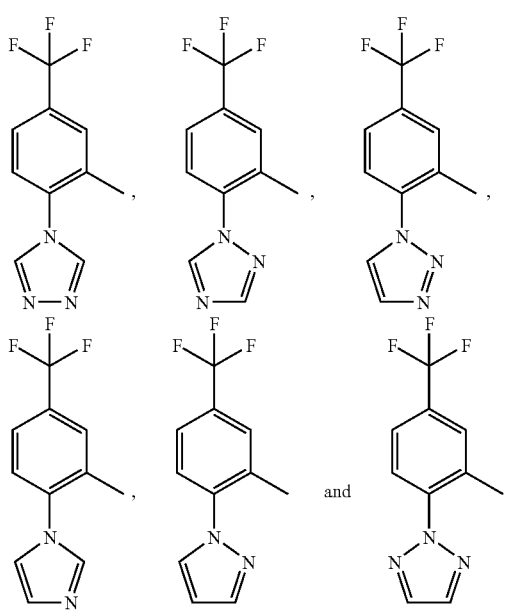

and/or residues of the structures given above that comprise one or two, preferably one additional substituent, independently selected from the meanings given for $R^7$ and/or $R^8$.

Another preferred embodiment of the instant invention relates to compounds of formula A-NH—CO—NH—B, wherein A is selected from the meanings of $(R^8)_p$—$Ar^1$—$(R^7)_g$ as defined in the paragraph related thereto above, and B is selected from formulae

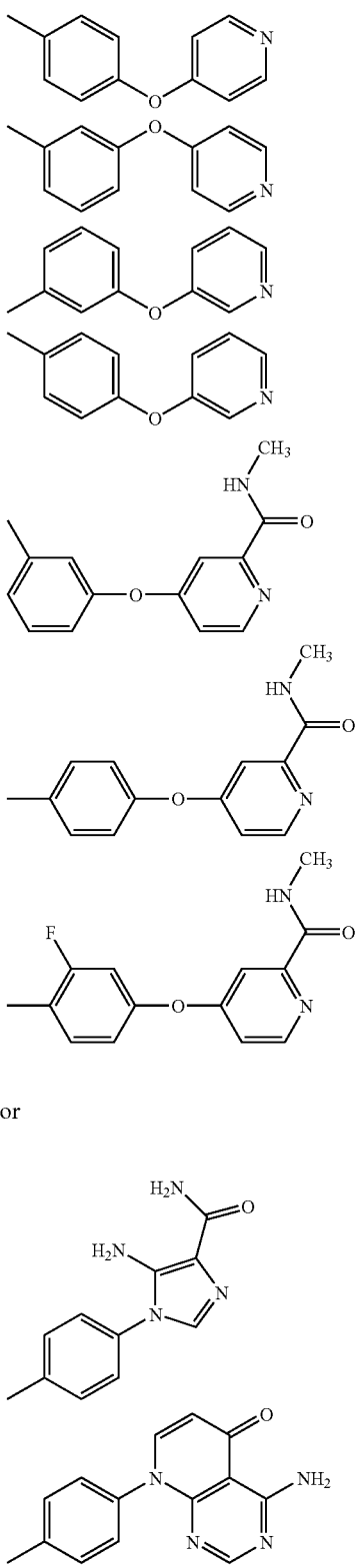

and/or

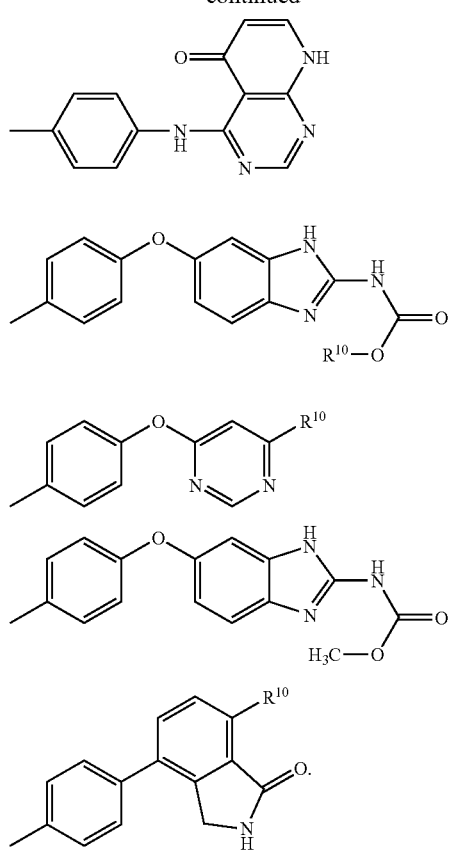

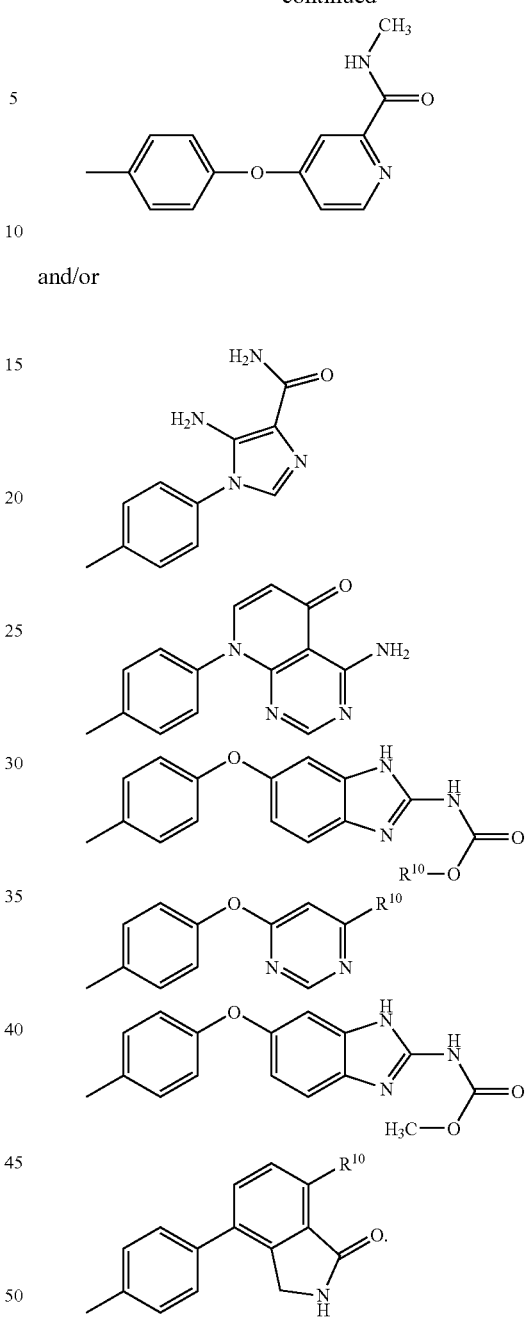

Another preferred embodiment of the instant invention relates to compounds of formula A-NH—CO—NH—B, wherein A is selected from the meanings of $(R^8)_p$—$Ar^1$—$(R^7)_g$ as defined in the paragraph above related thereto, and B is selected from formulae

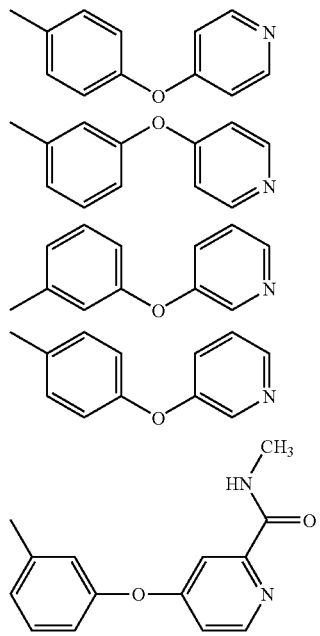

Another preferred embodiment of the instant invention relates to compounds of formula A-NH—CO—NH—B, wherein B is selected from one or more of the two paragraphs above relating thereto, and A is a group of the formula $(R^8)_p$—$Ar^1$—$(R^7)_g$ which is preferably selected from

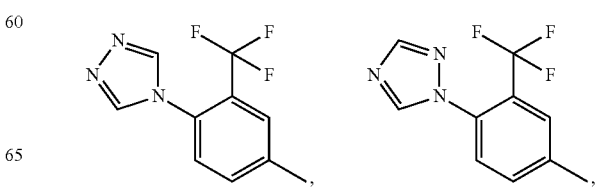

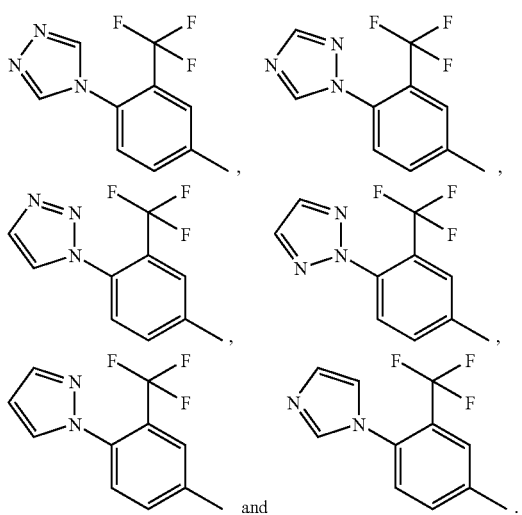

and especially selected from

Another preferred embodiment of the instant invention relates to compounds of formula I and preferably one or more of sub formulae I.1) to I.20), wherein X is bonded in the para- (p-) or metha- (m-) position to the 6-membered aromatic, E, G, M, Q and U containing group that is bonded directly to the urea moiety.

Another preferred embodiment of the instant invention relates to compounds of formula I and preferably one or more of sub formulae I.1) to I.20), wherein $Ar^3$ is a pyridinyl residue and wherein said pyridinyl residue is bonded to X in the 3- or 4-position, preferably the 4-position, relative to the nitrogen atom of the pyridinyl residue.

Another preferred embodiment of the instant invention relates to compounds of formula I and preferably one or more of sub formulae I.1) to I.20), wherein $Ar^1$ comprises one or more substituents $R^8$ and wherein one or two, preferably one substituent $R^8$ is selected from the group consisting of $SO_2CH_3$, $SO_2CF_3$, $OSO_2CH_3$, $OSO_2CF_3$, $SO_2NH_2$, $SO_2NHCH(CH_3)_2$, $SO_2N(CH_3)_2$, $SO_2N(CH_2CH_3)_2$ and 4-Morpholine-4-sulfonyl.

Another preferred embodiment of the instant invention relates to compounds of formula I and preferably the sub formulae related thereto, wherein $Ar^3$ does not comprise two or more fused 6-membered ringsystems (i.e it does not comprise two or more 6-membered ringsystems fused (or anelated) to each other).

Another preferred embodiment of the instant invention relates to compounds of formula I and preferably the sub formulae related thereto, wherein $Ar^3$ does not comprise a 6-membered and a 5-membered ringsystems fused (or anelated) to each other.

Another preferred embodiment of the instant invention relates to compounds of formula I and preferably the sub formulae related thereto, wherein $Ar^3$ does not comprise fused or anelated ringsystems.

Another preferred embodiment of the instant invention relates to compounds of formula I and preferably one or more of sub formulae I.1) to I.20), wherein $Ar^3$ comprises one or more substituents $R^{10}$ and wherein one or two, preferably one substituent $R^{10}$ is selected from unsubstituted or substituted carbamoyl moieties. Substituted carbamoyl moieties are preferably selected from $CONHR^{23}$ or $CONR^{23}R^{24}$, preferably $CONHR^{23}$, wherein $R^{23}$ and $R^{24}$ are independently selected from the definitions given for $R^8$, more preferably selected from alkyl, preferably methyl, ethyl, propyl and butyl, $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of methyl, ethyl, $CH_2CH_2NH_2$, $CH_2CH_2N(CH_3)_2$, $CH_2CH_2N(CH_2CH_3)_2$, $CH_2CH_2OH$, $CH_2CH_2OCH_3$ and $CH_2CH_2OCH_2CH_3$.

Another preferred embodiment of the instant invention relates to compounds of formula I and preferably one or more of sub formulae I.1) to I.20), wherein $Ar^3$ comprises one or more substituents $R^{10}$ and wherein one or two, preferably one substituent $R^{10}$ is selected from substituted carbamoyl moieties. Substituted carbamoyl moieties are preferably selected from $CONHR^{23}$, wherein $R^{23}$ is preferably unsubstituted $C_1$-$C_4$-alkyl and especially methyl.

Another preferred embodiment of the instant invention relates to compounds of formula I and preferably one or more of sub formulae I.1) to I.20), wherein $Ar^3$ comprises one or more substituents $R^1$ and wherein one or two, preferably one substituent $R^{10}$ is selected from substituted carbamoyl moieties. Substituted carbamoyl moieties are preferably selected from $CONHR^{23}$, wherein $R^{23}$ is selected from $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of $CH_2CH_2NH_2$, $CH_2CH_2N(CH_3)_2$, $CH_2CH_2N(CH_2CH_3)_2$, $CH_2CH_2OH$, $CH_2CH_2OCH_3$ and $CH_2CH_2OCH_2CH_3$.

Another preferred embodiment of the instant invention relates to compounds of formula I and preferably one or more of sub formulae I.1) to I.20), wherein —Ar³—(R¹⁰) is selected from the formulae

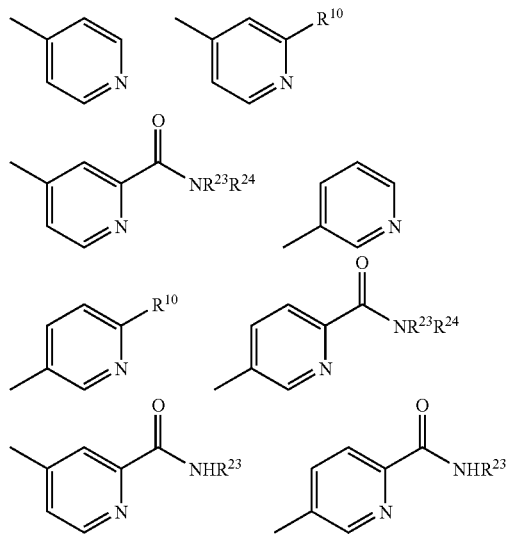

wherein R¹⁰, R²³ and R²⁴ are as defined above and below.

Another preferred embodiment of the instant invention relates to compounds of formula I and preferably the subformulae related thereto, wherein R⁷ is 3-Oxo-2-aza-bicyclo [2.2.2]oct-2-yl.

Another preferred embodiment of the instant invention relates to compounds of formula I and preferably the subformulae related thereto, wherein R⁷ is 3-Methyl-2,5-dioxo-imidazolidin-1-yl.

Another preferred embodiment of the instant invention relates to compounds of formula I and preferably the subformulae related thereto, wherein R⁷ is 2-Oxo-oxazolidin-3-yl.

Another preferred embodiment of the instant invention relates to compounds of formula I and preferably the subformulae related thereto, wherein R⁹ is Hal, preferably F, and q is as defined above/below and preferably is 1.

Another preferred embodiment of the instant invention relates to compounds of formula I and preferably the sub formulae related thereto, wherein the residues R⁷ do not comprise OH, NH and/or NH₂ groups.

Another preferred embodiment of the instant invention relates to compounds of formula I and the sub formulae related thereto, wherein the residues R⁸ do not comprise OH, NH and/or NH₂ groups.

Another preferred embodiment of the instant invention relates to compounds of formula I and the sub formulae related thereto, wherein the residues R⁹ do not comprise OH, NH and/or NH₂ groups.

Another preferred embodiment of the instant invention relates to compounds of formula I and preferably the sub formulae related thereto, wherein Ar¹ and/or Ar² (and the 6-membered aromatic, E, G, M, Q and U containing group or phenyl group bound to the urea moiety that are preferred meanings of Ar², respectively), do not comprise a OH group in the ortho position to the urea moiety.

Another preferred embodiment of the instant invention relates to compounds of formula I and preferably the sub formulae related thereto, wherein Ar¹ and/or Ar² (and the 6-membered aromatic, E, G, M, Q and U containing group or phenyl group bound to the urea moiety that are preferred meanings of Ar², respectively), do not comprise a —NHSO₂— moiety in the ortho position to the urea moiety.

Another preferred embodiment of the instant invention relates to compounds of formula I and preferably the sub formulae related thereto, wherein Ar¹ and/or Ar² (and the 6-membered aromatic, E, G, M, Q and U containing group or phenyl group bound to the urea moiety that are preferred meanings of Ar², respectively), do not comprise a moiety in the ortho position to the urea moiety having an ionizable hydrogen and a pKa of 10 or less.

Another preferred embodiment of the instant invention relates to compounds of formula I and preferably the sub formulae related thereto, wherein both the aromatic groups bound directly to the urea moiety do not comprise a substituent in the ortho position to the urea moiety, selected from OH, substituents comprising a —NHSO₂— moiety, and substituents comprising moieties having an ionizable hydrogen and a pKa of 10 or less.

Another preferred embodiment of the instant invention relates to compounds of formula I and preferably the subformulae related thereto, wherein R⁷ is not a 2,5-dimethylpyrrol-1-yl moiety that is bonded in the ortho position relative to the urea moiety Ar¹ is bonded to.

Another preferred embodiment of the instant invention relates to compounds of formula I and preferably the subformulae related thereto, wherein R⁷, R⁸, R⁹ and/or Het⁹ is not 2,5-dimethylpyrrol-1-yl.

Another preferred embodiment of the instant invention relates to compounds of formula I and preferably the subformulae related thereto, wherein R⁷, R⁸, R⁹ and/or Het⁹ is not a substituted and/or unsubstituted pyrrol-1-yl moiety.

Another preferred embodiment of the instant invention relates to compounds of formula I and preferably the subformulae related thereto, wherein R⁷ is not 2,5-dimethylpyrrol-1-yl.

Another preferred embodiment of the instant invention relates to compounds of formula I and preferably the subformulae related thereto, wherein R⁷ is not a substituted and/or unsubstituted pyrrol-1-yl moiety.

Another especially preferred embodiment of the instant invention relates to compounds of formula I, preferably the sub formulae related thereto and more preferably one or more of the sub formulae I.1) to I.20) and/or Ia to Iz, wherein one or more features of the above and below mentioned embodiments are combined in one compound.

Another especially preferred embodiment of the instant invention relates to compounds of formula I, preferably the sub formulae related thereto and more preferably one or more of the sub formulae I.1) to I.20), Iaa to Iss and/or Itt to Iww, wherein one or more features of the above and below mentioned embodiments are combined in one compound.

Subject of the present invention are therefore preferably compounds of formula I according to one or both of the formulae Ia and Ib, Ia

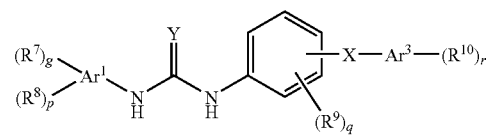

Ib

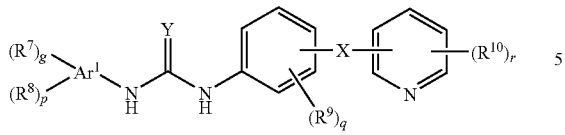

wherein Ar¹, R⁷, R⁸, p, g, Y, X, R⁹, q, Ar³, R¹⁰ and r are as defined above and below, and preferably as defined in sub formulae I.1) to I.20) and/or the embodiments related thereto, and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Subject of the present invention are therefore especially preferred compounds of formula I according to one or both or more of the formulae Ic, Id and Ie, Ic

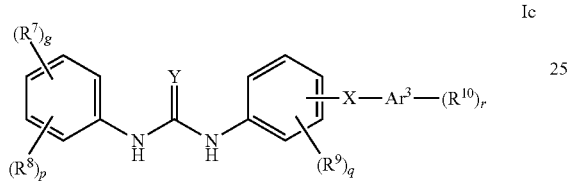

Id

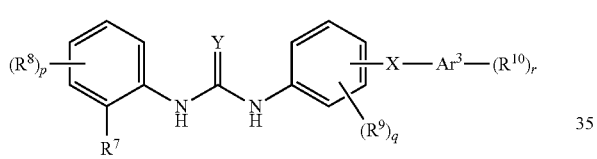

Ie

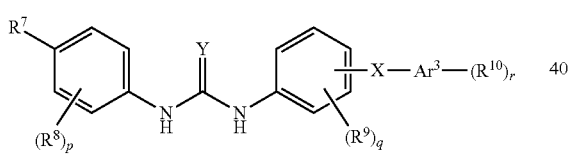

wherein R⁷, g, R⁸, p, Y, X, R⁹, q, Ar³ and R¹⁰ are as defined above and below, preferably R¹⁰ is as defined in sub formulae I.1) to I.20) and/or the embodiments related thereto;
and/or compounds of formula I according to one or more of the formulae If to Iz, If

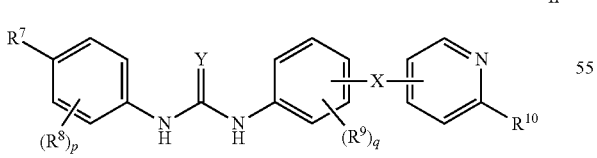

Ig

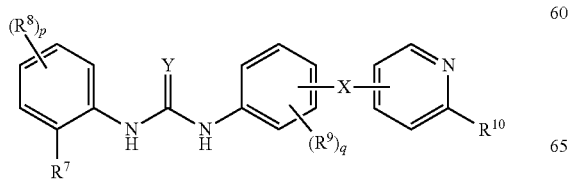

Ih

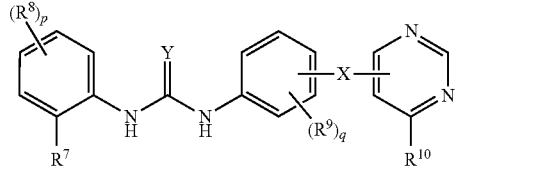

Ii

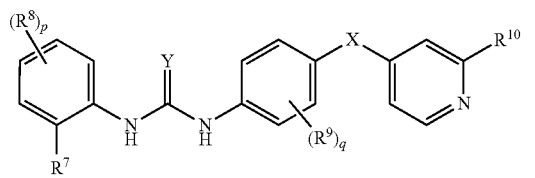

Ij

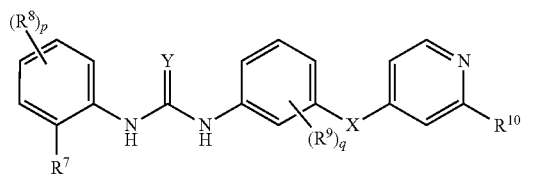

Ik

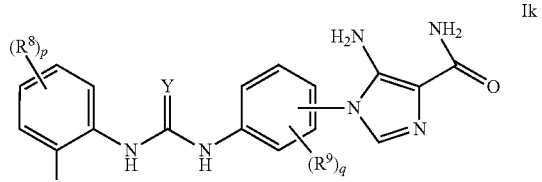

IL

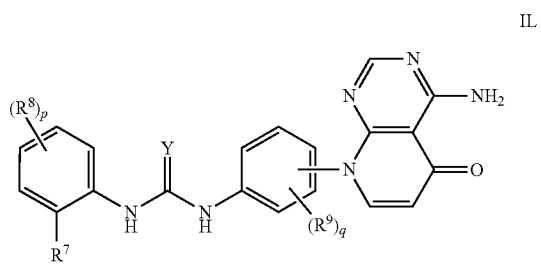

Im

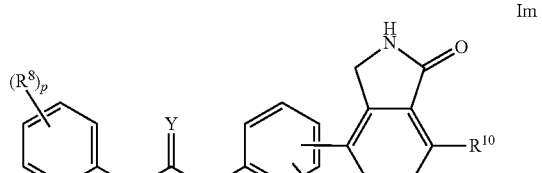

In

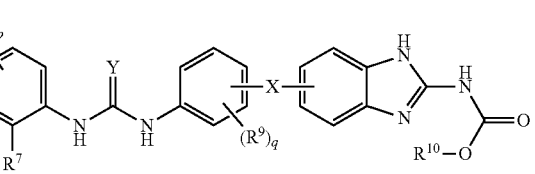

Io
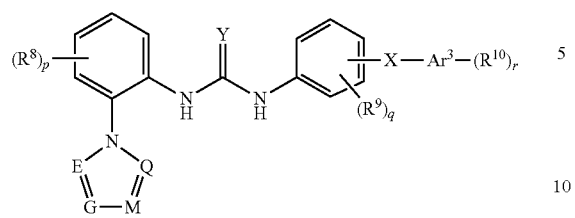
Ip
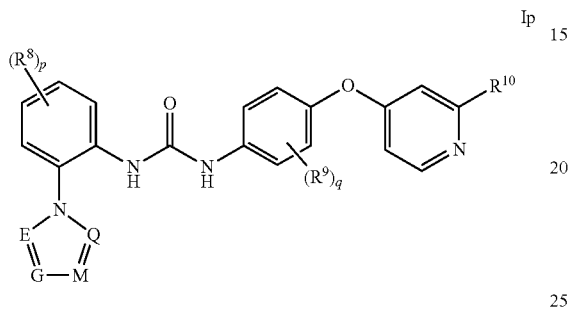
Iq
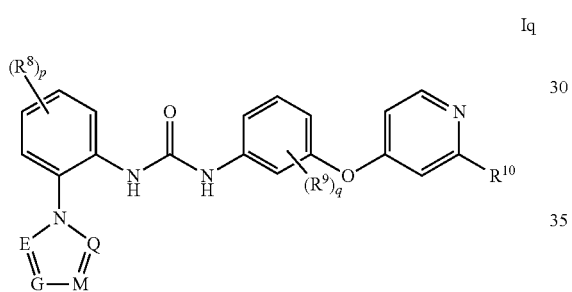
Ir
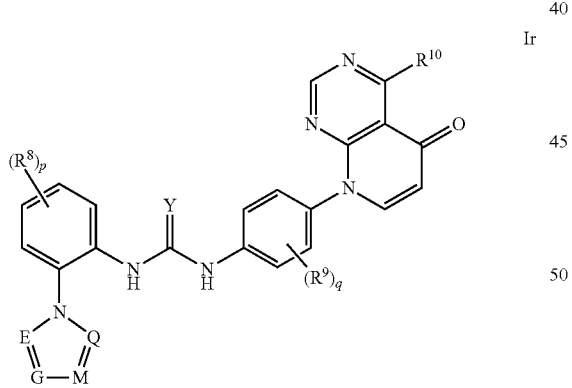
Is
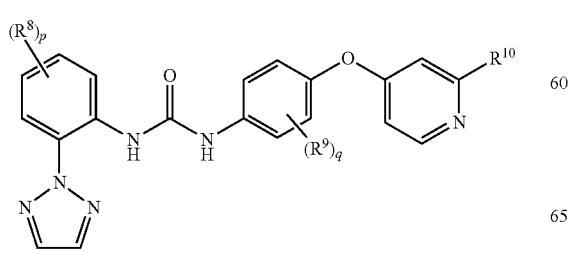
It
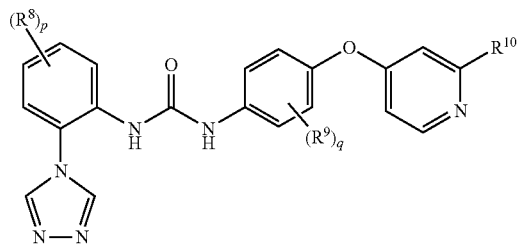
Iu
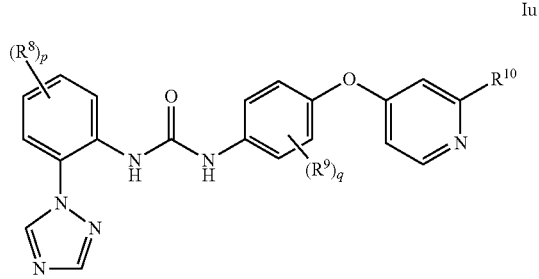
Iv
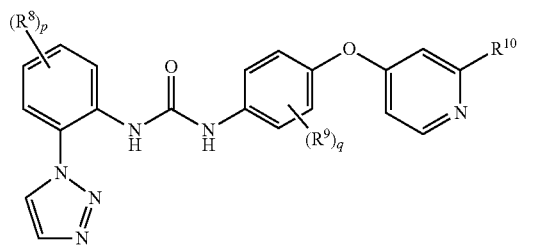
Iw
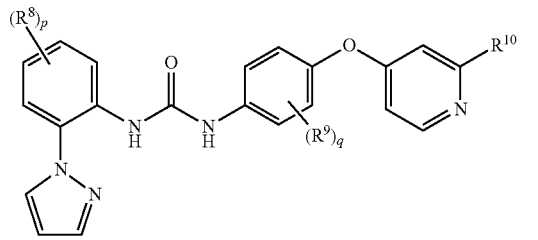
Ix
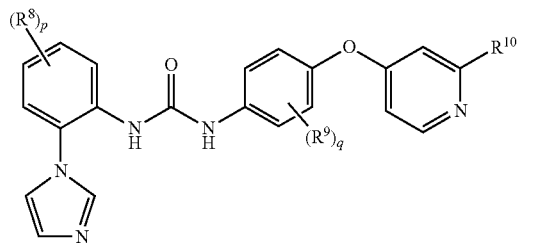
Iy
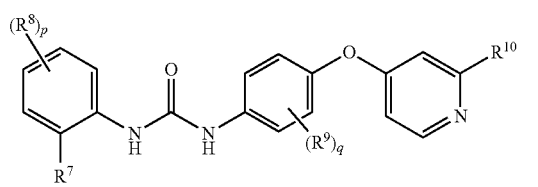

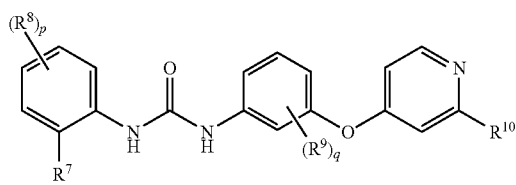
Iz wherein $R^7$, $R^8$, $Ar^3$, Y, X, $R^9$, p, q and $R^{10}$ are as defined above and below, more preferably $R^{10}$ is H or as defined above/below, and preferably as defined in sub formulae I.1) to I.20) and/or the embodiments related thereto, and wherein E, G, M and Q are selected independently from one another from N and $CR^{30}$ and especially from N and CH; with the proviso that one or more, preferably two or more and especially two or three of E, G, M and Q are other than nitrogen atoms; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Subject of the present invention are therefore especially preferred compounds of formula I according to one or more of the formulae Iaa to Iss

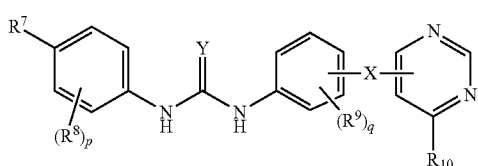
Iaa

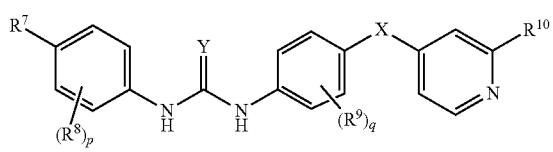
Ibb

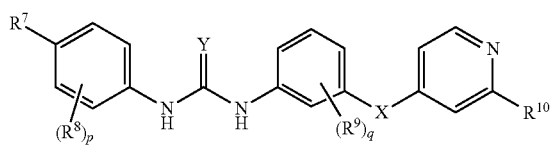
Icc

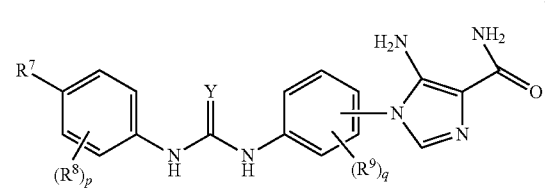
Idd

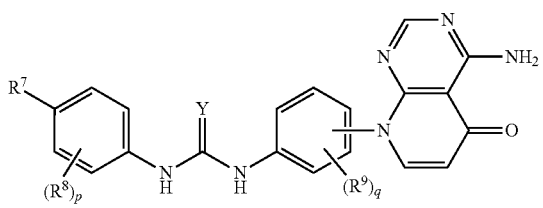
Iee

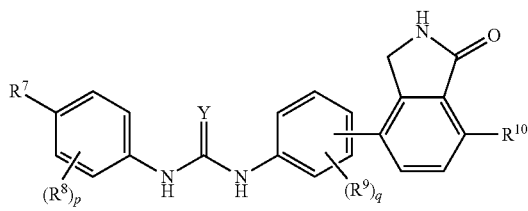
Iff

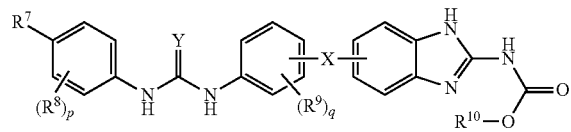
Igg

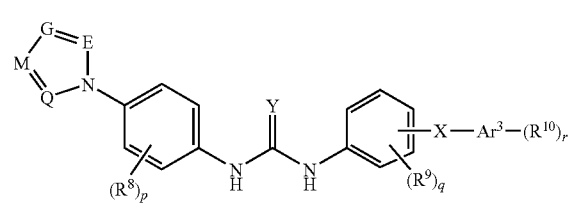
Ihh

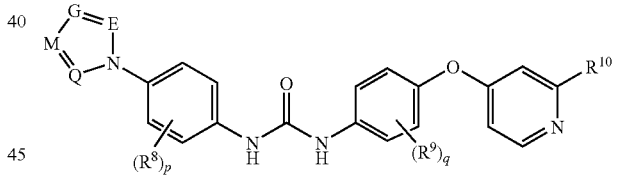
Iii

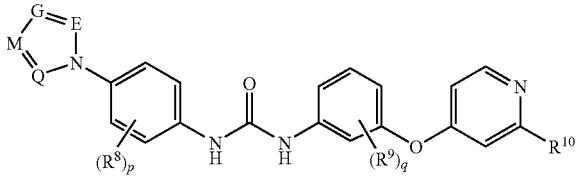
Ijj

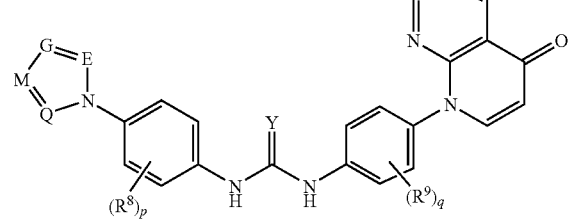
Ikk

-continued

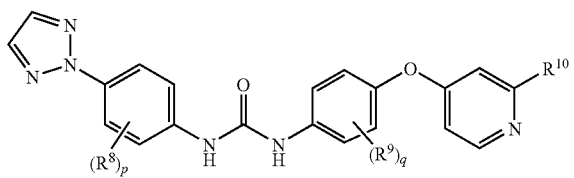
Ill

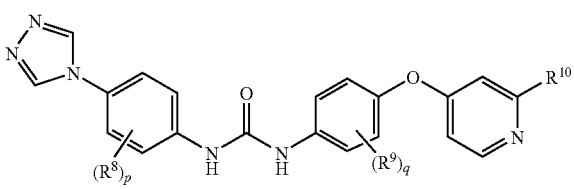
Imm

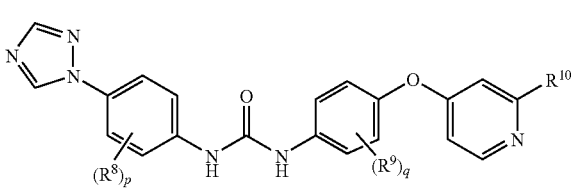
Inn

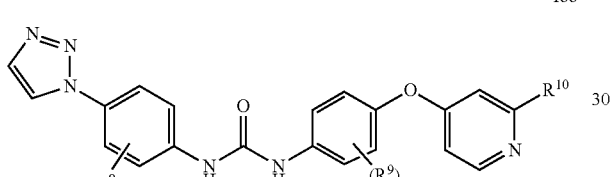
Ioo

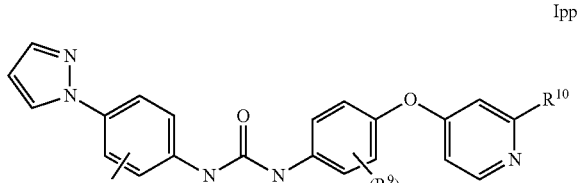
Ipp

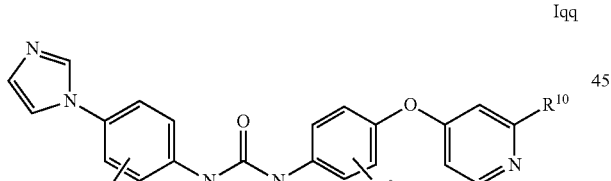
Iqq

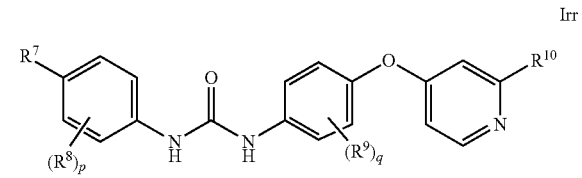
Irr

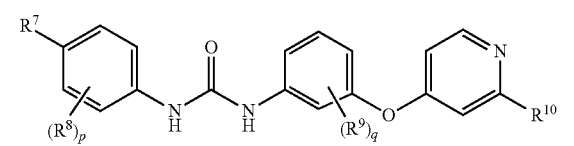
Iss wherein $R^7$, $R^8$, $Ar^3$, Y, X, $R^9$, p, q and $R^{10}$ are as defined above and below, more preferably $R^{10}$ is H or as defined above/below, and preferably as defined in sub formulae I.1) to I.20) and/or the embodiments related thereto, and wherein E, G, M and Q are selected independently from one another from N and $CR^{30}$ and especially from N and CH; with the proviso that one or more, preferably two or more and especially two or three of E, G, M and Q are other than nitrogen atoms; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Subject of the present invention are therefore especially preferred compounds of formula I according to one or more of the formulae Itt to Iww

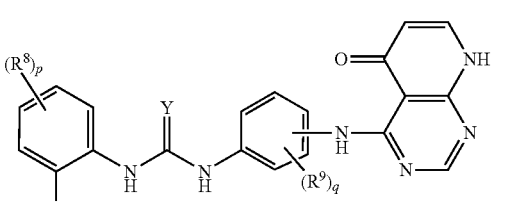
Itt

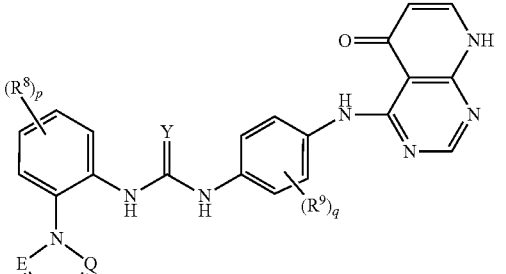
Iuu

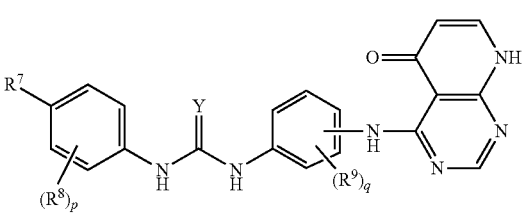
Ivv

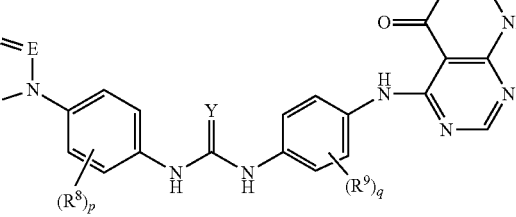
Iww wherein $R^7$, $R^8$, Y, $R^9$, p and q are as defined above and below, preferably as defined in sub formulae I.1) to I.20) and/or the embodiments related thereto, and wherein E, G, M and Q are selected independently from one another from N and $CR^{30}$ and especially from N and CH; with the proviso that one or more, preferably two or more and especially two or three of E, G, M and Q are other than nitrogen atoms; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Another preferred embodiment of the instant invention relates to compounds of formula I and preferably one or more of sub formulae I.1) to I.20) and Ib, Ie, If, Ig, Ih, In, Io, Iq, Ir, Is, It, Iu, Iv, Iw, Ix, Iy and Iz, wherein $R^{10}$ is a substituted carbamoyl moiety CONHR$^{23}$ or CONR$^{23}$R$^{24}$, preferably CONHR$^{23}$, wherein $R^{23}$ and $R^{24}$ are independently selected from the definitions given for $R^8$, more preferably selected from CH$_3$ and (CH$_2$)$_n$NR$^{11}$R$^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of CH$_3$, CH$_2$CH$_2$NH$_2$, CH$_2$CH$_2$N(CH$_3$)$_2$, CH$_2$CH$_2$N(CH$_2$CH$_3$)$_2$, CH$_2$CH$_2$OH, CH$_2$CH$_2$OCH$_3$ and CH$_2$CH$_2$OCH$_2$CH$_3$. Preferably, this embodiment also relates to one or more of sub formulae Iaa, Ibb, Icc, and Igg to Iss.

Another preferred embodiment of the instant invention relates to compounds of formula I and preferably one or more of sub formulae I.1) to I.20) and Ia to In, Iy and Iz, wherein $R^7$ is selected from [1,2,3]triazol-2-yl, [1,2,4]triazol-4-yl, [1,2,4]triazol-1-yl, [1,2,3]triazol-1-yl, 2-imidazol-1-yl, 2-pyrazol-1-yl, phthalimido-1-yl, succinimido-1-yl, maleinimido-1-yl, pyrrolidin-2-on-1-yl, pyridin-2-on-1-yl, pyridin-4-on-1-yl, pyrrolidin-2,5-dion-1-yl, 3,3',4,4'-tetramethyl-pyrrolidin-2,5-dion-1-yl, 5-methyl-pyrrolidin-2-on-1-yl, 5,5'-dimethyl-pyrrolidin-2-on-1-yl, and imiazolidin-2-on-1-yl. Preferably, this embodiment also relates to one or more of sub formulae Iaa to Igg, Irr and Iss. Preferably, this embodiment also relates to one or more of sub formulae Itt and Ivv.

Another especially preferred embodiment of the instant invention relates to compounds of formula I and preferably one or more of sub formulae I.1) to I.20) and Ia to In, Iy and Iz, wherein $R^7$ is selected from [1,2,3]triazol-2-yl, [1,2,4]triazol-4-yl, [1,2,4]triazol-1-yl, [1,2,3]triazol-1-yl, 2-imidazol-1-yl, 2-pyrazol-1-yl, phthalimido-1-yl, maleinimido-1-yl, pyrrolidin-2-on-1-yl, pyridin-2-on-1-yl, pyridin-4-on-1-yl, pyrrolidin-2,5-dion-1-yl, 3,3',4,4'-tetramethyl-pyrrolidin-2,5-dion-1-yl, 5-methyl-pyrrolidin-2-on-1-yl, 5,5'-dimethyl-pyrrolidin-2-on-1-yl, and imiazolidin-2-on-1-yl. Preferably, this embodiment also relates to one or more of sub formulae Iaa to Igg, Irr and Iss. Preferably, this embodiment also relates to one or more of sub formulae Itt and Ivv.

Another preferred embodiment of the instant invention relates to compounds of sub formulae Im, In and Ip, wherein in each case $R^{10}$ is independently selected from H, Hal, A, NR$^{11}$R$^{12}$ and NH$_2$. Preferably, this embodiment also relates to one or more of sub formulae Iff, Igg, Iii and Ikk.

It is understood that when a residue, for example $R^8$, $R^9$, $R^{10}$, $R^{14}$ or $R^{23}$, is comprised twice or more times in one or more of the formulae I and the sub formulae corresponding thereto, it is in each case independently from one another selected from the meanings given for the respective residue. For example, $R^{11}$ and $R^{12}$ are defined to be independently selected from a group consisting of H, A, (CH$_2$)$_m$Ar$^7$ and (CH$_2$)$_m$Het$^9$. Then (CH$_2$)$_n$NR$^{11}$(CH$_2$)$_m$NR$^{12}$R$^{12}$ can be (CH$_2$)$_n$NA(CH$_2$)$_m$NA$_2$ (if R$^{11}$=A, R$^{12}$=A and R$^{12}$=H) as well as (CH$_2$)$_n$NA(CH$_2$)$_m$NHA (if R$^{11}$=A, R$^{12}$=H and R$^{12}$=A) or (CH$_2$)$_n$NA(CH$_2$)$_m$NH(CH$_{2m}$)Het$^9$ (if R$^{11}$=A, R$^{12}$=H and R$^{12}$=(CH$_2$)$_m$Het$^9$). Accordingly, if a compound of formula I comprises one residue $R^8$, $R^9$ and $R^{10}$, then for example $R^8$, $R^9$ and $R^{10}$ can all be (CH$_2$)$_n$COOR$^{13}$, wherein all residues $R^{13}$ are the same (for example CH$_2$Hal, wherein Hal is Cl; then all residues $R^8$, $R^9$ and $R^{10}$ are the same) or different (for example CH$_2$Hal, wherein in $R^8$ Hal is Cl; in $R^9$ Hal is F; and in $R^{10}$ Hal is Br; then all residues $R^8$, $R^9$ and $R^{10}$ are different); or for example $R^8$ is (CH$_2$)$_n$COOR$^{13}$, $R^9$ is NO$_2$ and $R^{10}$ is (CH$_2$)$_n$SR$^{11}$, wherein $R^{11}$ and $R^{13}$ can be the same (for example both can be H or both can be A which is methyl) of different (for example $R^{11}$ can be H and $R^{13}$ can be A which is methyl).

If not stated otherwise, reference to compounds of formula I preferably also includes the sub formulae related thereto, especially sub formulae I.1) to I.20) and Ia to Iz.

If not stated otherwise, reference to compounds of formula I preferably also includes the sub formulae related thereto, especially sub formulae Iaa to Iss and/or Itt to Iww.

Subject of the instant invention are especially those compounds of formula I and preferably also the sub formulae related thereto, in which at least one of the residues mentioned in said formulae has one of the preferred or especially preferred meanings given above and below.

Especially preferred as compounds according to the invention are the compounds given below:

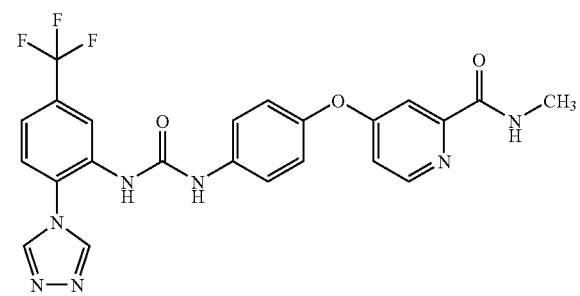

4-{4-[3-(2-[1,2,4]Triazol-4-yl-5-trifluoromethyl-phenyl)-ureido]-phenoxy}-pyridine-2-carboxylic acid methylamide,

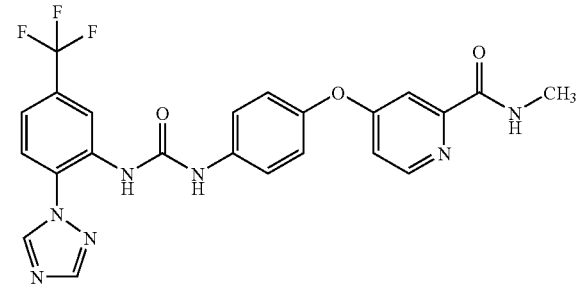

4-{4-[3-(2-[1,2,4]Triazol-1-yl-5-trifluoromethyl-phenyl)-ureido]-phenoxy}-pyridine-2-carboxylic acid methylamide,

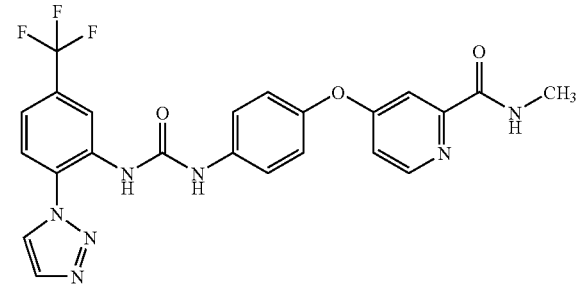

4-{4-[3-(2-[1,2,3]Triazol-1-yl-5-trifluoromethyl-phenyl)-ureido]-phenoxy}-pyridine-2-carboxylic acid methylamide,

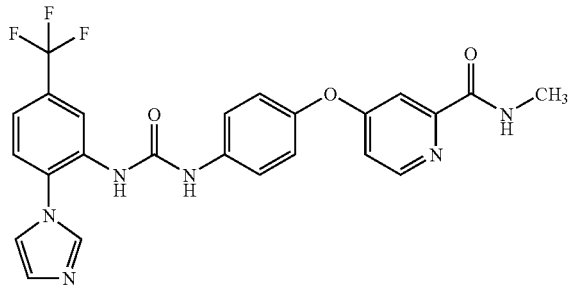

4-{4-[3-(2-Imidazol-1-yl-5-trifluoromethyl-phenyl)-ureido]-phenoxy}-pyridine-2-carboxylic acid methylamide,

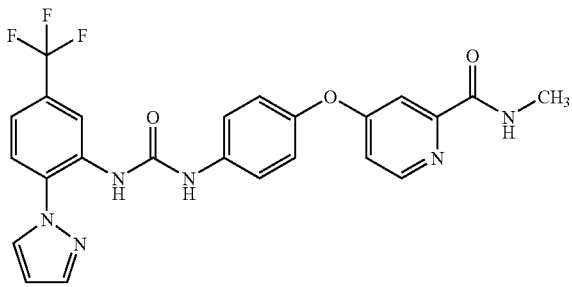

4-{4-[3-(2-Pyrazol-1-yl-5-trifluoromethyl-phenyl)-ureido]-phenoxy}-pyridine-2-carboxylic acid methylamide,

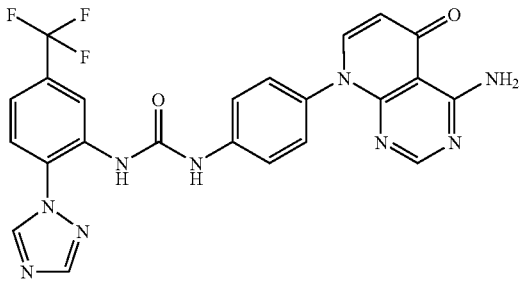

1-[4-(4-Amino-5-oxo-5H-pyrido[2,3-d]pyrimidin-8-yl)-phenyl]-3-(2-[1,2,4]triazol-1-yl-5-trifluoromethyl-phenyl)-urea;

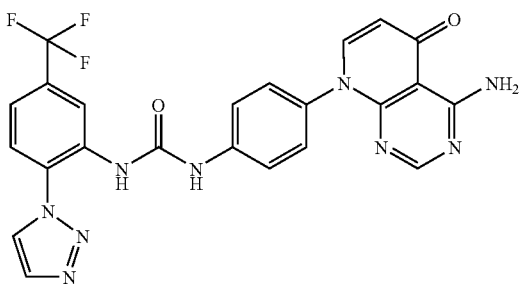

1-[4-(4-Amino-5-oxo-5H-pyrido[2,3-d]pyrimidin-8-yl)-phenyl]-3-(2-[1,2,3]triazol-1-yl-5-trifluoromethyl-phenyl)-urea;

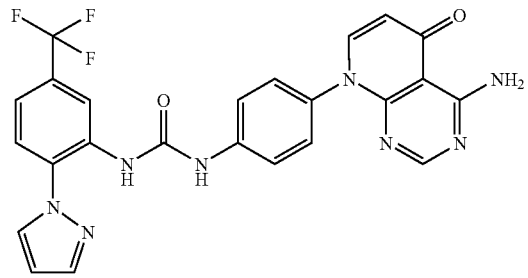

1-[4-(4-Amino-5-oxo-5H-pyrido[2,3-d]pyrimidin-8-yl)-phenyl]-3-(2-pyrazol-1-yl-5-trifluoromethyl-phenyl)-urea

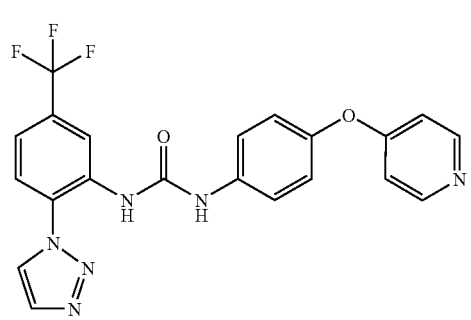

1-[4-(Pyridin-4-yloxy)-phenyl]-3-(2-[1,2,3]triazol-1-yl-5-trifluoromethyl-phenyl)-urea;

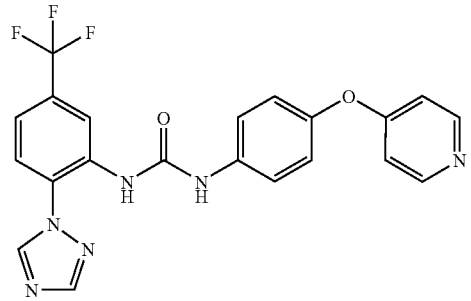

1-[4-(Pyridin-4-yloxy)-phenyl]-3-(2-[1,2,4]triazol-1-yl-5-trifluoromethyl-phenyl)-urea;

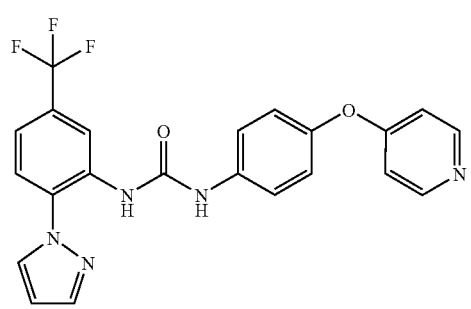

1-(2-Pyrazol-1-yl-5-trifluoromethyl-phenyl)-3-[4-(pyridin-4-yloxy)-phenyl]-urea;

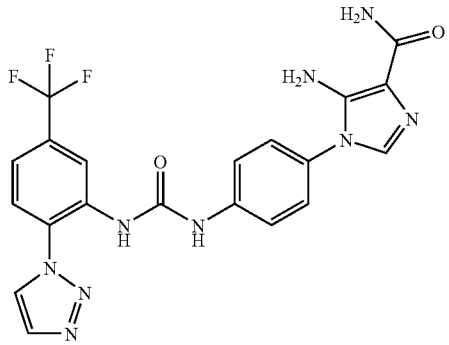

5-Amino-1-{4-[3-(2-[1,2,3]triazol-1-yl-5-trifluoromethyl-phenyl)-ureido]-phenyl}-1H-imidazole-4-carboxylic acid amide;

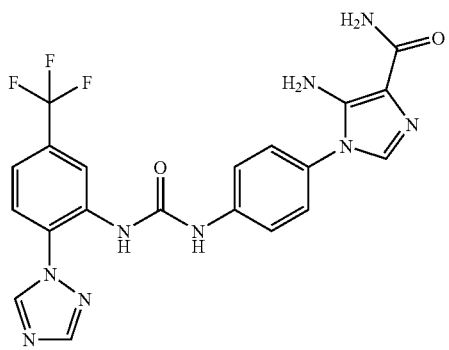

5-Amino-1-{4-[3-(2-[1,2,4]triazol-1-yl-5-trifluoromethyl-phenyl)-ureido]-phenyl}-1H-imidazole-4-carboxylic acid amide;

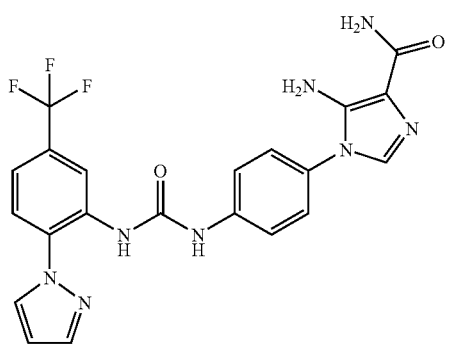

5-Amino-1-{4-[3-(2-pyrazol-1-yl-5-trifluoromethyl-phenyl)-ureido]-phenyl}-1H-imidazole-4-carboxylic acid amide;

and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Further especially preferred compounds according to the invention are selected from the compounds given below:

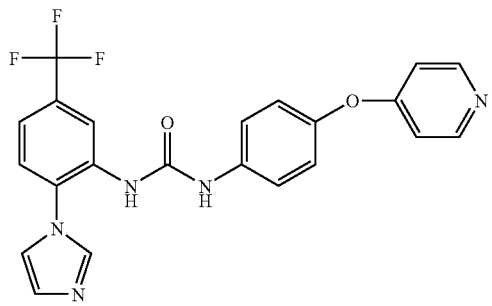

1-(2-Imidazol-1-yl-5-trifluoromethyl-phenyl)-3-[4-(pyridin-4-yloxy)-phenyl]-urea;

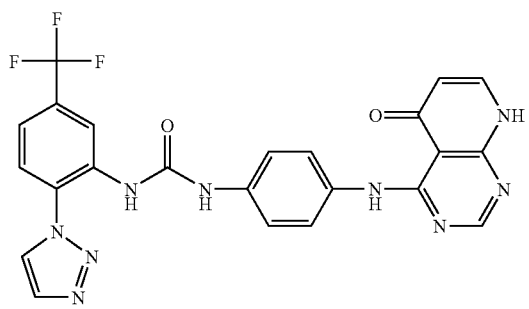

1-[4-(5-Oxo-5,8-dihydro-pyrido[2,3-d]pyrimidin-4-ylamino)-phenyl]-3-(2-[1,2,3]triazol-1-yl-5-trifluoromethyl-phenyl)-urea;

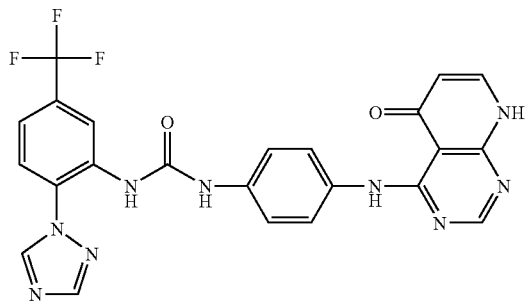

1-[4-(5-Oxo-5,8-dihydro-pyrido[2,3-d]pyrimidin-4-ylamino)-phenyl]-3-(2-[1,2,4]triazol-1-yl-5-trifluoromethyl-phenyl)-urea;

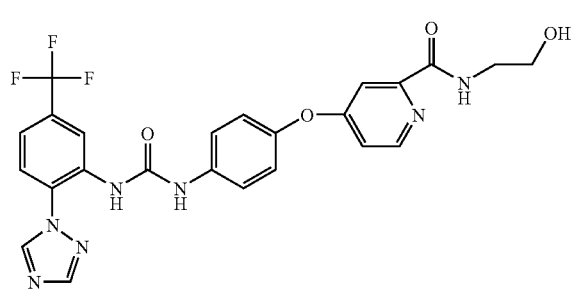

4-{4-[3-(2-[1,2,4]Triazol-1-yl-5-trifluoromethyl-phenyl)-ureido]-phenoxy}-pyridine-2-carboxylic acid (2-hydroxy-ethyl)-amide;

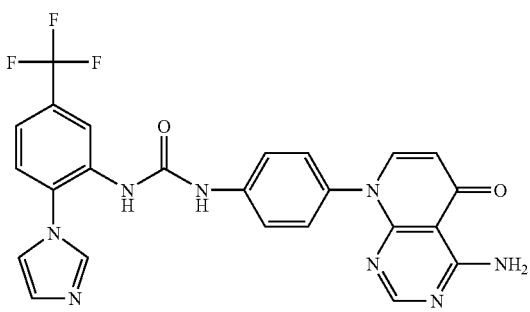

1-[4-(4-Amino-5-oxo-5H-pyrido[2,3-d]pyrimidin-8-yl)-phenyl]-3-(2-imidazol-1-yl-5-trifluoromethyl-phenyl)-urea;

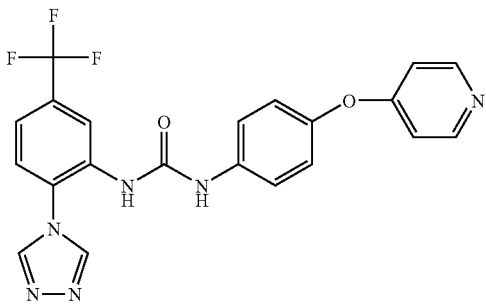

1-[4-(Pyridin-4-yloxy)-phenyl]-3-(2-[1,2,4]triazol-4-yl-5-trifluoromethyl-phenyl)-urea;

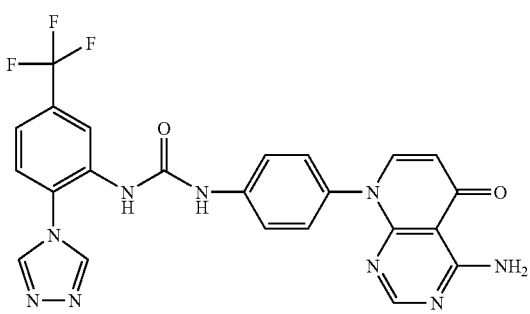

1-[4-(4-Amino-5-oxo-5H-pyrido[2,3-d]pyrimidin-8-yl)-phenyl]-3-(2-[1,2,4]triazol-4-yl-5-trifluoromethyl-phenyl)-urea;

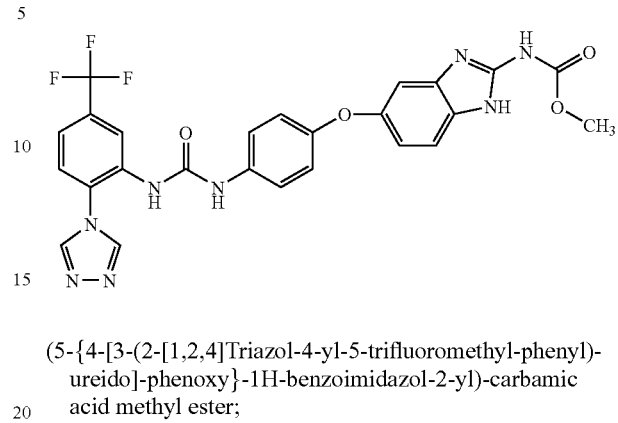

(5-{4-[3-(2-[1,2,4]Triazol-4-yl-5-trifluoromethyl-phenyl)-ureido]-phenoxy}-1H-benzoimidazol-2-yl)-carbamic acid methyl ester;

(5-{4-[3-(2-[1,2,3]Triazol-1-yl-5-trifluoromethyl-phenyl)-ureido]-phenoxy}-1H-benzoimidazol-2-yl)-carbamic acid methyl ester;

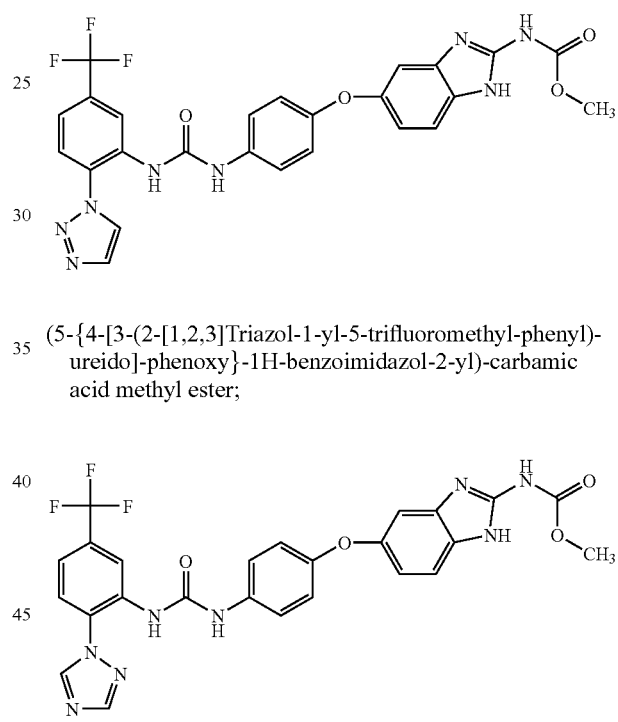

(5-{4-[3-(2-[1,2,4]Triazol-1-yl-5-trifluoromethyl-phenyl)-ureido]-phenoxy}-1H-benzoimidazol-2-yl)-carbamic acid methyl ester;

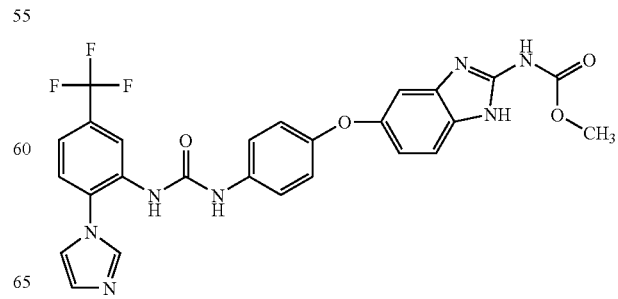

(5-{4-[3-(2-Imidazol-1-yl-5-trifluoromethyl-phenyl)-ureido]-phenoxy}-1H-benzoimidazol-2-yl)-carbamic acid methyl ester;

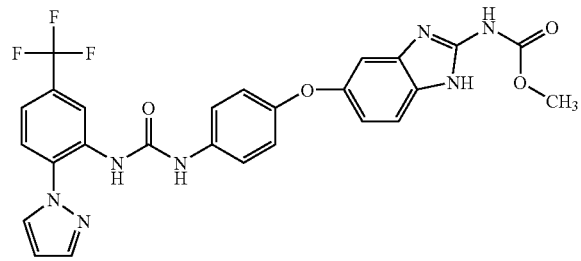

(5-{4-[3-(2-Pyrazol-1-yl-5-trifluoromethyl-phenyl)-ureido]-phenoxy}-1H-benzoimidazol-2-yl)-carbamic acid methyl ester;

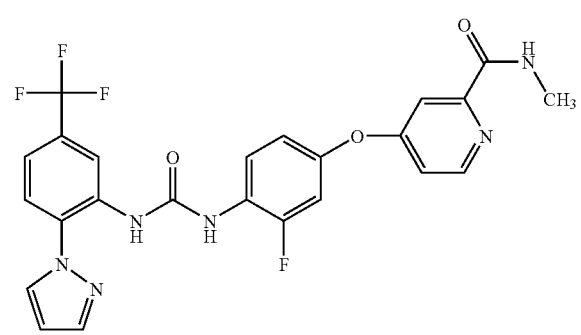

4-{3-Fluoro-4-[3-(2-pyrazol-1-yl-5-trifluoromethyl-phenyl)-ureido]-phenoxy}-pyridine-2-carboxylic acid methylamide;

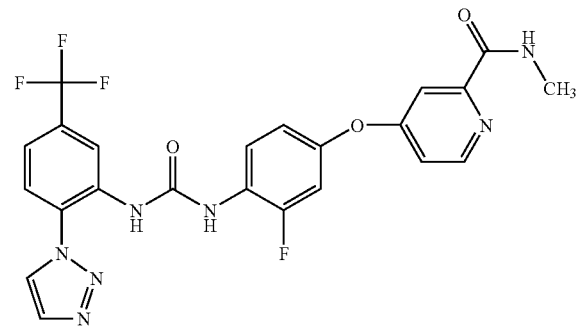

4-{3-Fluoro-4-[3-(2-[1,2,3]triazol-1-yl-5-trifluoromethyl-phenyl)-ureido]-phenoxy}-pyridine-2-carboxylic acid methylamide;

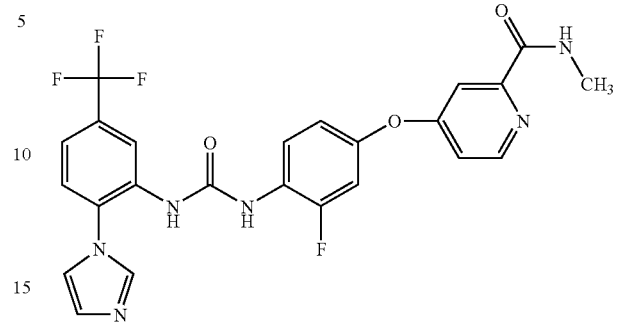

4-{3-Fluoro-4-[3-(2-imidazol-1-yl-5-trifluoromethyl-phenyl)-ureido]-phenoxy}-pyridine-2-carboxylic acid methylamide;

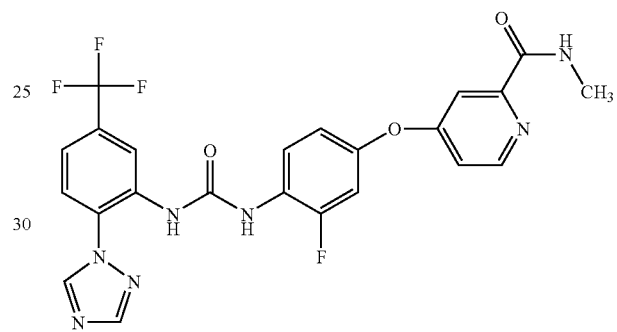

4-{3-Fluoro-4-[3-(2-[1,2,4]triazol-1-yl-5-trifluoromethyl-phenyl)-ureido]-phenoxy}-pyridine-2-carboxylic acid methylamide;

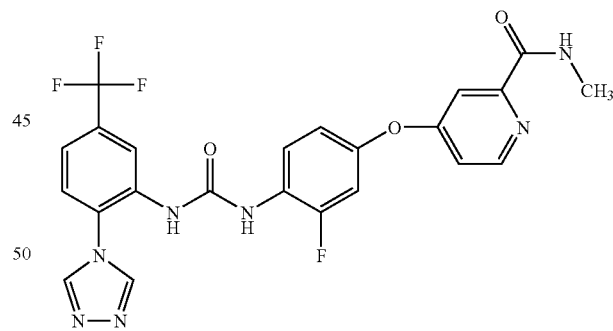

4-{3-Fluoro-4-[3-(2-[1,2,4]triazol-4-yl-5-trifluoromethyl-phenyl)-ureido]-phenoxy}-pyridine-2-carboxylic acid methylamide;

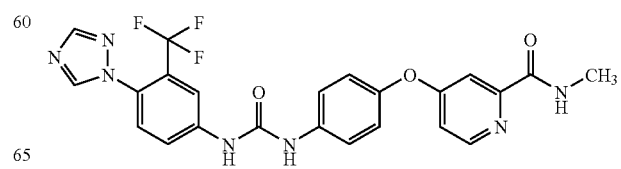

4-{4-[3-(4-[1,2,4]Triazol-1-yl-3-trifluoromethyl-phenyl)-ureido]-phenoxy}-pyridine-2-carboxylic acid methylamide;

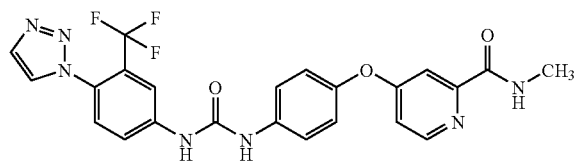

4-{4-[3-(4-[1,2,3]Triazol-1-yl-3-trifluoromethyl-phenyl)-ureido]-phenoxy}-pyridine-2-carboxylic acid methylamide;

and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Further especially preferred compounds according to the invention are selected from the compounds given below:

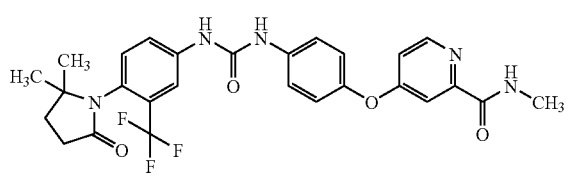

4-(4-{3-[4-(2,2-Dimethyl-5-oxo-pyrrolidin-1-yl)-3-trifluoromethyl-phenyl]-ureido}-phenoxy)-pyridine-2-carboxylic acid methylamide;

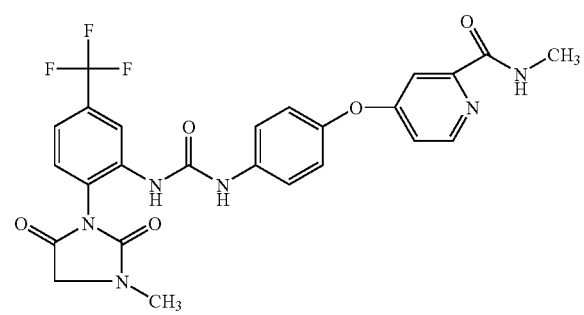

4-(4-{3-[2-(3-Methyl-2,5-dioxo-imidazolidin-1-yl)-5-trifluoromethyl-phenyl]-ureido}-phenoxy)-pyridine-2-carboxylic acid methylamide;

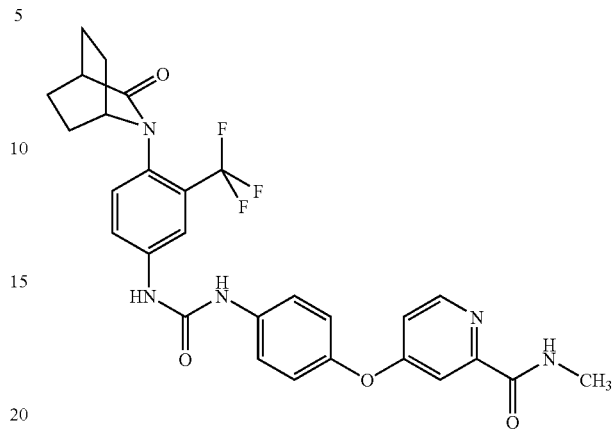

4-(4-{3-[4-(3-Oxo-2-aza-bicyclo[2.2.2]oct-2-yl)-3-trifluoromethyl-phenyl]-ureido}-phenoxy)-pyridine-2-carboxylic acid methylamide;

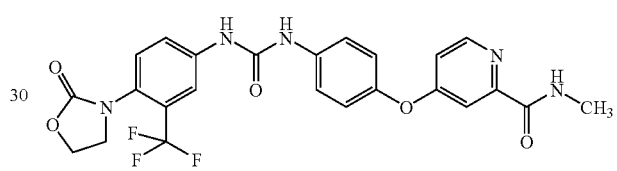

4-(4-{3-[4-(2-Oxo-oxazolidin-3-yl)-3-trifluoromethyl-phenyl]-ureido}-phenoxy)-pyridine-2-carboxylic acid methylamide;

and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Further preferred compounds according to the invention are selected from the compounds given below:

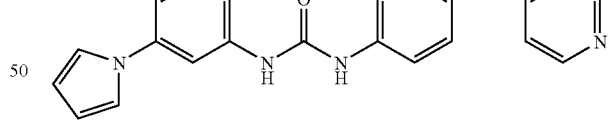

1-[4-(Pyridin-4-yloxy)-phenyl]-3-(3-pyrrol-1-yl-phenyl)-urea;

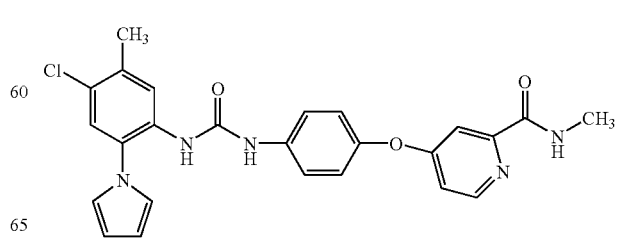

4-{4-[3-(4-Chloro-5-methyl-2-pyrrol-1-yl-phenyl)-ureido]-phenoxy}-pyridine-2-carboxylic acid methylamide;
and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

The nomenclature as used herein for defining compounds, especially the compounds according to the invention, is in general based on the rules of the IUPAC-organisation for chemical compounds and especially organic compounds.

Another aspect of the invention relates to a method for producing compounds of formula I, characterised in that
a) a compound of formula II,

wherein
$L^1$ and $L^2$ either independently from one another represent a leaving group, or together represent a leaving group, and Y is as defined above/below,
is reacted with
b) a compound of formula III

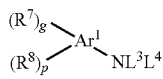

wherein
$L^3$ and $L^4$ are independently from one another H or a metal ion, and wherein $R^7$, $R^8$, g, p and $Ar^1$ are as defined above and below,
and
c) a compound of formula IV,

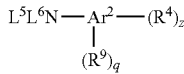

and more preferably a compound of formula IV',

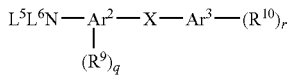

wherein
$L^5$ and $L^6$ are independently from one another H or a metal ion, and $R^9$, q, $Ar^2$, $R^4$, and z and more preferably $R^9$, q, $Ar^2$, X, $Ar^3$, $R^{10}$ and r are as defined above and below, and optionally
d) isolating and/or treating the compound of formula I obtained by said reaction with an acid, to obtain the salt thereof.

The compounds of the formula I and also the starting materials for their preparation can be prepared by methods known per se, i.e. as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ by not isolating them from the reaction mixture, but instead immediately converting them further into the compounds of the formula I. On the other hand, it is possible to carry out the reaction stepwise.

The compounds according to the invention can be manufactured or produced in an advantageous manner according to the methods of manufacture as described herein.

The reaction for the manufacture of compounds of formula I as described herein can be characterised as a carbonylation reaction of amines or the reaction of amines with carbon dioxide, carbon disulphide or derivatives or analogues thereof.

According to one aspect of the method according to the invention, in the compounds of formula II, $L^1$ and $L^2$ are preferably selected independently from one another from suitable leaving groups. Suitable leaving groups $L^1$ and $L^2$ for this type of reaction are known in the art, for example from the literature cited above. More preferably, $L^1$ and $L^2$ are independently selected from halogen, $OR^{25}$ and $O-SO_2-R^{25}$. The residue $R^{25}$ is preferably selected from substituted or unsubstituted alkyl groups and substituted or unsubstituted aryl groups, preferably substituted alkyl groups and substituted aryl groups. Preferred as alkyl groups in this respect are C1-C4-alkyl groups. Preferred as aryl group in this respect is phenyl. Suitable substituents for substituted alkyl groups are preferably selected from electronegative and/or electron withdrawing groups. Examples of electronegative and/or electron withdrawing groups for substituted alkyl groups include, but are not limited to halogen, especially Cl and/or F, cyano groups and nitro groups. Suitable substituents for substituted aryl groups are preferably selected from alkyl groups, preferably $C_1$-$C_4$ alkyl groups, and electronegative and/or electron withdrawing groups. Examples of electronegative and/or electron withdrawing groups for substituted aryl groups include, but are not limited to halogen, especially Cl and/or F, cyano groups and nitro groups. If $R^{25}$ is an unsubstituted alkyl group, it is preferably methyl. If $R^{25}$ his a substituted alkyl group, it is preferably $CF_3$ or $CCl_3$. If $R^{25}$ is an unsubstituted aryl group, it is preferably phenyl. If $R^{25}$ is a substituted aryl group, it is preferably selected from para-tolyl- (i.e. p-Me-$C_6H_4$) and para-Nitro-phenyl (i.e the p-$O_2$N—$C_6H_4$).

Even more preferably, the leaving groups $OR^{25}$ are selected from the para-Tosyl- (i.e. p-Me-$C_6H_4$—$SO_3$—) group, the para-Nitro-phenolate- (i.e the p-$O_2$N—$C_6H_4$—O—) group and the triflate- (i.e. the $F_3$C—$SO_3$—) group.

Preferably, compounds of formula II, wherein $L^1$ and $L^2$ are selected independently from one another from suitable leaving groups, are selected from compounds IIa, IIb and IIc,

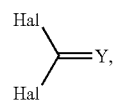

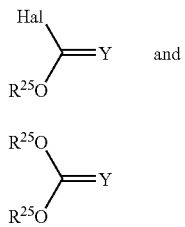

wherein Y, Hal and $OR^{25}$ are as described above/below.

According to another aspect of the method according to the invention, in the compounds of formula II, $L^1$ and $L^2$ together represent a leaving group. In this aspect, $L^1$ and $L^2$ together preferably represent Y as the leaving group, wherein the leaving group Y is as defined above/below and more preferably is O or S.

According to this aspect of the method according to the invention, the compound of formula II is a compound of formula II',

Y=C=Y  II' wherein each Y is independently selected from the meaning given above/below, and especially is independently selected from O and S.

According to this aspect of the method according to the invention, the compound of formula II is preferably selected from compounds of formula IId, formula IIe and formula IIf,

O=C=O,  IId

S=C=S and  IIe

O=C=S  IIf more preferably of compounds of formula IId and formula IIe. In this aspect, compounds of formula IIa are especially preferred.

In compounds of formula II, Y is preferably selected from O and S, and more preferably is O.

If compounds of formula II are desired wherein Y is other than O, it can be advantageous however to carry out the reaction according to the invention selecting a compound of formula II wherein Y is O, and to modify or convert the corresponding C=O group (i.e. the C=Y group, wherein Y is O) in the compound of formula I into a C=NR$^{21}$, C=C(R$^{22}$)—NO$_2$, C=C(R$^{22}$)—CN or C=C(CN)$_2$ group according to methods known in the art, for example from Houben-Weyl, Methods of Organic Chemistry.

In the method of manufacture according to the invention, the compound of formula II is even more preferably a compound of formula IIg,

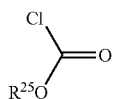

IIg wherein $R^{25}$ is as defined above/below, and especially a compound of formula IIh,

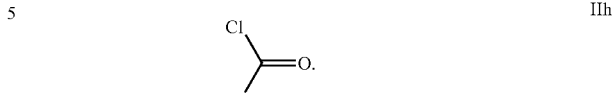

IIh

In the compounds of formula IV, $L^1$, $L^2$ and/or $L^3$ is preferably H or a moiety which activates the amino group it is bonded to, for example a metal ion. Suitable metal ions are preferably selected from the group consisting of alkaline metal ions, alkaline-earth metal ions and aluminium ions. Especially preferred metal ions are alkaline metal ions, of which Li, Na K are especially preferred. In case of multivalent metal ions, the metal ions and the compounds of formula IV form a complex containing one or more compounds of formula IV and one or more metal ions wherein the ratio between compounds of formula IV and metal ions is depending on the valency of the metal ion(s) according to the rules of stoichiometry and/or electroneutrality. Preferably, at least one of $L^1$, $L^2$ and $L^3$, more preferred at least two of $L^1$, $L^2$ and $L^3$ and even more preferred $L^1$, $L^2$ and $L^3$ are hydrogen.

In detail, the reaction of the compounds of formula II, formula III and formula IV is carried out in the presence or absence of a preferably inert solvent at temperatures between about −20° C. and about 200° C., preferably between −10° C. and 150° C. and especially between 0° C. or room temperature (25°) and 120°. In many cases, it is advantageous to combine one compound of formula III with one compound of formula IV at the lower end of the given temperature range, preferably between −20° C. and 75° C., more preferred between 0° C. and 60° C. and especially between 10° C. and 40° C., for example at about room temperature, and heat the mixture up to a temperature at the upper end of the given temperature range, preferably between 65° C. and 180° C., more preferred between 75° C. and 150° C. and especially between 80° C. and 120° C., for example at about 80° C., at about 90° C. or at about 100° C. Proceeding in that manner can be advantageous in the case that pound of formula II is the compounds of formula II'. If the compound of formula II is not a compound of formula II', the reaction can be regularly carried out without prolonged heating to higher temperatures. For example, it can preferably be carried out at a temperature between −10° C. and 60° C., more preferably between −5° C. and 40° C. and even more preferably at about 0° C. or at about room temperature. This given temperature range is especially advantageous, if the compound of formula II is selected from compounds of formula IIa, IIb, IIc and especially is a compound of formula IIg or IIh.

The method for manufacture according to the invention is preferably carried out in the presence of an acid binding means, for example one or more bases. This is especially advantageous, if the compound of formula II is selected from compounds of formula IIa-IIc an even preferred if the compound is selected from the compounds of formula IIg or formula IIh.

Suitable acid binding means are known in the art. Preferred as acid binding means are inorganic bases and especially organic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Examples for organic bases are triethyl amine, diisopropyl ethyl amine (DIPEA), diaza bicyclo undecen (DBU), dimethyl aniline, pyridine or chinoline. If an organic base is used, it is advantageous in general to use a base with a boiling point that is higher than the highest reaction temperature employed during the reaction. Especially preferred as organic bases are pyridine and DIPEA. In many cases it is advantageous to employ two different organic bases and especially to use pyridine and DIPEA.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally IIe in the range 10 min and 36 hrs, preferably 30 min and 24 hrs and especially between 45 min and 18 hrs, for example about 1 h, about 2 hrs, about 4 hrs, about 6 or about 18 hrs.

Preferably, the reaction of the compounds of the formula III with the compounds of the formula IV is carried out in the presence of a suitable solvent, that is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

Polar solvents are in general preferred. Examples for suitable polar solvents are chlorinated hydrocarbons, alcohols, glycol ethers, nitrites, amides and sulfoxides or mixtures thereof. More preferred are chlorinated hydrocarbons, especially dichloromethane, and amides, especially DMF.

In general, the compounds of formula III and/or formula IV are new. In any case, they can be prepared according to methods known in the art.

The compounds of formula III can be obtained according to methods known in the art. In an advantageous manner, they can be readily obtained by one or more of the reaction routes given below:

Compounds of formula III can be readily obtained from synthesis sequence as given below:

The reaction of derivatives of formula (A)

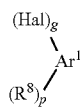

(A)

wherein Hal is Cl, Br or F and especially is F, and wherein g, $R^8$, p and $Ar^1$ are as defined above/below, with p compounds of formula (B)

$L^7$-$R^7$ (B)

wherein $R^7$ is as defined above/below and $L^7$ is preferably selected from H or a metal ion, if $L^7$ is bound to an oxygen atom of $R^7$ or to an nitrogen atom of $R^7$, or selected from carbon atom activating groups, if $L^7$ is bound to a carbon atom of $R^7$, leads to compounds of formula (C).

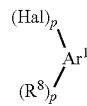

(C)

Suitable carbon atom activating groups for this type of reaction are known in the art. Suitable metal ions are preferably selected from the group consisting of alkaline metal ions, alkaline-earth metal ions and aluminium ions. Preferred metal ions are alkaline metal ions, of which Li, Na and/or K are especially preferred. Even more preferred as $L^7$ is H.

Accordingly, preferred compounds of formula (B) for the method for manufacture according to the invention are compounds that comprise a hydroxy-group, a primary amino group or a secondary amino group. Thus, especially preferred are compounds of formula (B), that comprise an HO—, a $H_2N$-group, a $HNR^{11}$-group or a $HNR^{12}$-group, and especially compounds that comprise a terminal HO—, a $H_2N$-group, a $HNR^{11}$-group or a $HNR^{12}$-group, wherein $R^{11}$ and $R^{12}$ are as defined above/below.

This type of reaction is generally known as aromatic substitution. Suitable reaction conditions for the reaction of the compounds of formula (A) with the compounds of formula (B) are known in the art.

The compound of formula (C) then can be transferred into the compound of formula III by methods known in the art.

Advantageously, the compound of formula (C) then can be transferred into a compound of formula (D),

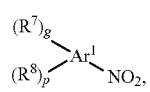

(D)

by a nitration reaction. Suitable methods and reaction conditions for nitration reactions are known in the art. Advantageously, the compounds of formula (D) can be obtained by reacting a compound of formula (C) with nitrating acid or a combination of concentrated sulfuric acid and potassium nitrate. If a combination of concentrated sulfuric acid and potassium nitrate is used, it can be advantageous to perform the reaction at a relatively low temperature, for example between −20° C. and +50° C., preferably between −10° C. and room temperature, more preferred between −5° C. and 0° C.

The compound of formula (D) then can be transferred into a compound of formula III, wherein $L^3$ and $L^4$ are hydrogen, preferably by a reduction reaction or hydrogenating reaction, preferably a hydrogenating reaction. Methods and reaction conditions for hydrogenating a $NO_2$-moiety into a $NH_2$-moiety are known in the art. In general, it is advantageous to carry out the hydrogenation reaction in a hydrogen atmosphere in the presence of a suitable catalyst, for example Pd/C or Raney-nickel, preferably Raney-nickel. In general, such hydrogenation reactions are carried out in a suitable solvent. Suitable solvents for hydrogenation reactions are known in the art. Suitable solvents, for example, are alcohols, especially methanol and ethanol and ethers, especially THF, and mixtures thereof. Preferred as solvent is a mixture of THF/ methanol, preferably in about equal measures. In general, the hydrogenation reactions are carried out at about normal pressure or slightly elevated pressure, for example between normal pressure and 3 bar pressure (about 300 kPa). The hydrogenation reaction is usually carried out in the temperature range between −20° and 150°, preferably 0° and 50°. The obtained compound of formula III wherein $L^3$ and $L^4$ are hydrogen can optionally be isolated and/or purified and then optionally transferred into a compound of formula III wherein $L^3$ and $L^4$ are other than hydrogen, for example according to methods and reaction conditions as described herein.

Some of the starting materials of the formula V and/or the formula VI are known and preferably commercially available. If they are not known, they can be prepared by methods known per se.

Generally, the compounds of formula IV and/or IV' can be obtained according to methods known in the art. For example, they can be prepared according to methods described in Jerchel et al., Chem. Ber. 1956, 2921-2928, WO 02/044156, WO 03/099771, WO 00/42012, Curtin et al., Bioorg. Med. Chem. Lett., in press, or in an analogous manner thereof.

If the compound of formula IV is a compound according to formula IVa,

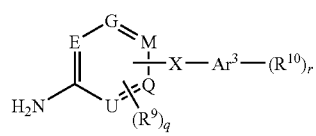

IVa it can be readily obtained in an advantageous manner by reacting a compound of formula VIIa,

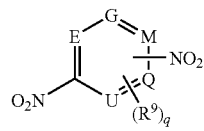

VIIa wherein $R^9$ and q are as defined above/below,
with a compound of formula VIII,

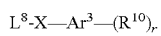

VIII wherein $L^8$ is H or a metal ion, preferably a metal ion selected from the group consisting of alkaline metal ions, alkaline-earth metal ions and aluminum ions, especially preferred alkaline metal ions, of which Li, Na and K are especially preferred, and even more preferred is H;
optionally isolating the reaction product,
and transferring the obtained reaction product of formula IX

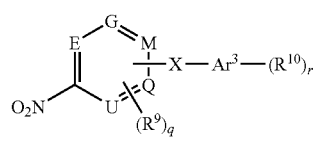

IX into a compound of formula IVa, preferably by hydrogenating the $NO_2$-moiety of the compound of formula IX into a $NH_2$-moiety. Methods and reaction conditions for hydrogenating said $NO_2$-moiety into a $NH_2$-moiety are known in the art. In general, it is advantageous to carry out the hydrogenation reaction in a hydrogen atmosphere in the presence of a suitable catalyst, preferably a Palladium catalyst, for example Pd/C. In general, such hydrogenation reactions are carried out in a suitable solvent. Suitable solvents for hydrogenation reactions are known in the art. Suitable solvents, for example, are alcohols, especially methanol and ethanol and ethers, especially THF, and mixtures thereof. In general, the hydrogenation reactions are carried out at about normal pressure or slightly elevated pressure, for example between normal pressure and 3 bar pressure (about 300 kPa). The hydrogenation reaction is usually carried out in the temperature range between −20° and 150°, preferably 0° and 50°.

$Ar^3$ is preferably pyridinyl. Accordingly, the compound of formula VIII is preferably selected from the group consisting of formulae VIIIa and VIIIb,

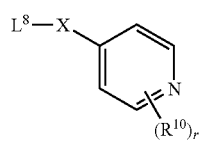

VIIIa

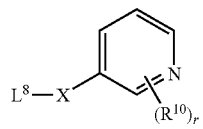

VIIIb wherein $L^8$, X, $R^{10}$ and r are defined above, and especially preferred from the group consisting of formulae VIIIc and VIIId,

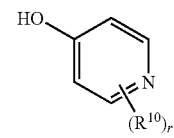

VIIIc

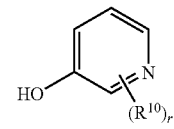

VIIId wherein $R^{10}$ and r are as defined above, or the alkaline metal salts and especially the sodium or potassium salts thereof.

Accordingly, in formulae IVa, VIII, VIIIa, VIIIb and IX, the bridging group X is preferably O, S, $OCH_2$ and $OCH_2CH_2$ and especially is O.

In the formulae VIII, VIIIa and VIIIb, $L^8$ is preferably H or selected from the group consisting of Na, K and Cs and especially preferred is H.

In general, this reaction is advantageous to produce compounds of formula IVaa,

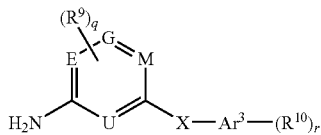

IVaa wherein $R^9$, q, X, $Ar^3$, $R^{10}$ and r are as defined above/below.

To obtain compounds of formula IVaa, it is reasonable to employ a compound of formula VII that is selected from the compounds of formula VIIIa,

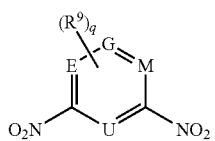

VIIa and proceed the reaction as described above/below.

Accordingly, by starting from a compound of formula VIIIa and a compound of formula VIIIa, the reaction preferably leads to compounds of formula IVaaa,

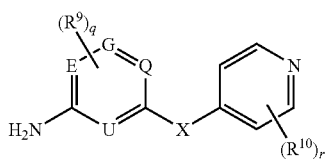

IVaaa wherein $R^9$, q, X, $R^{10}$ and r are as defined above/below.

Accordingly, by starting from a compound of formula VIIIa and a compound of formula VIIIb, the reaction preferably leads to compounds of formula IVaab,

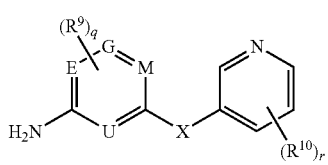

IVaab wherein $R^9$, q, X, $R^{10}$ and r are as defined above/below.

Accordingly, by starting from a compound of formula VIIIa and a compound of formula VIIIc, the reaction preferably leads to compounds of formula IVaac,

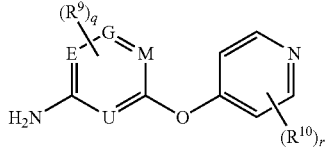

IVaac wherein $R^9$, q, $R^{10}$ and r are as defined above/below.

Accordingly, by starting from a compound of formula VIIIa and a compound of formula VIIId, the reaction preferably leads to compounds of formula

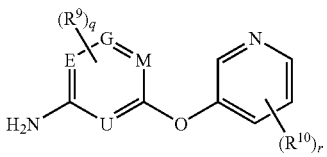

IVaad wherein $R^9$, q, $R^{10}$ and r are as defined above/below.

Some of the starting materials of the formula VII and/or the formula VIII are known and preferably commercially available. If they are not known, they can be prepared by methods known per se.

The reaction between the compound of formula VII and VIII is preferably carried out in the temperature range between 0° and 250°, more preferred room temperature and 200°, for example at about 120°, at about 150° or at about 180°. Reaction times depend on the respective reactants and the respective reaction temperature, but generally lie in the range between 30 min and 36 hrs, preferably 3 hrs and 24 hrs, more preferably 8 hrs and 20 hrs for example about 10 hrs, about 16 hrs or about 18 hrs.

The reaction can be carried out in the absence of solvent or preferably in the presence of an solvent, preferable a solvent that is inert under the respective reaction conditions. Suitable inert solvents for carrying out the reaction are known in the art. Examples for suitable solvents are high boiling aliphatic hydrocarbons, high boiling aromatic carbons, for example toluene, xylenes, high boiling chlorinated hydrocarbons, such as trichloroethylene, tetrachloroethanes, pentachloroethanes and hexachloroethanes; high boiling ethers, such as ethylene glycol and propylene glycols; glycol ethers, such as ethylene glycol monomethyl or monoethyl ether or ethylene glycol dimethyl ether (diglyme); amides, such as acetamide, dimethylacetamide, dimethylformamide (DMF) or N-methyl pyrrolidinone (NMP); sulfoxides, such as dimethyl sulfoxide (DMSO); or mixtures of the said solvents. Preferred are amides, especially dimethylformamide (DMF).

Preferably, the reaction is carried out in the presence of a base. Suitable bases are known in the art. Preferred bases are organic bases and especially inorganic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Preferred inorganic bases are $K_2CO_3$, $Na_2CO_3$, $MgCO_3$, $CaCO_3$, NaOH and KOH, especially preferred is $K_2CO_3$. Examples for organic bases are triethyl amine, diisopropyl ethyl amine (DIPEA), dimethyl aniline, pyridine or chinoline. If an organic base is used, it is advantageous in general to use a base with a boiling point that is higher than the highest reaction temperature employed during the reaction.

Alternatively, if the compound of formula IV is a compound according to formula IVb,

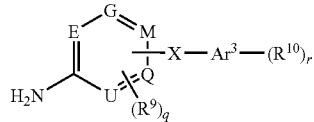

IVb it can be readily obtained in an advantageous manner by reacting a compound of formula VIIIb,

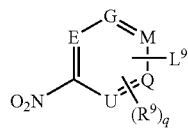

VIIb wherein $R^9$ and q are as defined above/below and wherein $L^9$ is selected independently from the meanings given for $L^1$, and preferably from Hal and especially is Cl, with a compound of formula VIIIb,

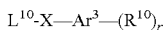

VIIIb wherein $L^{10}$ is H or a metal ion, preferably a metal ion, more preferred a metal ion selected from the group consisting of alkaline metal ions, alkaline-earth metal ions and aluminium ions, especially preferred alkaline metal ions, of which Li, Na and K are especially preferred; and $Ar^3$, $R^{10}$, r and X are as defined above/below;
optionally isolating the reaction product,
and transferring the obtained reaction product of formula IXb

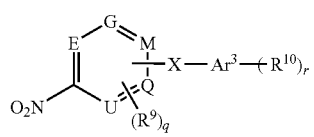

IXb into a compound of formula IVa, preferably by hydrogenating the $NO_2$-moiety of the compound of formula IX into a $NH_2$-moiety. Methods and reaction conditions for hydrogenating said $NO_2$-moiety into a $NH_2$-moiety are known in the art. In general, it is advantageous to carry out the hydrogenation reaction in a hydrogen atmosphere in the presence of a suitable catalyst, preferably a Palladium catalyst, for example Pd/C. In general, such hydrogenation reactions are carried out in a suitable solvent. Suitable solvents for hydrogenation reactions are known in the art. Suitable solvents, for example, are alcohols, especially methanol and ethanol, ethers, especially THF, and mixtures thereof. In general, the hydrogenation reactions are carried out at about normal pressure or slightly elevated pressure, for example between normal pressure or slightly elevated pressure, for example between normal pressure and 3 bar pressure (about 300 kPa). The hydrogenation reaction is usually carried out in the temperature range between −20° and 150°, preferably 0° and 50°.

$Ar^3$ is preferably pyridinyl. Accordingly, the compound of formula VIIIb is preferably selected from the group consisting of formulae VIIIe and VIIIf,

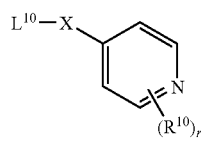

VIIIe

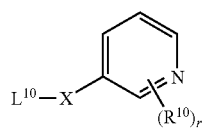

VIIIf wherein $L^{10}$, X, $R^{10}$ and r are as defined above, and especially preferred from the group consisting of formulae VIIIg and VIIIh,

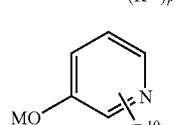

VIIIg

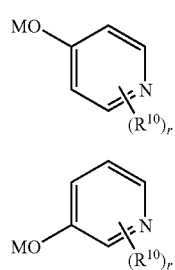

VIIIh wherein $R^{10}$ and r are as defined above, and wherein M is an alkaline metal ion and especially sodium or potassium, or the corresponding alcohols thereof.

Accordingly, in formulae IVb, VIIIb, VIIIe, VIIIf and IXb, the bridging group X is preferably O, S, $OCH_2$ and $OCH_2CH_2$ and especially is O.

In general, this alternative reaction is advantageous to produce compounds of formula IVbb,

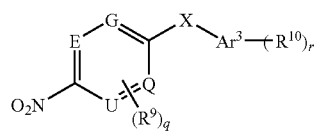

IVbb wherein $R^9$, q, X, $Ar^3$, $R^{10}$ and r are as defined above/below.

To obtain compounds of formula IVbb, it is reasonable to employ a compound of formula VIIb that is selected from the compounds of formula VIIbb,

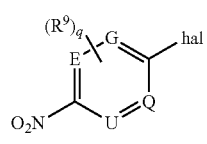

VIIbb wherein hal is as defined above/below and especially is Cl, and proceed the alternative reaction as described above/below.

Accordingly, by starting from a compound a formula VIIbb and a compound of formula VIIe, the reaction preferably leads to compounds of formula IVbbe,

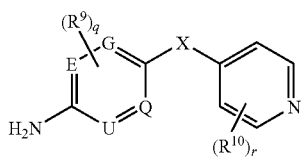

IVbbe wherein $R^9$, q, X, $R^{10}$ and r are as defined above/below.

Accordingly, by starting from a compound of formula VIIbb and a compound of formula VIIIf, the reaction preferably leads to compounds of formula IVbbf,

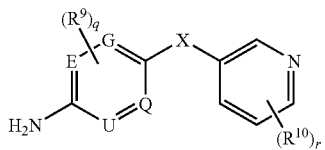

IVbbf wherein $R^9$, q, X, $R^{10}$ and r are as defined above/below.

Accordingly, by starting from a compound of formula VIIbb and a compound of formula VIIIg, the reaction preferably leads to compounds of formula IVbbg,

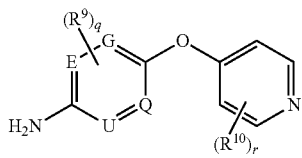

IVbbg wherein $R^9$, q, $R^{10}$ and r are as defined above/below.

Accordingly, by starting from a compound of formula VIIb and a compound of formula VIIIh, the reaction preferably leads to compounds of formula IVbbh,

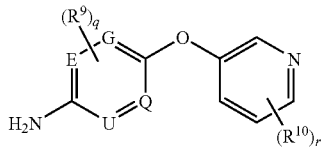

IVbbh wherein $R^9$, q, $R^{10}$ and r are as defined above/below.

Some of the starting materials of the formula VIIb and/or the formula VIIIb are known and preferably commercially available. If they are not known, they can be prepared by methods known per se.

The reaction between the compound of formula VIIb and VIIIb is preferably carried out in the temperature range between 0° and 250°, more preferred 50° and 220°, for example at about 90°, at about 120°, at about 160°, at about 180° or at about 200°. Reaction times depend on the respective reactants and the respective reaction temperature, but generally lie in the range between 10 min and 24 hrs, preferably 30 min and 12 hrs, more preferably 1 h and 6 hrs for example about 1.5 hrs, about 3 hrs, about 4 hrs or about 5 hrs.

The reaction can be carried out in the absence or the presence of a solvent, preferable a solvent that is inert under the respective reaction conditions. Suitable inert solvents for carrying out the reaction are known in the art. Examples for suitable solvents are high boiling aliphatic hydrocarbons, aromatic carbons, for example toluene and xylenes, high boiling chlorinated hydrocarbons, such as dichloromethane, trichloromethane trichloroethylene, tetrachloroethanes, pentachloroethanes and hexachloroethanes; ethers, such as diethylether, tert.-butyl methyl ether, ethylene glycol and propylene glycols; glycol ethers, such as ethylene glycol monomethyl or monoethyl ether or ethylene glycol dimethyl ether (diglyme); nitriles, such as acetonitrile, amides such as acetamide, dimethyacetamide, dimethylformamide (DMF) or N-methylpyrrolidinone (NMP); sulfoxides, such as dimethyl sulfoxide (DMSO); or mixtures of the said solvents.

Preferably, the reaction is carried out in the presence of a catalyst. Suitable catalysts are known in the art. Preferred are catalytic active metals and especially copper.

Preferably, the reaction is carried out by heating up a reaction mixture comprising one compound of formula VIIb and one compound of formula VIIIb to a suitable reaction temperature, which preferably lies at the upper end of the given temperature ranges and more preferred is in the range between 150° and 200°, for example at about 180°, preferably in the presence of the suitable catalyst and especially in the presence of copper. Reaction times at this temperature are preferably as given above and especially in the range between 1 h and 5 hrs, for example about 3 hrs. Preferably, the reaction mixture is then allowed to cool down to a temperature in the lower range of the given temperature, more preferred to a temperature in the range between 50° and 150°, for example to about 90°. Preferably, a suitable solvent, preferably tert.-butyl methyl ether, is then added and the reaction mixture is preferably kept at about the same temperature for some more time, preferably for 30 min to 2 hrs and more preferred for about one hour.

Independently of the chosen reaction route, it is in many cases possible or even feasible to introduce residues $R^7$, $R^8$, $R^9$ and/or $R^{10}$ into one or more of the compounds described above, or, if the compound already comprises one or more residues $R^7$, $R^8$, $R^9$ and/or $R^{10}$, to introduce additional residues $R^7$, $R^8$, $R^9$ and/or $R^{10}$ into said compound. The introduction of additional residues can be readily performed by methods known in the art and especially by aromatic substitution, for example nucleophilic aromatic substitution or electrophilic aromatic substitution. For example, in compounds comprising $Ar^1$, wherein $Ar^1$ comprises one or more halogen and preferably fluorine substituents, one or more of the halogen/fluorine substituents can be easily substituted by hydroxy, thio and/or amino substituted hydrocarbons and or compounds H—$R^7$ and the metal salts thereof, On the other hand, it is in many cases possible or even feasible to modify or derivatize one or more of the residues $R^7$, $R^8$, $R^9$ and/or $R^{10}$ into residues $R^7$, $R^8$, $R^9$ and/or $R^{10}$ other than the ones originally present. For example, $CH_3$-groups can be oxidized into aldehyde groups or carboxylic acid groups, thio atom containing groups, for example S-alkyl or S-aryl groups, can be oxidized into $SO_2$-alkyl or $SO_2$-aryl groups, respectively, carboxylic acid groups can be derivatized to carboxylic acid ester groups or carboxylic acid amide groups and carboxylic acid ester groups or carboxylic acid amide groups can be hydrolysed into the corresponding carboxylic acid groups. Methods for performing such modifications or derivatizations are known in the art, for example from Houben-Weyl, Methods of Organic Chemistry.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

A base of the formula I can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid. Salts with physiologically unacceptable acids, for example picrates, can be used to isolate and/or purify the compounds of the formula I. On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

On the other hand, if desired, the free bases of the formula I can be liberated from their salts using bases (for example sodium hydroxide, potassium hydroxide, sodium carbonate or potassium carbonate).

The invention relates to compounds of the formula I and physiologically acceptable salts and solvates thereof as medicaments.

The invention also relates to the compounds for the formula I and physiologically acceptable salts and solvates thereof as kinase inhibitors.

The invention furthermore relates to the use of the compounds of the formula I and/or physiologically acceptable salts and/or solvates thereof for the preparation of pharmaceutical compositions and/or pharmaceutical preparations, in particular by non-chemical methods. In this cases, one or more compounds according to the invention can be converted into a suitable dosage form together with at least one solid, liquid and/or semi-liquid excipient or adjuvant and, if desired, in combination with one or more further active ingredients.

The invention further relates to the use of one or more of the compounds according to the invention, selected from the group consisting of compounds of the formula I as free bases, solvates of compounds of the formula I, salts of compounds of formula I, for the production of pharmaceutical compositions and/or pharmaceutical preparations, in particular by a non-chemical route. In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingredients. In this respect, active ingredients are preferably at least one compound according to this invention and one or more additional compounds other than the compounds according to the invention, which show valuable pharmaceutical properties, preferably those pharmaceutical active agents other than the compounds according to the invention which are disclosed herein.

The process for preparing pharmaceutical compositions and/or pharmaceutical preparations preferably comprises one or more processing steps, selected from the group consisting of combining, milling, mixing, granulating, dissolving, dispersing, homogenizing and compressing. The one or more processing steps are preferably performed on one or more of the ingredients which are to form the pharmaceutical composition and/or pharmaceutical preparation preferably according to the invention. Even more preferred, said processing steps are performed on two or more of the ingredients which are to form the pharmaceutical composition and/or pharmaceutical preparation, said ingredients comprising one or more compounds according to the invention and, additionally, one or more compounds, preferably selected from the group consisting of active ingredients other than the compounds according to the invention, excipients, auxiliaries, adjuvants and carriers. Mechanical means for performing said processing steps are known in the art, for example from Ullmann's Encyclopedia of Industrial Chemistry, 5th Edition.

Preferably, one or more compounds according to the invention are converted into a suitable dosage form together with at least one compound selected from the group consisting of excipients, auxiliaries, adjuvants and carriers, especially solid, liquid and/or semi-liquid excipients, auxiliaries, adjuvants and carriers, and, if desired, in combination with one or more further active ingredients.

Suitable dosage forms include, but are not limited to tablets, capsules, semi-solids, suppositories, aerosols, which can be produced according to methods known in the art, for example as described below:

tablets mixing of active ingredient/s and auxiliaries, compression of said mixture into tablets (direct compression), optionally granulation of part of mixture before compression capsules mixing of active ingredient/s and auxiliaries to obtain a flowable powder, optionally granulating powder, filling powders/granulate into opened capsules, capping of capsules semi-solids (ointments, gels, creams) dissolving/dispersing active ingredient/s in an aqueous or fatty carrier; subsequent mixing of aqueous/fatty phase with complementary fatty resp. aqueous phase, homogenisation (creams only)

suppositories (rectal and vaginal) dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms aerosols: dispersing/dissolving active agent/s in a propellant, bottling said mixture into an atomizer The invention thus relates to pharmaceutical compositions and/or pharmaceutical preparations comprising at least one compound of the formula I and/or one of its physiologically acceptable salts and/or solvates.

Preferably, the pharmaceutical compositions and/or pharmaceutical preparations according to the invention contain a therapeutic effective amount of one or more compounds according to the invention. Said therapeutic effective amount of one or more of the compounds according to the invention is known to the skilled artisan or can be easily determined by standard methods known in the art. For example, the compounds according to the invention can be administered to a patient in an analogous manner to other compounds that are effective as raf-kinase inhibitors, especially in an analogous manner to the compounds described in WO 00/42012 (Bayer). Usually, suitable doses that are therapeutically effective lie in the range between 0.0005 mg and 1000 mg, preferably between 0.005 mg and 500 mg and especially between 0.5 and 100 mg per dose unit. The daily dose comprises preferably more than 0.001 mg, more preferred more than 0.01 milligram, even more preferred more than 0.1 mg and especially more than 1.0 mg, for example more than 2.0 mg, more than 5 mg, more than 10 mg, more than 20 mg, more than 50 mg or more than 100 mg, and preferably less than 1500 mg, more preferred less than 750 mg, even more preferred less than 500 mg, for example less than 400 mg, less than 250 mg, less than 150 mg, less than 100 mg, less than 50 mg or less than 10 mg.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician which advises or attends the therapeutic treatment.

However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular illness to which the therapy applies. Parenteral administration is preferred. Oral administration is especially preferred.

These compositions and/or preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Examples for suitable dosage forms, which are especially suitable for oral administration are, in particular, tablets, pills, coated tablets, capsules, powders, granules, syrups, juices or drops. Further examples for suitable dosage forms, which are especially suitable for rectal administration are suppositories, further examples for suitable dosage forms, which are especially suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The compositions and/or preparations indicated may be sterilized and/or comprise assistants, such as lubricants, preservatives, stabilizers and/or wetting agents, emulsifiers, salts for modifying the osmotic pressure, buffer substances, dyes and flavors and/or one or more further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

The compounds of the formula I and their physiologically acceptable salts and solvates can be employed for combating one or more diseases, for example allergic diseases, psoriasis and other skin diseases, especially melanoma, autoimmune diseases, such as, for example, rheumatoid arthritis, multiple sclerosis, Crohn's disease, diabetes mellitus or ulcerative colitis.

In General, the substances according to the invention are preferably administered in doses corresponding to the compound rolipram of between 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular illness to which the therapy applies. Oral administration is preferred.

The compounds of the formula I according to claim 1 and/or their physiologically acceptable salts are also used in pathological processes which are maintained or propagated by angiogenesis, in particular in tumors, restenoses, diabetic retinopathy, macular degenerative disease or rheumatoid arthritis.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with pharmaceutically active agents other than the compounds according to the invention, particularly other anti-metastatic, antitumor or anti-angiogenic agents. Angiostatic compounds of interest include angiostatin, enclostatin, carboxy terminal peptides of collagen alpha (XV), etc. Cytotoxic and cytostatic agents of interest include adriamycin, aleran, Ara-C, BICNU, busulfan, CNNU, cisplatinum, cytoxan, daunorubicin, DTIC, 5-FU, hydrea, ifosfamicle, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

The compounds of the invention preferably show an antiproliferative effect in an in vivo xenograft tumor model. The subject compounds are administered to a subject having a hyperproliferative disorders, e.g., to inhibit tumor growth, to decrease inflammation associated with a lymphoproliferative disorder, to inhibit graft rejection, or neurological damage due to tissue repair, etc. The present compounds are useful for prophylactic or therapeutic purposes. As used herein, the term "treating" is preferably also used to refer to both prevention of disease, and treatment of pre-existing conditions. The prevention of proliferation is accomplished by administration of the subject compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g., primate sp., particularly human; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one hour and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body.

The compounds according to the invention are preferably administered to human or nonhuman animals, more preferred to mammalian animals and especially to humans.

The compounds preferably also find use in the specific inhibition of a signaling pathway mediated by protein kinases. Protein kinases are involved in signaling pathways for such important cellular activities as responses to extracellular signals and cell cycle checkpoints. Inhibition of specific protein kinases provided a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in the signaling mediated by protein kinases. Such conditions include those associated with defects in cell cycle regulation or in response to extracellular signals, e.g., immunological disorders, autoimmune and immunodeficiency diseases; hyperproliferative disorders, which may include psoriasis, arthritis, inflammation, endometriosis, scarring, cancer, etc. The compounds of the present invention are active in inhibiting purified kinase proteins, preferably kinases as discussed herein, and especially kinases selected from raf-kinases, Tie-kinases, PDGFR-kinases and VEGFR-kinases, e.g., there is a decrease in the phosphorylation of a specific substrate in the presence of the compound. The compounds of the invention may also be useful as reagents for studying signal transduction or any of the clinical disorders listed throughout this application.

There are many disorders associated with a dysregulation of cellular proliferation. The conditions of interest include, but are not limited to, the following conditions. The subject compounds are useful in the treatment of a variety of conditions where there is proliferation and/or migration of smooth muscle cells, and/or inflammatory cells into the intimal layer of a vessel, resulting in restricted blood flow through that vessel, e.g., neointimal occlusive lesions. Occlusive vascular conditions of interest include atherosclerosis, graft coronary vascular disease after transplantation, vein graft stenosis, peri-anastomatic prothetic graft stenosis, restenosis after angioplasty or stent placement, and the like.

Diseases where there is hyperproliferation and tissue remodelling or repair or reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to product a tumor neovasculature.

Tumors of interest for treatment include carcinomas, e.g., colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies; e.g. neuroplastoma, gliomas, etc.; hematological malignancies, e.g., childhood acute leukaemia, non-Hodgkin's lymphomas, chronic lymphocytic leukaemia, malignant cutaneous T-cells, mycosis fungoides, non-MF cutaneous T-cell-lymphoma, lymphomatoid papulosis, T-cell rich cutaneous lymphoid hyperplasia, bullous pemphigoid, discoid lupus erythematosus, lichen planus, etc.; and the like.

Tumors of neural tissue are of particular interest, e.g., gliomas, neuromas, etc. Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltration (or invasive) ductal carcinoma (IDC) has metastasized through the wall of the duct and invaded the fatty tissue of the breast. Infiltrating (or invasive) lobular carcinoma (ILC) is similar to IDC, in that it has the potential to metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamos cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue, remodeling and repair. For example, the chronic skin inflammation of psoriasis is associated with hyperplastic epidermal keratinocyctes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemia's and lymphomas. Symptoms of allergies to environmental and food agents, as well as inflammatory bowel disease, may also be alleviated by the compounds of the invention.

Surprisingly, it has been found that bisarylurea derivatives according to the invention are able to interact with signaling pathways, especially the signaling pathways described herein and preferably the Tie-2, VEGFR-2 and/or raf-kinase signaling pathway. Bisarylurea derivatives according to the invention preferably show advantageous biological activity which can easily be demonstrated according to methods known in the art, for example by enzyme based assays. Suitable assays are known in the art, for example from the literature cited herein and the references cited in the literature, or can be developed and/or performed in an analogous manner thereof. In such enzyme based assays, bisarylurea derivatives according to the invention show an effect, preferably a modulating and especially an inhibiting effect which is usually documented by $IC_{50}$ values in a suitable range, preferably in the micromolar range and more preferred in the nanomolar range.

In general, compounds according to the invention are to be regarded as suitable kinase-modulators and especially suitable kinase-inhibitors according to the invention if they show an effect or an activity to one or more kinases, preferably to one or more raf-kinases that preferably lies, determined as $IC_{50}$-value, in the range of 100 µmol or below, preferably 10 µmol or below, more preferably in the range of 3 µmol or below, even more preferably in the range of 1 µmol or below and most preferably in the nanomolar range. Especially preferred for use according to the invention are kinase-inhibitors as defined above/below, that show an activity, determined as $IC_{50}$-value, to one or more kinases, preferably kinases as discussed herein, more preferably one or more kinases including or consisting of Tie-2, VEGFR-2 and/or raf-kinases, in the range of 0.5 µmol or below and especially in the range of 0.1 µmol or below. In many cases an $IC_{50}$-value at the lower end of the given ranges is advantageous and in some cases it is highly desirable that the $IC_{50}$-value is as small as possible or the he $IC_{50}$-values are as small as possible, but in general $IC_{50}$-values that lie between the above given upper limits and a lower limit in the range of 0.0001 µmol, 0.001 µmol, 0.01 µmol or even above 0.1 µmol are sufficient to indicate the desired pharmaceutical activity. However, the activities measured can vary depending on the respective testing system or assay chosen.

Alternatively, the advantageous biological activity of the compounds according to the invention can easily be demonstrated in in vitro assays, such as in vitro proliferation assays or in vitro growth assays. Suitable in vitro assays are known in the art, for example from the literature cited herein and the references cited in the literature or can be performed as described below, or can be developed and/or performed in an analogous manner thereof.

As an example for an in vitro growth assay, human tumor cell lines, for example HCT116, DLD-1 or MiaPaCa, containing mutated K-ras genes can be used in standard proliferation assays, for example for anchorage dependent growth on plastic or anchorage independent growth in soft agar. Human tumor cell lines are commercially available, for example from ATCC (Rockville Md.), and can be cultured according to methods known in the art, for example in RPMI with 10% heat inactivated fetal bovine serum and 200 mM glutamine. Cell culture media, fetal bovine serum and additives are commercially available, for example from Invitrogen/Gibco/BRL (Karlsruhe, Germany) and/or QRH Biosciences (Lenexa, Kans.). In a standard proliferation assay for anchorage dependent growth, $3 \times 10^3$ cells can be seeded into 96-well tissue culture plates and allowed to attach, for example overnight at 37° C. in a 5% $CO_2$ incubator. Compounds can be titrated in media in dilution series and added to 96 well cell cultures. Cells are allowed to grow, for example for 1 to 5 days, typically with a feeding of fresh compound containing media at about half of the time of the growing period, for example on day 3, if the cells are allowed to grow 5 days. Proliferation can be monitored by methods known in the art, such as measuring metabolic activity, for example with standard XTT calorimetric assay (Boehringer Mannheim) measured by standard ELISA plate reader at OD 490/560, by measuring $^3$H-thymidine incorporation into DNA following an 8 h culture with 1 µCu $^3$H-thymidine, harvesting the cells onto glass fiber mats using a cell harvester and measuring $^3$H-thymidine incorporation by liquid scintillation counting, or by staining techniques, such as crystal violet staining. Other suitable cellular assay systems are known in the art.

Alternatively, for anchorage independent cell growth, cells can be plated at $1 \times 10^3$ to $3 \times 10^3$ in 0.4% Seaplaque agarose in RPMI complete media, overlaying a bottom layer containing only 0.64% agar in RPMI complete media, for example in 24-well tissue culture plates. Complete media plus dilution series of compounds can be added to wells and incubated, for example at 37° C. in a 5% $CO_2$ incubator for a sufficient time, for example 10-14 days, preferably with repeated feedings of fresh media containing compound, typically at 3-4 day intervals. Colony formation and total cell mass can be monitored, average colony size and number of colonies can be quantitated according to methods known in the art, for example using image capture technology and image analysis software. Image capture technology and image analysis software, such as Image Pro Plus or media Cybernetics.

The advantageous properties of the compounds according to the invention can be additionally shown in other suitable assay systems, for example the assay systems described below. Preferably, the compounds according to the invention show an inhibiting activity in one or more of the assay systems. Suitable assays are known from the literature and can be readily performed by the skilled artisan (see for example Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., In Vitro 18:538-549).

The compounds according to the invention described in the examples are tested by the assays described below and are found to have kinase inhibitory activity. Other assays are known from the literature and can readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., In Vitro 18:538-549).

VEGF Receptor Kinase Assay

VEGF receptor kinase activity is measured by incorporation of radio-labelled phosphate into 4:1 polyglutamic acid/tyrosine substrate (pEY). The phosphorylated pEY product is trapped onto a filter membrane and the incorporation of radio-labelled phosphate is quantified by scintillation counting.

Materials:
VEGF Receptor Kinase

The intracellular tyrosine kinase domains of human KDR (Terman, B. I. et al. Oncogene (1991) Vol. 6, pp. 1677-1683.) and Flt-1 (Shibuya, M. et al. Oncogene (1990) Vol. 5, pp. 519-524) are cloned as glutathione S-transferase (GST) gene fusion proteins. This is accomplished by cloning the cytoplasmic domain of the KDR kinase as an in frame fusion at the carboxyl terminus of the GST gene. Soluble recombinant GST-kinase domain fusion proteins are expressed in *Spodoptera frugiperda* (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10% glycerol, 10 mg/ml each of leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% triton X-100, 10% glycerol, 10 mg/ml each of leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% triton X-100, 50% glycerol, 10 mg/ml each of leupeptin, pepstatin and aprotinin and 1 mM phenylmethylsulfonyl fluoride.

10× Reaction Buffer 200 mM Tris, pH 7.4, 1.0 M NaCl, 50 mM $MnCl_2$, 10 mM DTT and 5 mg/ml bovine serum albumin [BSA] (Sigma).

Enzyme Dilution Buffer 50 mM Tris, pH 7.4, 0.1 M NaCl, 1 mM DTT, 10% glycerol, 100 mg/ml BSA.

10× Substrate

750 µg/ml poly(glutamic acid/tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fibre 96 well plate.

Method A—Protein Purification

1. Sf21 cells are infected with recombinant virus at a multiplicity of infection of 5 virus particles/cell and grown at 27° C. for 48 hours.
2. All steps are performed at 4° C. Infected cells are harvested by centrifugation at 1000×g and lysed at 4° C. for 30 minutes with 1/10 volume of lysis buffer followed by centrifugation at 100,000×g for 1 hour. The supernatant is then passed over a glutathione Sepharose column (Pharmacia) equilibrated with lysis buffer and washed with 5 volumes of the same buffer followed by 5 volumes of wash buffer. Recombinant GST-KDR protein is eluted with wash buffer/10 mM reduced glutathione (Sigma) and dialysed against dialysis buffer.

Method B—VEGF Receptor Kinase Assay

1. Add 5 µl of inhibitor or control to the assay in 50% DMSO.
2. Add 35 µl of reaction mixture containing 5 µl of 10× reaction buffer, 5 µl of 25 mM ATP/10 µCi[$^{33}$P]ATP (Amersham) and 5 µl of 10× substrate.
3. Start the reaction by the addition of 10 µl of KDR (25 nM) in enzyme dilution buffer.
4. Mix and incubate at room temperature for 15 minutes.
5. Stop the reaction by the addition of 50 µl of stop solution.
6. Incubate for 15 minutes at 4° C.
7. Transfer a 90 µl aliquot to filter plate.
8. Aspirate and wash 3 times with wash solution.
9. Add 30 µl of scintillation cocktail, seal plate and count in a Wallace Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials:
HUVECs

HUVECs frozen as primary culture isolates are obtained from Clonetics Corp. Cells are maintained in endothelial growth medium (EGM; Clonetics) and are used for mitogenic assays at passages 3-7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) foetal bovine serum (Clonetics).

Test Compounds

Working stock solutions of test compounds are diluted serially in 100% dimethyl sulfoxide (DMSO) to 400 times greater than their desired final concentrations. Final dilutions to 1× concentration are made into assay medium immediately prior to addition to cells.

10× Growth Factors

Solutions of human VEGF 165 (500 ng/ml; R&D Systems) and bFGF (10 ng/ml; R&D Systems) are prepared in assay medium.

10× [$^3$H]thymidine

[Methyl-$^3$H]thymidine (20 Ci/mmol; Dupont-NEN) is diluted to 80 µCi/ml in low-glucose DMEM.

Cell Wash Medium

Hank's balanced salt solution (Mediatech) containing 1 mg/ml bovine serum albumin (Boehringer-Mannheim).

Cell Lysis Solution

1 N NaOH, 2% (w/v) $Na_2CO_3$.

Method 1

HUVEC monolayers maintained in EGM are harvested by trypsinisation and plated out at a density of 4000 cells per 100 µl of assay medium per well in 96-well plates. Cell growth is arrested for 24 hours at 37° C. in a humidified atmosphere containing 5% $CO_2$.

Method 2

Growth-arrest medium is replaced by 100 µl of assay medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

Method 3

After the 2-hour pre-treatment period, cells are stimulated by addition of 10 µl/well of either assay medium, 10×VEGF solution or 10× bFGF solution. Cells are then incubated at 37° C./5% $CO_2$.

Method 4

After 24 hours in the presence of growth factors, 10× [$^3$H]thymidine (10 µl/well) is added.

Method 5

Three days after addition of [$^3$H]thymidine, medium is removed by aspiration, and cells are washed twice with cell wash medium (400 µl/well followed by 200 µl/well). The washed, adherent cells are then solubilised by addition of cell lysis solution (100 µl/well) and warming to 37° C. for 30 minutes. Cell lysates are transferred to 7 ml glass scintillation vials containing 150 µl of water. Scintillation cocktail (5 ml/vial) is added, and cell-associated radioactivity is determined by liquid scintillation spectroscopy. According to these assays, the compounds of the formula I preferably are inhibitors of VEGF and are thus suitable for the inhibition of angiogenesis, such as in the treatment of ocular diseases, for example diabetic retinopathy, and for the treatment of carcinomas, for example solid tumours. The present compounds preferably inhibit VEGF-stimulated mitogenesis of human vascular endothelial cells in culture with IC50 values of 0.01-5.0 µM. These compounds preferably also show selectivity over related tyrosine kinases (for example FGFR1 and the Src family; for relationship between Src kinases and VEGFR kinases, see Eliceiri et al., Molecular Cell, Vol. 4, pp. 915-924, December 1999).

TIE-2 Enzyme Assay (TIE2-E)

The TIE-2 enzyme assay uses the LANCE method (Wallac) and GST-TIE2, baculovirus expressed recombinant constructs of the intracellular domains of human TIE2 (amino acids 762-1104, GenBank Accession # L06139) tagged by GST). The method measures the ability of the purified enzymes to catalyse the transfer of the γ-phosphate from ATP onto tyrosine residues in a biotinylated synthetic peptide, D1-15 (biotin-C6-LEARLVAYEGWVAGKKKamide). This peptide phosphorylation is detected using the following procedure: for enzyme preactivation, GST-TIE2 is incubated for 30 mins at room temperature with 2 mM ATP, 5 mM $MgCl_2$ and 12.5 mM DTT in 22.5 mM HEPES buffer (pH7.4). Pre-activated GST-TIE2 is incubated for 30 mins at room temperature in 96 well plates with 1 µM D1-15 peptide, 80 uM ATP, 10 mM $MgCl_2$, 0.1 mg/ml BSA and the test compound (diluted from a 10 mM stock in DMSO, final DMSO concentration is 2.4%) in 1 mM HEPES (pH7.4). The reaction is stopped by the addition of EDTA (final concentration 45 mM). Streptavidin linked-APC (allophycocyanin, Molecular Probe) and Europium-labeled anti-phosphorylated tyrosine antibody (Wallac) are then added at the final concentration of 17 µg/well and 2.1 µg/well, respectively. The APC signal is measured using an ARVO multilabel counter (e.g. Wallac Berthold Japan). The percent inhibition of activity is calculated relative to blank control wells. The concentration of test compound that inhibits 50% of activity ($IC_{50}$) is interpolated using nonlinear regression (Levernberg-Marquardt) and the equation, y=Vmax (1−x/(K+x))+Y2, where "K" is equal to the $IC_{50}$. The $IC_{50}$ values are then preferably converted to $pIC_{50}$ values, i.e., $-\log IC_{50}$ in Molar concentration.

As discussed herein, these signaling pathways are relevant for various disorders. Accordingly, by interacting with one or more of said signaling pathways, bisarylurea derivatives according to the invention are useful in the prevention and/or the treatment of disorders that are dependent from said signaling pathways.

The compounds according to the invention are preferably kinase modulators and more preferably kinase inhibitors. The compounds according to the invention are more preferably modulators and especially inhibitors of kinases, preferably kinases selected from the group consisting of serine/threonine kinases and receptor tyrosine kinases.

According to the invention, receptor tyrosine kinases are preferably selected from Tie-kinases, VEGFR-kinases and PDGFR-kinases.

According to the invention, serine/threonine kinases are preferably selected from raf-kinases, SAPK-kinases and p38-kinases.

According to the invention, kinases include, but are not limited to one or more Raf-kinases, one or more Tie-kinases, one or more VEGFR-kinases, one or more PDGFR-kinases, p38-kinase and/or SAPK2alpha.

Raf-kinases in this respect are respect preferably include or consist of A-Raf, B-Raf and c-Raf1.

Tie-kinases in this respect preferably include or consist of Tie-2 kinase.

VEGFR-kinases in this respect preferably include or consist of VEGFR-2 kinase.

Accordingly, the compounds according to the invention are preferably modulators and more preferably inhibitors of one or more kinases, selected from the group consisting of A-Raf, B-Raf, c-Raf1, Tie-1, Tie-2, Tie-3, PDGFR, VEGFR-1, VEGFR-2, VEGFR-3, p38-kinase and Ltk-kinase.

More preferably, the compounds according to the invention are dual specific or oligo specific modulators and more preferably inhibitors of two or more kinases, preferably two, three or four kinases, selected from the group consisting of A-Raf, B-Raf, c-Raf1, Tie-1, Tie-2, Tie-3, PDGFR, VEGFR-1, VEGFR-2, VEGFR-3, p38-kinase and Ltk-kinase, more preferably selected from Tie-2, PDGFR, VEGFR-2 and p38-kinase and especially selected from Tie-2, PDGFR and VEGFR-2.

Even more preferably, the compounds according to the invention are highly potent and/or specific inhibitors of Tie-2, VEGFR-2 and/or PDGFR kinases.

Especially preferably, the compounds according to the invention are highly potent and/or specific inhibitors of both Tie-2 and VEGFR-2 kinases.

Due to the kinase modulating or inhibiting properties of the compounds according to the invention, the compounds according to the invention preferably interact with one or more signalling pathways which are preferably cell signalling pathways, preferably by downregulating or inhibiting said signaling pathways. Examples for such signalling pathways include, but are not limited to the raf-kinase pathway, the Tie-kinase pathway, the VEGFR-kinase pathway, the PDGFR-kinase pathway, the p38-kinase pathway, the SAPK2alpha pathway and/or the Ras-pathway.

Modulation of the raf-kinase pathway plays an important role in various cancerous and noncancerous disorders, preferably cancerous disorders, such as dermatological tumors, haematological tumors, sarcomas, squamous cell cancer, gastric cancer, head cancer, neck cancer, oesophageal cancer, lymphoma, ovary cancer, uterine cancer and/or prostate cancer. Modulation of the raf-kinase pathway plays a even more important role in various cancer types which show a constitutive activation of the raf-kinase dependent signalling pathway, such as melanoma, colorectal cancer, lung cancer, brain cancer, pancreatic cancer, breast cancer, gynaecological cancer, ovarian cancer, thyroid cancer, chronic leukaemia and acute leukaemia, bladder cancer, hepatic cancer and/or renal cancer. Modulation of the raf-kinase pathway plays also an important role in infection diseases, preferably the infection diseases as mentioned above/below and especially in *Helicobacter pylori* infections, such as *Helicobacter pylori* infection during peptic ulcer disease.

Modulation of the Tie-2-kinase pathway plays an important role in various cancerous and noncancerous disorders, preferably cancerous disorders, and especially disorders characterized by cellular proliferation in the area of disorders associated with neo-vascularization and/or vascular permeability; such disorders preferably include blood vessel proliferative disorders, including arthritis and restenosis; fibrotic disorders, including hepatic cirrhosis and atherosclerosis; mesangial cell proliferative disorders, including glomerulonephritis, diabetic nephropathy, malignant nephrosclerosis, thrombotic microangiopathy syndromes, organ transplant rejection and glomerulopathies; and metabolic disorders, including psoriasis, diabetes mellitus, chronic wound healing, inflammation and neurodegenerative diseases.

One or more of the signalling pathways mentioned above/ below and especially the VEGFR-kinase pathway plays an important role in angiogenesis. Accordingly, due to the kinase modulating or inhibiting properties of the compounds according to the invention, the compounds according to the invention are suitable for the prophylaxis and/or treatment of pathological processes or disorders caused, mediated and/or propagated by angiogenesis, for example by inducing anti-angiogenesis. Pathological processes or disorders caused, mediated and/or propagated by angiogenesis include, but are not limited to tumors, especially solid tumors, arthritis, especially rheumatic or rheumatoid arthritis, diabetic retinopathy, psoriasis, restenosis; fibrotic disorders; mesangial cell proliferative disorders, diabetic nephropathy, malignant nephrosclerosis, thrombotic microangiopathy syndromes, organ transplant rejection, glomerulopathies, metabolic disorders, inflammation and neurodegenerative diseases, and especially solid tumors, rheumatic arthritis, diabetic retinopathy and psoriasis.

Modulation of the p38-signalling pathway plays an important role in various cancerous and also in various noncancerous disorders, such as fibrosis, atherosclerosis, restenosis, vascular disease, cardiovascular disease, inflammation, renal disease and/or angiogenesis, and especially noncancerous disorders such as rheumatoid arthritis, inflammation, autoimmune disease, chronic obstructive pulmonary disease, asthma and/or inflammatory bowel disease.

Modulation of the PDGF-signalling pathway plays an important role in various cancerous and although in various noncancerous disorders, such as rheumatoid arthritis, inflammation, autoimmune disease, chronic obstructive pulmonary disease, asthma and/or inflammatory bowel disease, and especially noncancerous disorders such as fibrosis, atherosclerosis, restenosis, vascular disease, cardiovascular disease, inflammation, renal disease and/or angiogenesis.

A further preferred subject of the invention are bisarylurea derivatives according to the invention as promoters or inhibitors, preferably as inhibitors of one or more raf-kinases, selected from the group consisting of A-raf, B-raf and c-raf1. Especially preferred subject of the invention are bisarylurea derivatives according to the invention as promoters or inhibitors, preferably as inhibitors of c-raf1 or B-raf.

Thus, subject of the present invention are bisarylurea derivatives according to the invention as medicaments. Subject of the present invention are bisarylurea derivatives according to the invention as medicament active ingredients. Further subject of the present invention is the use of one or more bisarylurea derivatives according to the invention as a pharmaceutical. Further subject of the present invention is the use of one or more bisarylurea derivatives according to the invention in the treatment and/or the prophylaxis of disorders, preferably the disorders described herein, more preferred disorders that are caused, mediated and/or propagated by signalling pathways discussed herein, even more preferred disorders that are caused, mediated and/or propagated by one or more kinases, preferably selected from serine/threonine kinases and receptor tyrosine kinases, and especially disorders that are caused, mediated and/or propagated by raf-kinases, especially B-raf and/or c-raf1, Tie-kinases, especially Tie-2, and/or VEGFR-kinases, especially VEGFR-2.

Usually, the disorders discussed herein are divided into two groups, hyperproliferative and non hyperproliferative disorders. In this context, psioarsis, arthritis, inflammation, endometriosis, scarring, begnin prostatic hyperplasia, immunological diseases, autoimmune diseases and immunodeficiency diseases are to be regarded as noncancerous disorders, of which arthritis, inflammation, immunological diseases, autoimmune diseases and immunodeficiency diseases are usually regarded as non hyperproliferative disorders. In this context, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia are to be regarded as cancerous disorders, all of which are usually regarded as hyperproliferative disorders. Especially cancerous cell growth and especially cancerous cell growth mediated by raf-kinase is a disorder which is a target of the present invention. Subject of the present invention therefore are bisarylurea derivatives according to the invention as medicaments and/or medicament active ingredients in the treatment and/or the prophylaxis of said disorders and the use of bisarylurea derivatives according to the invention for the manufacture of a pharmaceutical for the treatment and/or the prophylaxis of said disorders as well as a method of treatment of said disorders, comprising administering one or more bisarylurea derivatives according to the invention to a patient in need of such an administration. Subject of the present invention therefore are bisarylurea derivatives according to the invention as medicaments and/or medicament active ingredients in the treatment and/or the prophylaxis said disorders and the use of bisarylurea derivatives according to the invention for the manufacture of a pharmaceutical for the treatment and/or the prophylaxis of said disorders as well as a method of treatment of said disorders, comprising administering one or more bisarylurea derivatives according to the invention to a patient in need of such an administration.

Accordingly, subject of the present invention are pharmaceutical compositions that contain one or more bisarylurea derivatives according to the invention. Subject of the present invention are especially pharmaceutical compositions that contain one or more bisarylurea derivatives according to the invention and one or more additional compounds (other than the compounds of the instant invention), preferably selected from the group consisting of physiologically acceptable excipients, auxiliaries, adjuvants, carriers and pharmaceutically active ingredients other than the compounds according to the invention.

Accordingly, subject of the present invention is a process for the manufacture of a pharmaceutical composition, wherein one or more bisarylurea derivatives according to the invention and one or more compounds (other than the compounds of the instant invention), preferably selected from the group consisting of carriers, excipients, auxiliaries, adjuvants and pharmaceutically active ingredients other than the compounds according to the invention.

Accordingly, the use of the compounds according to the invention in the treatment of Hyperproliferative disorders is a subject of the instant invention.

Accordingly, the use of the compounds according to the invention for producing a medicament for the treatment of hyperproliferative disorders is a subject of the instant invention.

The compounds according to the invention can preferably be combined in an advantageous manner with known anti-cancer agents. Examples of such known anti-cancer agents comprise:

Estrogen receptor modulators, androgen receptor modulators, retinoid receptor modulators, cytotoxic agents, antiproliferative agents, prenyl-protein transferase inhibitors, HMG-CoA-reductase-inhibitors, HIV-protease-inhibitors, reverse-transcriptase-inhibitors as well as further angiogenesis inhibitors. The compounds according to the invention preferably are especially suitable for administration in combination with radiotherapy. The term "estrogen receptor modulators" preferably relates to compounds which modulate or preferably inhibit the binding of estrogen to the respective receptor, independently of the respective mode of action. Examples of estrogen receptor modulators in this respect include, but are not limited to Tamoxifen, Raloxifen, Idoxifen, LY353381, LY117081, Toremifen, Fulvestrant, 4-[7-(2,2-Dimethyl-1-oxopropoxy-4-methyl-2-[4-[2-(1-piperidinyl)ethoxy]phenyl]-2H-1-benzopyrane-3-yl]phenyl-2,2-dimethyl-propanoate, 4,4'-Dihydroxybenzophenone-2,4-dinitrophenylhydrazone and SH646.

The term "androgen receptor modulators" preferably relates to compounds which modulate or preferably inhibit the binding of androgens to the respective receptor, independently of the respective mode of action. Androgen receptor modulators in this respect include, but are not limited to 5α-reductase-inhibitors, Nilutamide, Flutamide, Bicalutamide, Liarozole and Abiraterone-acetate.

The term "retinoid receptor modulators" preferably relates to compounds which modulate or preferably inhibit the binding of retinoids to the respective receptor, independently of the respective mode of action. Retinoid receptor modulators in this respect include, but are not limited to Bexarotene, Tretinoine, 13-cis-retinoic acid, 9-cis-retinoic acid, α-Difluoromethylornithine, ILX23-7553, trans-N-(4'-Hydroxyphenyl)retinamide and N-4-Carboxyphenylretinamide.

The term "cytotoxic agents" preferably relates to compounds which preferably directly interact with the cell functions and thus induce cell death (apoptosis) or which modulate or preferably inhibit cell mitosis. Cytotoxic agents in this respect include, but are not limited to alkylating agents, tumour necrosis factors, intercalating agents, microtubuline inhibitors and topoisomerase inhibitors.

Examples of cytotoxic agents in this respect include, but are not limited to Tirapazimine, Sertenef, Cachectine, Ifosfamide, Tasonermine, Lonidamine, Carboplatine, Altretamine, Prednimustine, Dibromdulcit, Ranimustine, Fotemustine, Nedaplatine, Oxaliplatine, Temozolomide, Heptaplatine, Estramustine, Improsulfan-tosylate, Trofosfamide, Nimustine, Dibrospidium-chloride, Pumitepa, Lobaplatine, Satraplatine, Profiromycine, Cisplatin, Iro-fulvene, Dexifosfamide, cis-Amino dichloro(2-methylpyridine)platin, Benzylguanine, Glufosfamide, GPX100, (trans,trans,trans)-bis-mu-(hexan-1,6-diamine)-mu-[diamine-platin(II)]bis[diamine(chloro)platin(II)]-tetrachloride, Diarizidinylspermine, Arsentrioxide, 1-(11-Dodecylamino-10-hydroxyundecyl)-3,7-dimethylxanthine, Zorubicine, Idarubicine, Daunorubicine, Bisantrene, Mitoxantrone, Pirarubicine, Pinafide, Valrubicine, Amrubicine, Antineoplastone, 3'-Desamino-3'-morpholino-13-desoxo-10-hydroxycaminomycine, Annamycine, Galarubicine, Elinafide, MEN10755 and 4-Desmethoxy-3-desamino-3-aziridinyl-4-methylsulfonyldaunorubicin (see for example WO 00/50032).

Examples of microtubulin inhibitors in this respect include, but are not limited to Paclitaxel, Vindesine-sulfate, 3',4'-Dideshydro-4'-desoxy-8'-norvincaleukoblastine, Docetaxol, Rhizoxine, Dolastatine, Mivobuine-isethionate, Auristatine, Cemadotine, RPR109881, BMS184476, Vinflunine, Cryptophycine, 2,3,4,5,6-pentafluoro-N-(3-fluoro-4-methoxyphenyl)benzene sulfonamide, Anhydrovinblastine, N,N-dimethyl-L-valyl-L-valyl-N-methyl-L-valyl-L-prolyl-L-proine-t-butylamide, TDX258 and BMS188797.

Examples of topoisomerase inhibitors in this respect include, but are not limited to Topotecan, Hycaptamine, Irinotecan, Rubitecan, 6-Ethoxypropionyl-3',4'-O-exo-benzyliden-chartreusine, 9-Methoxy-N,N-dimethyl-5-nitropyrazolo[3,4,5-kl]acridine-2-(6H)propanamine, 1-Amino-9-ethyl-5-fluoro-2,3-dihydro-9-hydroxy-4-methyl-1H,12H-benzo[de]pyrano-[3',4':b,7]indolizino[1,2b]chinoine-10,13 (9H,15H)-dione, Lurtotecane, 7-[2-(N-Isopropylamino) ethyl]-(20S)camptothecine, BNP1350, BNPI1100, BN80915, BN80942, Etoposide-phosphate, Teniposide, Sobuzoxane, 2'-Dimethylamino-2'-desoxy-etoposide, GL331, N-[2-(Dimethylamino)ethyl]-9-hydroxy-5,6-dimethyl-6H-pyrido[4,3-b]carbazol-1-carboxamide, Asulacrine, (5a,5aB,8aa,9b)-9-[2-[N-[2-(Dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(Methylen-dioxy)-5-methyl-7-hydroxy-8-methoxybenzo[c]phenanthridinium, 6,9-Bis[(2-aminoethyl)amino]benzo[g]isochinoine-5,10-dione, 5-(3-Aminopropylamino)-7,10-dihydroxy-2-(2-hydroxyethylaminomethyl)-6H-pyrazolo[4,5,1-de]-acridine-6-one, N-[1-[2(Diethylamino)ethylamino]-7-methoxy-9-oxo-9H-thio-xanthen-4-ylmethyl]formamide, N-(2-(Dimethyl-amino)-ethyl)acridine-4-carboxamide, 6-[[2-(Dimethylamino)-ethyl]amino]-3-hydroxy-7H-indeno[2,1-c]chinoine-7-one and Dimesna.

The term "antiproliferative agents" preferably includes, but is not limited to siRNA, antisense-RNA- and -DNA-Oligonucleotides, such as G3139, ODN698, RVASKRAS, GEM231 and INX3001, as well as antimetabolites, such as Enocitabine, Carmofur, Tegafur, Pentostatine, Doxifluridine, Trimetrexate, Fludarabine, Capecitabine, Galocitabine, Cytarabin-ocfosfate, Fosteabin-Sodium hydrate, Raltitrexede, Paltitrexede, Emitefur, Tiazofurine, Decitabine, Nolatrexede, Pemetrexede, Nelzarabine, 2'-Desoxy-2'-methylidencytidine, 2'-Fluoromethylen-2'-desoxycytidine, N-[5-(2,3-Dihydrobenzofuryl)sulfonyl]-N'-(3,4-dichlorophenyl)harnstoff, N6-[4-Desoxy-4-[N2-[2(E),4(E)-tetradecadienoyl]glycylamino]-L-glycero-B-L-manno-hepto-pyranosyl]adenine, Aplidine, Ecteinascidine, Troxacitabine, 4-[2-Amino-4-oxo-4,6,7,8-tetrahydro-3H-pyrimidino[5,4-b][1,4]thiazin-6-yl-(S)-ethyl]-2,5-thienoyl-L-glutamic acid, Aminopterine, 5-Fluorouracil, Alanosine, 11-Acetyl-8-(carbamoyloxymethyl)-4-formyl-6-methoxy-14-oxa-1,11-diazatetracyclo-(7.4.1.0.0)-tetradeca-2,4,6-trien-9-ylacetic acid ester, Swainsonine, Lometrexol, Dexrazoxane, Methioninase, 2'-cyan-2'-desoxy-N4-palmitoyl-1-B-D-Arabinofuranosylcytosin and 3-Aminopyridine-2-carboxaldehyde-thiosemicarbazone.

The "antiproliferative agents" preferably further include monoclonal antibodies against growth factors other than the antibodies cited with respect to the "angiogenesis inhibitors", such as Trastuzumab, as well as tumour surpressor genes, such as p53, which can be administered via recombinant virus-driven gene transfer (see for example U.S. Pat. No. 6,069,134).

The compounds according to the invention can preferably be combined in an advantageous manner with radiotherapy and/or known anti-cancer agents, preferably known anti-cancer agents as described herein.

The meaning of the term radiotherapy is known in the art. According to the invention, the term radiotherapy preferably includes, but is not limited to external beam radiation, administration of radioactive materials, such as radio isotopes radio nuclides, and/or radio immuno therapy (RIT).

Accordingly, the compounds of the present invention can be used to provide additive or preferably synergistic effects with existing cancer chemotherapies, and/or be used to restore effectiveness of existing cancer chemotherapies and radiation.

Above and below, all temperatures are given in ° C. In the examples below, "conventional work-up" means that the organic phase is washed with saturated $NaHCO_3$ solution, if desired with water and saturated NaCl solution, the phases are separated, the organic phase is dried over sodium sulfate and evaporated, and the product is purified by chromatography on silica gel, by preparative HPLC and/or by crystallization.

The present invention relates to bisarylurea derivatives of formula I, the use of the compounds of formula I as inhibitors of one or more kinases, the use of the compounds of formula I for the manufacture of a pharmaceutical composition and a method of treatment, comprising administering said pharmaceutical composition to a patient.

EXAMPLES i) Synthesis of the Pyridine Units

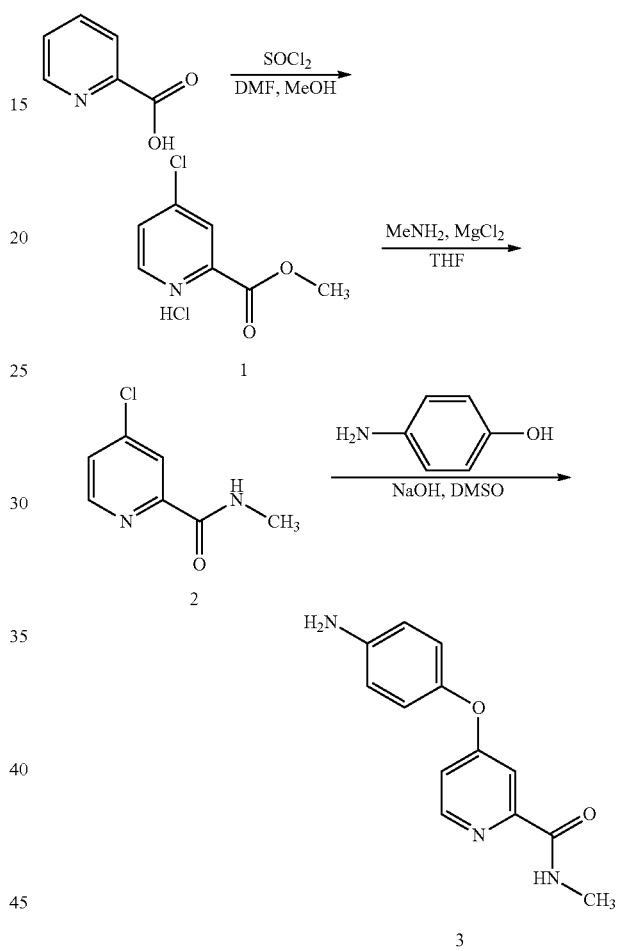

a) 750 ml of thionyl chloride are heated to 45° C. under an $N_2$ atmosphere, and 23 ml of DMF are added dropwise. 250 g (2.031 mol) of pyridine-2-carboxylic acid are subsequently added in portions, and the reaction mixture is stirred at 45° C. for a further 15 minutes and at 80° C. for 24 hours. The yellow suspension is evaporated, and the residue is entrained a number of times with toluene. The oily residue is dissolved in 180 ml of toluene, the solution is cooled to 0° C., and 110 ml of methanol are added dropwise. The suspension is stirred for a further hour, and the precipitated solid is filtered off with suction and rinsed with toluene. The resultant crude product is recrystallised a number of times from acetone and dried in a vacuum drying cabinet.

Yield: 140 g (33%) of 1, pale crystals b) 140 g (0.673 mol) of 1 are stirred with 32 g (0.336 mol) of magnesium chloride and 2 l of THF at room temperature After 5 minutes, 1.36 l (2.369 mol) of methylamine are added dropwise over the course of 20 minutes. The suspension is stirred at room temperature for a further 16 hours. 1.3 l of water and 680 ml of 1N HCl solution are added to the reaction mixture, and the mixture is extracted with ethyl acetate (3×1 l). The combined organic phases are washed with a saturated NaCl solution, dried using sodium sulfate, filtered and evaporated. The crude product is taken up in 300 ml of ethyl acetate and extracted with 200 ml of 1N HCl solution. The aqueous phase is adjusted to pH 9 using a 25% $NH_4OH$ solution and extracted with ethyl acetate (2×400 ml). The organic phase is dried using sodium sulfate, filtered and evaporated.

Yield: 93 g (81%) of 2, brown oil c) 50 g (0.293 mol) of 2 and 32.6 g (0.293 mol) of 4-aminophenol are dissolved in DMSO, and 29.3 g (0.733 mol) of sodium hydroxide are slowly added. The solution is then heated at 100° C. overnight. After a further 29.3 g (0.733 mol) of sodium hydroxide had been added, the reaction mixture is again stirred at 100° C. overnight. The reaction mixture is cooled to room temperature, ice-water is added, and the mixture is extracted a number of times with diethyl ether. The combined organic phases are dried using sodium sulfate, filtered and evaporated.

Yield: 36 g (51%) of 3, brown oil ii) Synthesis of the Anilines

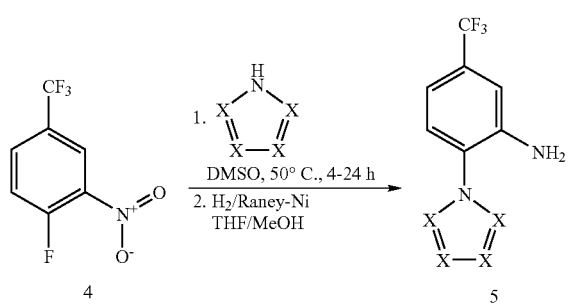

X = N, CH

4-Fluoro-3-nitrobenzotrifluoride is dissolved in DMSO (1.5 ml/mmol), treated with 1 equivalent of the respective azole and stirred at 50° C. for 4-24 h. The reaction mixture is cooled to room temperature, treated with water (5-10 ml/mmol) and extracted twice with ethyl acetate (10-20 ml/mmol). The organic phase is washed with brine, dried over $Na_2SO_4$, filtered and evaporated to dryness. The residue can be further purified by column chromatography on silica gel.

The accordingly obtained nitro compound is hydrogenated with $H_2$ and Pd on charcoal (5%, moisturised with water) in THF at room temperature until a full conversion is achieved. The catalyst is removed by filtration, rinsed with methanol, and the filtrate is evaporated to dryness. The obtained residues can be employed in the next steps without further purification.

TABLE 1

| Nr. | $R^7$—H | Struktur | HPLC | HPLC-MS |
|-----|---------|----------|------|---------|
| 5a | 1,2,4-triazol-1-yl | | 2.20 (Method A) | 229 (M + H) |
| 5b | 1,2,4-triazol-1-yl (isomer) | | 2.35 (Method A) | 229 (M + H) |
| 5c | 1,2,3-triazol-1-yl | | 2.47 (Method A) | 229 (M + H) |
| 5d | imidazol-1-yl | | 2.06 (Method A) | 228 (M + H) |
| 5e | pyrazol-1-yl | | 2.39 (Method B) | 228 (M + H) |

TABLE 1-continued

| Nr. | R⁷—H | Struktur | HPLC | HPLC-MS |
|---|---|---|---|---|
| 5f | 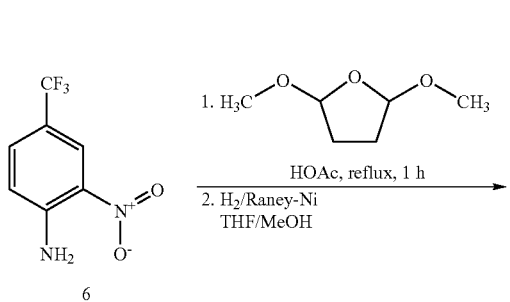 | | | |

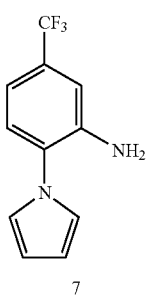

6

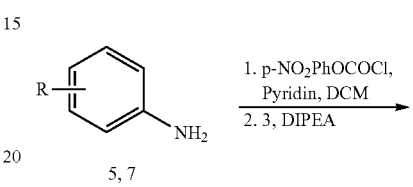

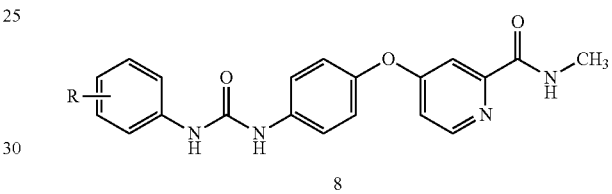

7

4-Fluoro-2-nitroaniline 6 (1.03 g, 5 mmol) is dissolved in 10 ml acetic acid, treated cautiously with 2,5-dimethoxy tetrahydrofurane (647 μl, 5 mmol) and heated to reflux for 60 min. After cooling down the reaction mixture, the solvent is removed by distillation under reduced pressure. The residue is taken up in 50 ml ethylacetate, the resulting solution washed with 30 ml semi-concentrated $NaHCO_3$ solution and 30 ml brine, dried using sodium sulfate and evaporated to dryness.

Yield: 1.12 g, brown oil, HPLC: 2.85 (Method B), HPLC-MS: 257 (M+H)

The accordingly obtained nitro compound is hydrogenated with $H_2$ and Pd on charcoal (5%, moisturised with water) in THF at room temperature until a full conversion is achieved. The catalyst is removed by filtration, rinsed with methanol, and the filtrate is evaporated to dryness.

Yield: 1.0 g, brown oil, HPLC: 2.81 (Method B), HPLC-MS: 227 (M+H)

Synthesis of the Ureas

200 μmol of the respective aniline 5a-e or 7 is dissolved in dichloromethane together with 220 μmol p-nitrophenyl chloroformate, treated with 220 μmol pyridine at room temperature and stirred for 20-35 min. After the reaction is completed, 200 μmol 3 and 400 μmol DIPEA are added and the reaction mixture is stirred at room temperature until a full conversion is achieved (30 min-17 h). The reaction mixture is diluted with dichloromethane, successively extracted 2× with 1N NaOH, 1× with water and 1× with brine, dried over $Na_2SO_4$, filtered and evaporated. The accordingly obtained crude product is purified according to the following variants:

Variant A: the residue is purified by column chromatography on silica gel.

Variant B: the residue is purified by preparative HPLC (water/acetonitrile, 0.01% HCOOH).

TABLE 2

| Nr. | Struktur | HPLC | HPLC-MS |
|---|---|---|---|
| 8a | | 2.50 (Method A) | 498 (M + H) |

TABLE 2-continued

| Nr. | Struktur | HPLC | HPLC-MS |
|---|---|---|---|
| 8b | | 2.65 (Method A) | 498 (M + H) |
| 8c | | 2.47 (Method A) | 498 (M + H) |
| 8d | | 2.38 (Method A) | 497 (M + H) |
| 8e | | 2.85 (Method B) | 497 (M + H) |
| 8f | | | |

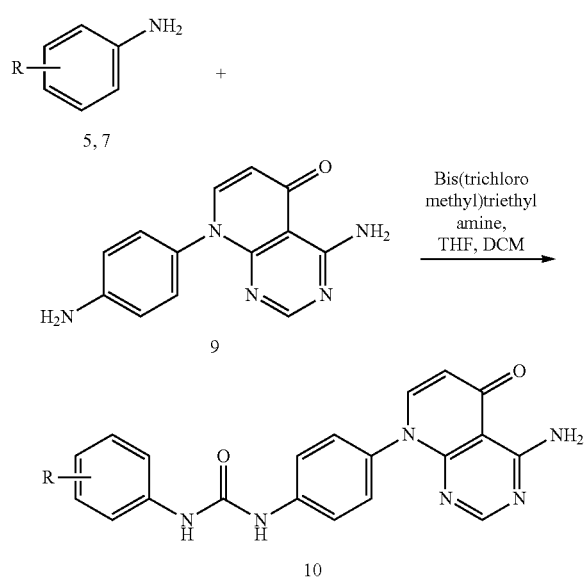

The respective aniline 5a-e or 7 is dissolved in THF (10-20 ml/mmol) and 2.5 equivalents DIPEA and added slowly dropwise to a solution of 0.33 equivalents triphosgen in THF (10-20 ml/mmol aniline). Stirring is continued for 15 min at −70° C. and then a solution of 9 in THF (10-20 ml/mmol; if salts are applied, compound 9 is neutralised with 1.25 equivalents DIPEA) is added dropwise. Stirring is continued for 1 h at −70° C. Subsequently, the cooling bath is removed and the reaction mixture is slowly warmed up to room temperature under stirring. After 20 h, the reaction mixture is concentrated, taken up in ethylacetate and 5% $KHSO_4$-solution, washed twice with 5% $KHSO_4$-solution and 5% $NaHCO_3$-solution, dried over $Na_2SO_4$ and evaporated.

TABLE 3

| Nr. | Struktur | HPLC | HPLC-MS |
|---|---|---|---|
| 10a | ![structure] | 2.65 (Method C) | 508 (M + H) |

Retention times (Rt) as disclosed herein are, if not indicated otherwise, HPLC retention times (in minutes), obtained according the following methods:
HPLC-Methods:
Method A: flow rate: 3 ml/min; 0.0-0.5 min: 99:1: (water+0.1 Vol % TFA):(acetonitrile+0.1 Vol % TFA); 0.5-3.5 min: gradient from 99:1 to 0:100 (water+0.1 Vol % TFA):(acetonitrile+0.1 Vol % TFA); 3.5 to 4.5 min: acetonitrile+0.1 Vol % TFA; column: Chromolith SpeedROD RP18e 50-4.6; wavelength: 220 nm.
Method B: flow rate: 3 ml/min; 0.0-3.5 min: gradient from 90:10 to 0:100 (water+0.1 Vol % TFA):(acetonitrile+0.1 Vol % TFA); 3.5 to 4.3 min: acetonitrile+0.1 Vol % TFA; column: Chromolith SpeedROD RP18e 50-4.6; wavelength: 220 nm.
Method C: flow rate: 2 ml/min; 0.0-3.5 min: gradient von 80:200 auf 0:100 (water+0.1 Vol % TFA):(acetonitrile/water 9:1+0.1 Vol % TFA); 3.5 to 5 min: acetonitrile/water 9:1+0.1 Vol % TFA; column: Chromolith SpeedROD RP18e 50-4.6; wavelength: 220 nm.

The compounds disclosed herein can preferably be produced according to the procedures described herein or in an analogous manner thereof.

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water is prepared. It is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated Tablets

Analogously to Example E, tablets are pressed and are then coated in a customary manner using a coating of sucrose, potato starch, talc, tragacanth and colourant.

Example G

Capsules 2 kg of active compound of the formula I are dispensed into hard gelatin capsules in a customary manner such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

The invention claimed is:

1. Heterocyclic substituted bisarylurea compound of formula I

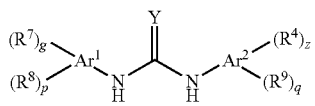

wherein $Ar^1$, $Ar^2$ are phenyl, $R^4$ is independently selected from residues of the formula $(X—Ar^3)_\alpha—(R^{10})_r$, wherein $Ar^3$ is independently selected from unsubstituted or substituted unsaturated or aromatic heterocyclic residues containing 2 to 10 carbon atoms and one or more heteroatoms, independently selected from N, O and S, $\alpha$ is 0, 1 or 2, $R^{10}$ is independently selected from the meanings given for $R^8$ and $R^9$, and r is 0, 1, 2, 3, 4 or 5;

z is 0, 1, 2, 3, 4 or 5, $R^7$ is a nitrogen containing heterocylic moiety, directly bound to $Ar^1$ via a nitrogen atom, said nitrogen containing heterocyclic moiety being independently selected from $Het^1$ wherein $Het^1$ is an unsaturated or aromatic heterocyclic residue comprising 5, 6 or 7 ring atoms which contains 1 to 4 nitrogen atoms and optionally 1 or 2 additional heteroatoms selected from O and S, whereby said unsaturated or aromatic heterocyclic residue is unsubstituted or substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $R^8$ and $R^9$ are independently selected from a group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOOR^{13}$, $(CH_2)_nCOR^{13}$, $(CH_2)_nCONR^{11}R^{12}$, $(CH_2)_nNR^{11}COR^{13}$, $(CH_2)_nNR^{11}CONR^{11}R^{12}$, $(CH_2)_nNR^{11}SO_2A$, $(CH_2)_nSO_2NR^{11}R^{12}$, $(CH_2)_nS(O)_uNR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, CH=N—OA, $CH_2CH=N$—OA, $(CH_2)_nNHOA$, $(CH_2)_nCH=N—R^{11}$, $(CH_2)_nOC(O)NR^{11}R^{12}$, $(CH_2)_nNR^{11}COOR^{13}$, $(CH_2)_nN(R^{11})CH_2CH_2OR^{13}$, $(CH_2)_nN(R^{11})CH_2CH_2OCF_3$, $(CH_2)_nN(R^{11})C(R^{13})HCOOR^{12}$, $(CH_2)_nN(R^{11})C(R^{13})HCOR^{11}$, $(CH_2)_nN(R^{11})CH_2CH_2N(R^{12})CH_2COOR^{11}$, $(CH_2)_nN(R^{11})CH_2CH_2NR^{11}R^{12}$, CH=CHCOOR$^{13}$, CH=CHCH$_2$NR$^{11}$R$^{12}$, CH=CHCH$_2$NR$^{11}$R$^{12}$, CH=CHCH$_2$OR$^{13}$, $(CH_2)_nN(COOR^{13})COOR^{14}$, $(CH_2)_nN(CONH_2)COOR^{13}$, $(CH_2)_nN(CONH_2)CONH_2$, $(CH_2)_nN(CH_2COOR^{13})COOR^{14}$, $(CH_2)_nN(CH_2CONH_2)COOR^{13}$, $(CH_2)_nN(CH_2CONH_2)CONH_2$, $(CH_2)_nCHR^{13}COR^{14}$, $(CH_2)_nCHR^{13}COOR^{14}$, $(CH_2)_nCHR^{13}CH_2OR^{14}$, $(CH_2)_nOCN(CH_2)_nNCO$, Het$^9$, OHet$^9$, N(R$^{11}$)Het$^9$, $(CR^5R^6)_kHet^9$, $O(CR^5R^6)_kHet^9$, $N(R^{11})(CR^5R^6)_kHet^9$, $(CR^5R^6)_kNR^{11}R^{12}$, $(CR^5R^6)_kOR^{13}$, $O(CR^5R^6)_kNR^{11}R^{12}$, $NR^{11}(CR^5R^6)_kNR^{11}R^{12}$, $O(CR^5R^6)_kR^{13}$, $NR^{11}(CR^5R^6)_kR^{13}$, $O(CR^5R^6)_kOR^{13}$, $NR^{11}(CR^5R^6)_kOR^{13}$, wherein $R^5$, $R^6$ are in each case independently from one another selected from H and A, $R^{11}$, $R^{12}$ are independently selected from a group consisting of H, A, $(CH_2)_mAr^7$ and $(CH_2)_mHet^9$, or in $NR^{11}R^{12}$, $R^{11}$ and $R^{12}$ form, together with the N-atom they are bound to, a 5-, 6- or 7-membered heterocyclus which optionally contains 1 or 2 additional hetero atoms, selected from N, O and S; whereby said heterocyclic residue optionally is substituted by one or more substituent, selected from A, $R^{13}$, =O, =S and =N—$R^{14}$, $R^{13}$, $R^{14}$ are independently selected from a group consisting of H, Hal, A, $(CH_2)_mAr^8$ and $(CH_2)_mHet^9$, A is selected from the group consisting of alkyl, alkenyl, cycloalkyl, alkylenecycloalkyl, alkoxy, alkoxyalkyl and saturated heterocyclyl, $Ar^7$, $Ar^8$ are independently from one another aromatic hydrocarbon residues comprising 5 to 12 carbon atoms which are optionally substituted by one or more substituents, selected from a group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, Het$^9$ is a saturated, unsaturated or aromatic heterocyclic residue said heterocyclic residue is optionally substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$, $R^{15}$, $R^{16}$ are independently selected from a group consisting of H, A, and $(CH_2)_mAr^6$, wherein $Ar^6$ is a 5- or 6-membered aromatic hydrocarbon which is optionally substituted by one or more substituents selected from a group consisting of methyl, ethyl, propyl, 2-propyl, tert.-butyl, Hal, CN, OH, $NH_2$ and $CF_3$, k, n and m are independently of one another 0, 1, 2, 3, 4, or 5, X is O, Y is selected from O, S, $NR^{21}$, $C(R^{22})$—$NO_2$, $C(R^{22})$—CN and $C(CN)_2$, wherein $R^{21}$ is independently selected from the meanings given for $R^{13}$, $R^{14}$ and $R^{22}$ is independently selected from the meanings given for $R^{11}$, $R^{12}$, g is 1, 2 or 3, p is 0, 1, 2, 3, 4 or 5, q is 0, 1, 2, 3 or 4, u is 0, 1, 2 or 3, and Hal is independently selected from a group consisting of F, Cl, Br and I;

or a pharmaceutically acceptable salt or stereoisomer thereof.

2. Bisarylurea compound according to claim 1, wherein $R^4$ is independently selected from residues of the formula $(Ar^3)_\alpha$—$(R^{10})_r$, wherein α is 0, 1 or 2, $R^{10}$ is independently selected from the meanings given for $R^8$ and $R^9$, r is 0, 1, 2, 3, 4 or 5, z is 0, 1, 2, 3, 4 or 5, $R^7$ is a nitrogen containing heterocylic moiety, directly bound to $Ar^1$ via a nitrogen atom, said nitrogen containing heterocyclic moiety being independently selected from $Het^1$, $Het^2$ and $Het^3$, wherein $Het^1$ is an unsaturated or aromatic heterocyclic residue comprising 5 or 6 ring atoms which contains 1 to 4 nitrogen atoms and optionally 1 or 2 additional heteroatoms selected from O and S, whereby said unsaturated or aromatic heterocyclic residue is unsubstituted or substituted by one or more substituents, selected from a group consisting of A, $R^{13}$, =O, =S, =N—$R^{14}$, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2NR^{15}R^{16}$, $S(O)_uA$ and $OOCR^{15}$;

$R^8$ and $R^9$ are independently selected from a group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_nNR^{11}R^{12}$, $(CH_2)_nO(CH_2)_kNR^{11}R^{12}$, $(CH_2)_n NR^{11}(CH_2)_kNR^{11}R^{12}$, $(CH_2)_nO(CH_2)_kOR^{11}$, $(CH_2)_n NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nNR^{11}COR^{13}$, $(CH_2)_n NR^{11}CONR^{11}R^{12}$, $(CH_2)_nNR^{11}SO_2A$, $(CH_2)_n SO_2NR^{11}R^{12}$, $(CH_2)_nS(O)_uNR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, $(CH_2)_n NHOA$, $(CH_2)_nNR^{11}COOR^{13}$, $(CH_2)_nN(R^{11})$ $CH_2CH_2OR^{13}$, $(CH_2)_nN(R^{11})CH_2CH_2OCF_3$, $(CH_2)_nN (R^{11})C(R^{13})HCOOR^{12}$, $(CH_2)_nN(R^{11})C(R^{13})HCOR^{11}$, $(CH_2)_nN(COOR^{13})COOR^{14}$, $(CH_2)_nN(CONH_2)$ $COOR^{13}$, $(CH_2)_nN(CONH_2)CONH_2$, $(CH_2)_nN (CH_2COOR^{13})COOR^{14}$, $(CH_2)_nN(CH_2CONH_2)$ $COOR^{13}$, $(CH_2)_nN(CH_2CONH_2)CONH_2$, $(CH_2)_n CHR^{13}COR^{14}$, $(CH_2)_nCHR^{13}COOR^{14}$ and $(CH_2)_n CHR^{13}CH_2OR^{14}$, and/or selected from the group consisting $Het^9$, $OHet^9$, $N(R^{11})Het^9$, $(CR^5R^6)_kHet^9$, $O(CR^5R^6)_kHet^9$, $N(R^{11}) (CR^5R^6)_kHet^9$, $(CR^5R^6)_kNR^{11}R^{12}$, $(CR^5R^6)_kOR^{13}$, $O(CR^5R^6)_kNR^{11}R^{12}$, $NR^{11}(CR^5R^6)_kNR^{11}R^{12}$, $O(CR^5R^6)_kR^{13}$, $NR^{11}(CR^5, R^6)_kR^{13}$, $O(CR^5R^6)_k OR^{13}$, $NR^{11}(CR^5R^6)_kOR^{13}$, wherein $R^5$ and $R^6$ are as defined in claim 1, and wherein n and/or k independently are 0, 1, 2, 3 or 4;

q is 0, 1 or 2, g is 1 or 2, p is 1, 2 or 3 or a pharmaceutically acceptable salt or stereoisomer thereof.

3. Bisarylurea compound according to claim 1, wherein $Het^1$ is selected from

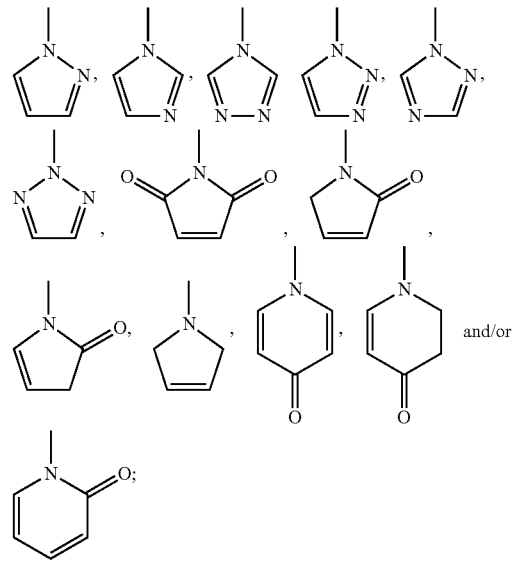

optionally substituted by 1 to 4 substituents, selected from A, $R^{13}$, Hal, $NO_2$, CN, $OR^{15}$, $NR^{15}R^{16}$, $COOR^{15}$, $CONR^{15}R^{16}$, $NR^{15}CONR^{15}R^{16}$, $NR^{16}SO_2A$, $SO_2NR^{15}R^{16}$ and $S(O)_uA$;

or a pharmaceutically acceptable salt or stereoisomer thereof.

4. Bisarylurea compound according to claim 1, selected from the compounds of formula IA, Ib, Ic, Id, Ie, If, Ig, Ih, Ii, Ij, Ik, IL, Im, In, Io, Ip, Iq, Ir, Is, It, Iu, Iv, Iw, Ix, Iy, Iz and Iaa to Iww,

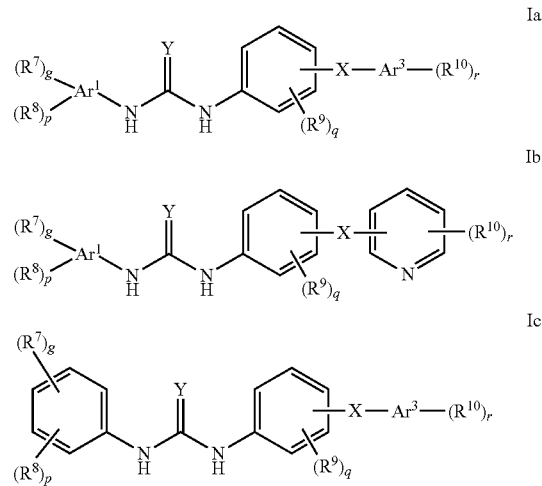

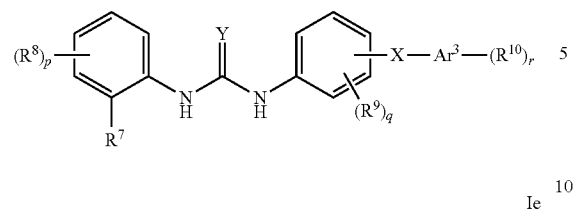
Id
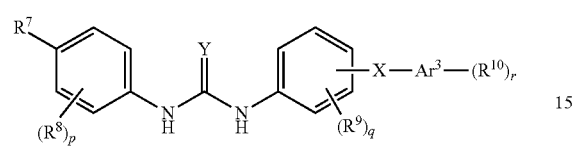
Ie
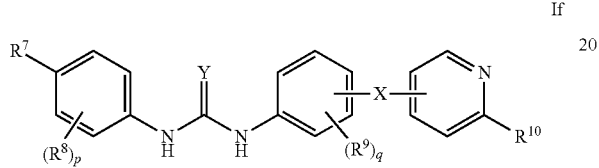
If
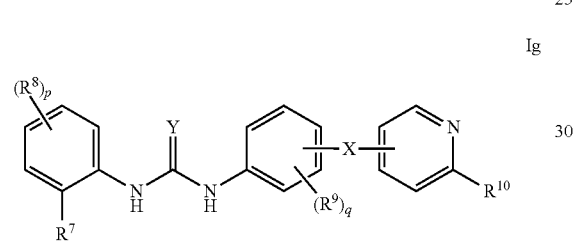
Ig
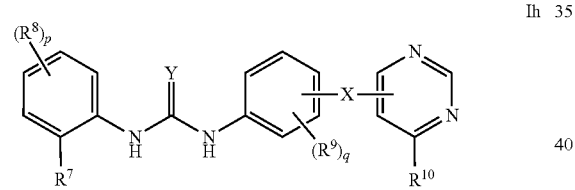
Ih
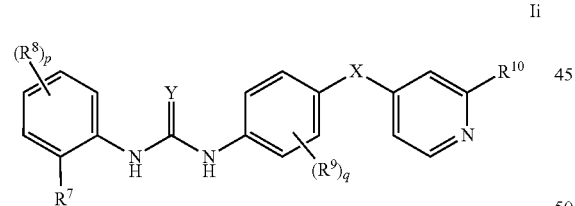
Ii
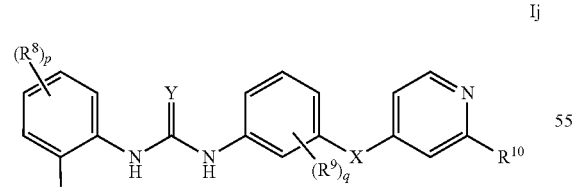
Ij
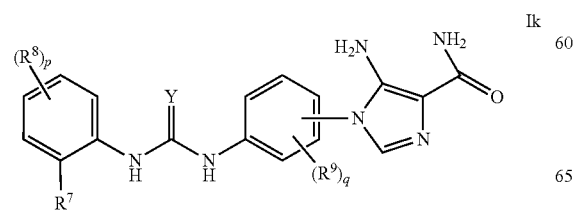
Ik
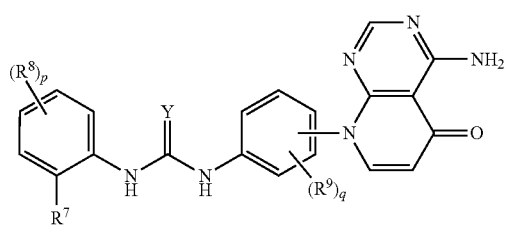
IL
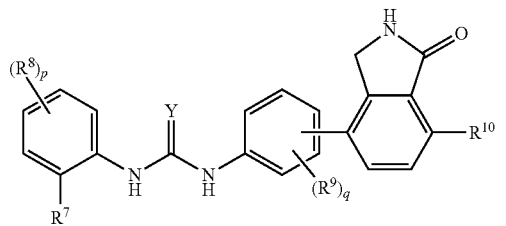
Im
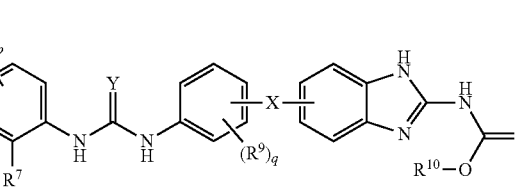
In
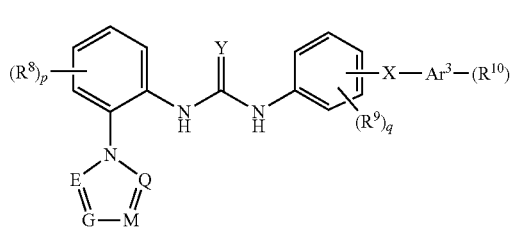
Io
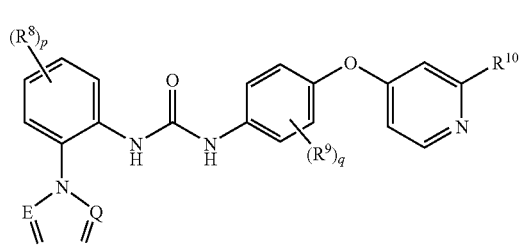
Ip
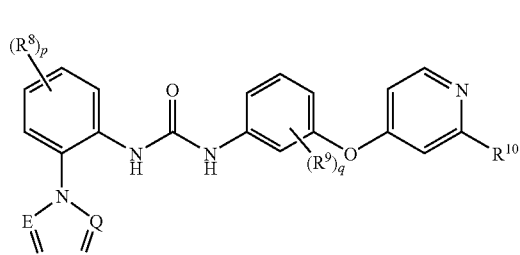
Iq Ir
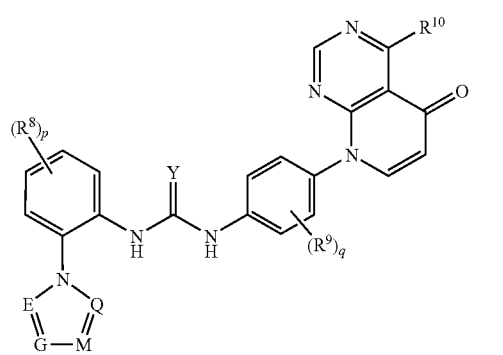
Is
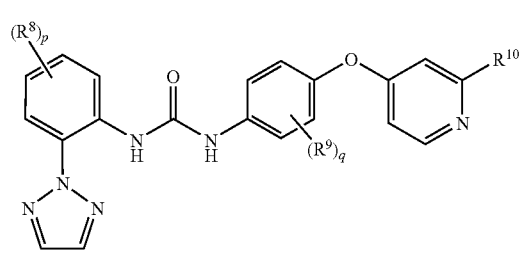
It
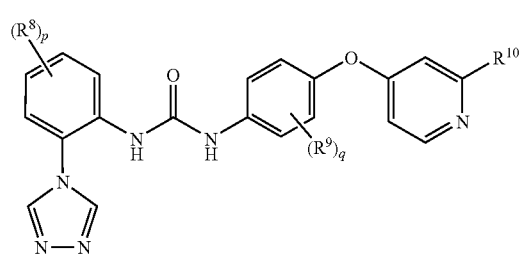
Iu
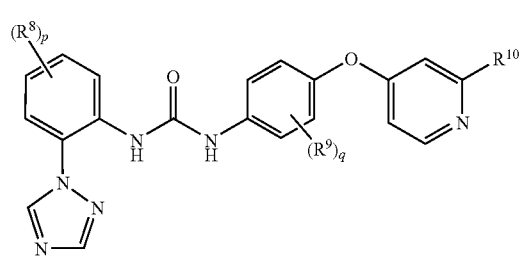
Iv
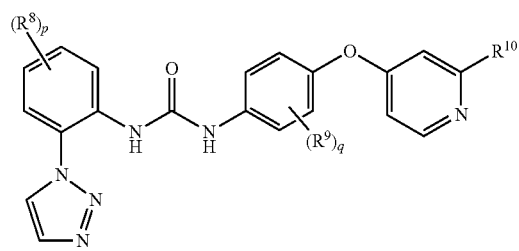
Iw
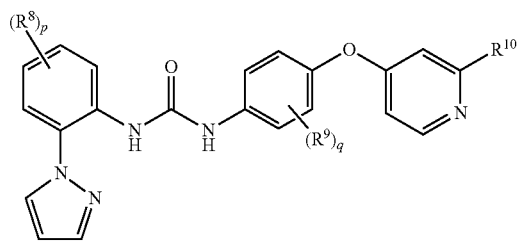
Ix
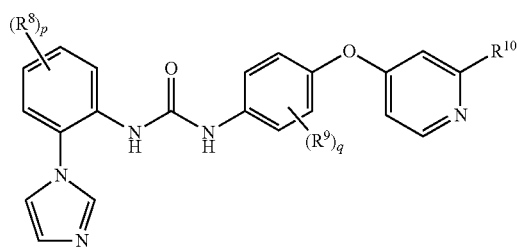
Iy
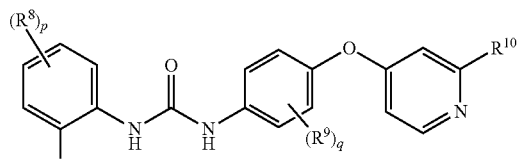
Iz
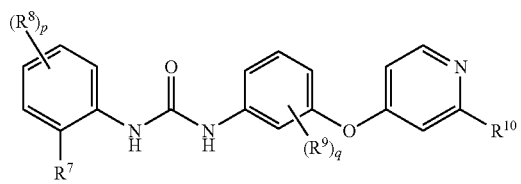
Iaa
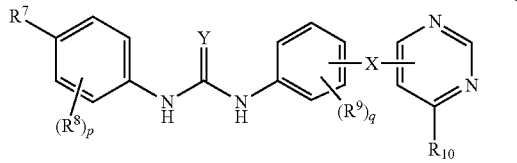
Ibb
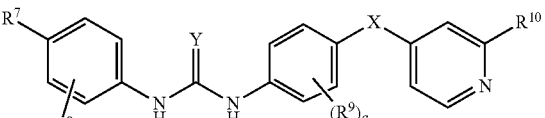
Icc
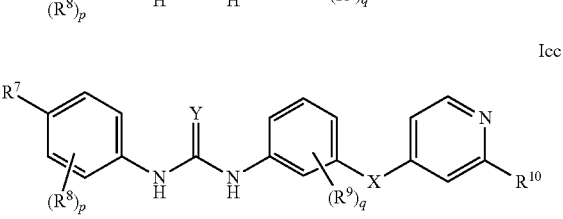

-continued

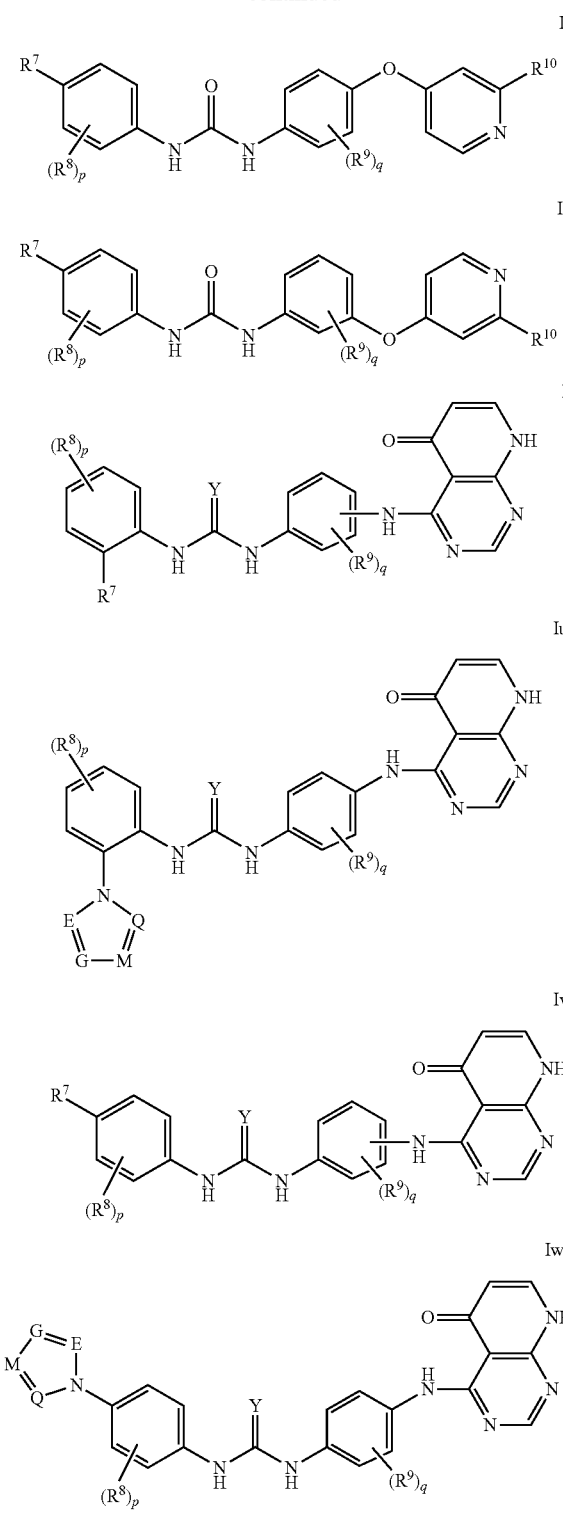

wherein R⁷, R⁸, Ar¹, Ar³, Y, X, R⁹, g, p, q and r are as defined in claim 1, R¹⁰ is H or as defined in claim 1 and wherein E, G, M and Q are selected independently from one another from N and $CR^{30}$, with the proviso that one or more of E, G, M and Q are other than nitrogen atoms; or a pharmaceutically acceptable salt or stereoisomer thereof.

5. Bisarylurea compound according to claim 1, selected from
- 4-{4-[3-(2-[1,2,4]Triazol-4-yl-5-trifluoromethyl-phenyl)-ureido]-phenoxy}-pyridine-2-carboxylic acid methylamide,
- 4-{4-[3-(2-[1,2,4]Triazol-1-yl-5-trifluoromethyl-phenyl)-ureido]-phenoxy}-pyridine-2-carboxylic acid methylamide,
- 4-{4-[3-(2-[1,2,3]Triazol-1-yl-5-trifluoromethyl-phenyl)-ureido]-phenoxy}-pyridine-2-carboxylic acid methylamide,
- 4-{4-[3-(2-Imidazol-1-yl-5-trifluoromethyl-phenyl)-ureido]-phenoxy}-pyridine-2-carboxylic acid methylamide,
- 4-{4-[3-(2-Pyrazol-1-yl-5-trifluoromethyl-phenyl)-ureido]-phenoxy}-pyridine-2-carboxylic acid methylamide,
- 1-[4-(4-Amino-5-oxo-5H-pyrido[2,3-d]pyrimidin-8-yl)-phenyl]-3-(2-[1,2,4]triazol-1-yl-5-trifluoromethyl-phenyl)-urea;
- 1-[4-(4-Amino-5-oxo-5H-pyrido[2,3-d]pyrimidin-8-yl)-phenyl]-3-(2-[1,2,3]triazol-1-yl-5-trifluoromethyl-phenyl)-urea;
- 1-[4-(Pyridin-4-yloxy)-phenyl]-3-(2-[1,2,3]triazol-1-yl-5-trifluoromethyl-phenyl)-urea;
- 1-[4-(Pyridin-4-yloxy)-phenyl]-3-(2-[1,2,4]triazol-1-yl-5-trifluoromethyl-phenyl)-urea;
- 5-Amino-1-{4-[3-(2-[1,2,3]triazol-1-yl-5-trifluoromethyl-phenyl)-ureido]-phenyl}-1H-imidazole-4-carboxylic acid amide;
- 5-Amino-1-{4-[3-(2-[1,2,4]triazol-1-yl-5-trifluoromethyl-phenyl)-ureido]-phenyl}-1H-imidazole-4-carboxylic acid amide;
- 1-[4-(4-Amino-5-oxo-5H-pyrido[2,3-d]pyrimidin-8-yl)-phenyl]-3-(2-pyrazol-1-yl-5-trifluoromethyl-phenyl)-urea;
- 1-(2-Pyrazol-1-yl-5-trifluoromethyl-phenyl)-3-[4-(pyridin-4-yloxy)-phenyl]-urea;
- 5-Amino-1-{4-[3-(2-pyrazol-1-yl-5-trifluoromethyl-phenyl)-ureido]-phenyl}-1H-imidazole-4-carboxylic acid amide;
- 1-(2-Imidazol-1-yl-5-trifluoromethyl-phenyl)-3-[4-(pyridin-4-yloxy)-phenyl]-urea;
- 1-[4-(5-Oxo-5,8-dihydro-pyrido[2,3-d]pyrimidin-4-ylamino)-phenyl]-3-(2-[1,2,3]triazol-1-yl-5-trifluoromethyl-phenyl)-urea;
- 1-[4-(5-Oxo-5,8-dihydro-pyrido[2,3-d]pyrimidin-4-ylamino)-phenyl]-3-(2-[1,2,4]triazol-1-yl-5-trifluoromethyl-phenyl)-urea;
- 4-{4-[3-(2-[1,2,4]Triazol-1-yl-5-trifluoromethyl-phenyl)-ureido]-phenoxy}-pyridine-2-carboxylic acid (2-hydroxy-ethyl)-amide;
- 1-[4-(4-Amino-5-oxo-5H-pyrido[2,3-d]pyrimidin-8-yl)-phenyl]-3-(2-imidazol-1-yl-5-trifluoromethyl-phenyl)-urea;
- 1-[4-(Pyridin-4-yloxy)-phenyl]-3-(2-[1,2,4]-triazol-4-yl-5-trifluoromethyl-phenyl)-urea;
- 1-[4-(4-Amino-5-oxo-5H-pyrido[2,3-d]pyrimidin-8-yl)-phenyl]-3-(2-[1,2,4]triazol-4-yl-5-trifluoromethyl-phenyl)-urea;
- (5-{4-[3-(2-[1,2,4]Triazol-4-yl-5-trifluoromethyl-phenyl)-ureido]-phenoxy}-1H-benzoimidazol-2-yl)-carbamic acid methyl ester;
- (5-{4-[3-(2-[1,2,3]Triazol-1-yl-5-trifluoromethyl-phenyl)-ureido]-phenoxy}-1H-benzoimidazol-2-yl)-carbamic acid methyl ester;
- (5-{4-[3-(2-[1,2,4]-Triazol-1-yl-5-trifluoromethyl-phenyl)-ureido]-phenoxy}-1H-benzoimidazol-2-yl)-carbamic acid methyl ester;

(5-{4-[3-(2-Imidazol-1-yl-5-trifluoromethyl-phenyl)-ureido]-phenoxy}-1H-benzoimidazol-2-yl)-carbamic acid methyl ester;

(5-{4-[3-(2-Pyrazol-1-yl-5-trifluoromethyl-phenyl)-ureido]-phenoxy}-1H-benzoimidazol-2-yl)-carbamic acid methyl ester;

4-{3-Fluoro-4-[3-(2-pyrazol-1-yl-5-trifluoromethyl-phenyl)-ureido]-phenoxy}-pyridine-2-carboxylic acid methylamide;

4-{3-Fluoro-4-[3-(2-[1,2,3]triazol-1-yl-5-trifluoromethyl-phenyl)-ureido]-phenoxy}-pyridine-2-carboxylic acid methylamide;

4-{3-Fluoro-4-[3-(2-imidazol-1-yl-5-trifluoromethyl-phenyl)-ureido]-phenoxy}-pyridine-2-carboxylic acid methylamide;

4-{3-Fluoro-4-[3-(2-[1,2,4]triazol-1-yl-5-trifluoromethyl-phenyl)-ureido]-phenoxy}-pyridine-2-carboxylic acid methylamide;

4-{3-Fluoro-4-[3-(2-[1,2,4]triazol-4-yl-5-trifluoromethyl-phenyl)-ureido]-phenoxy}-pyridine-2-carboxylic acid methylamide;

4-{4-[3-(4-[1,2,4]Triazol-1-yl-3-trifluoromethyl-phenyl)-ureido]-phenoxy}-pyridine-2-carboxylic acid methylamide;

4-{4-[3-(4-[1,2,3]Triazol-1-yl-3-trifluoromethyl-phenyl)-ureido]-phenoxy}-pyridine-2-carboxylic acid methylamide;

4-(4-{3-[4-(2,2-Dimethyl-5-oxo-pyrrolidin-1-yl)-3-trifluoromethyl-phenyl]-ureido}-phenoxy)-pyridine-2-carboxylic acid methylamide;

4-(4-{3-[2-(3-Methyl-2,5-dioxo-imidazolidin-1-yl)-5-trifluoromethyl-phenyl]-ureido}-phenoxy)-pyridine-2-carboxylic acid methylamide;

4-(4-{3-[4-(3-Oxo-2-aza-bicyclo[2.2.2]oct-2-yl)-3-trifluoromethyl-phenyl]-ureido}-phenoxy)-pyridine-2-carboxylic acid methylamide;

4-(4-{3-[4-(2-Oxo-oxazolidin-3-yl)-3-trifluoromethyl-phenyl]-ureido}-phenoxy)-pyridine-2-carboxylic acid methylamide;

1-[4-(Pyridin-4-yloxy)-phenyl]-3-(3-pyrrol-1-yl-phenyl)-urea;

4-{4-[3-(4-Chloro-5-methyl-2-pyrrol-1-yl-phenyl)-ureido]-phenoxy}-pyridine-2-carboxylic acid methylamide;

or a pharmaceutically acceptable salt or stereoisomer thereof.

6. Bisarylurea compound according to claim 1 as a medicament.

7. Bisarylurea compound according to claim 1 as a kinase inhibitor.

8. Bisarylurea compound according to claim 7, wherein the kinases are selected from raf-kinases, Tie-kinases, PDGFR-kinases and VEGFR-kinases.

9. Pharmaceutical composition, wherein it contains one or more compounds according to claim 1.

10. Pharmaceutical composition, wherein it contains one or more additional compounds, selected from the group consisting of physiologically acceptable excipients, auxiliaries, adjuvants, carriers and pharmaceutical active ingredients other than the compounds according to claim 1.

11. Process for the manufacture of a pharmaceutical composition, wherein one or more compounds according to claim 1 and one or more compounds, selected from the group consisting of carriers, excipients, auxiliaries and pharmaceutical active ingredients other than the compounds according to claim 1, is processed by mechanical means into a pharmaceutical composition that is suitable as dosageform for application and/or administration to a patient.

12. Method for producing compounds of formula I of claim 1, wherein a) A compound of formula II,

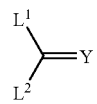

wherein
L¹ and L² either independently from one another represent a leaving group, or together represent a leaving group, and Y is as defined above/below,
is reacted with b) a compound of formula III

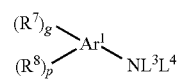

III wherein
L³ and L⁴ are independently from one another H or a metal ion, and wherein R⁷, R⁸, g, p and Ar¹ are as defined in claim 1,
and c) a compound of formula IV,

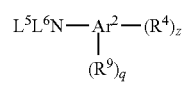

IV wherein
L⁵ and L⁶ are independently from one another H or a metal ion, and R⁹, q, Ar², R⁴, and z are as defined in claim 1,
and optionally d) isolating and/or treating the compound of formula I obtained by said reaction with an acid, to obtain the salt thereof.

* * * * *